(12) United States Patent
Olsen

(10) Patent No.: US 8,852,594 B2
(45) Date of Patent: Oct. 7, 2014

(54) COMPOSITIONS AND METHODS FOR THE THERAPY AND DIAGNOSIS OF CYTOMEGALOVIRUS INFECTIONS

(75) Inventor: Ole Olsen, Everett, WA (US)

(73) Assignee: Theraclone Sciences, Inc., Seattle, WA (US)

( * ) Notice: Subject to any disclaimer, the term of this patent is extended or adjusted under 35 U.S.C. 154(b) by 0 days.

(21) Appl. No.: 13/486,569

(22) Filed: Jun. 1, 2012

(65) Prior Publication Data

US 2012/0263734 A1 Oct. 18, 2012

Related U.S. Application Data

(63) Continuation of application No. 13/109,632, filed on May 17, 2011, now Pat. No. 8,268,309, which is a continuation of application No. 12/401,585, filed on Mar. 10, 2009, now Pat. No. 7,982,012.

(60) Provisional application No. 61/068,798, filed on Mar. 10, 2008.

(51) Int. Cl.
*A61K 39/42* (2006.01)

(52) U.S. Cl.
USPC .................................. 424/147.1; 424/133.1

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 3,896,111 A | 7/1975 | Kupchan et al. |
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 4,485,045 A | 11/1984 | Regen |
| 4,544,545 A | 10/1985 | Ryan et al. |
| 4,554,101 A | 11/1985 | Hopp |
| 4,676,980 A | 6/1987 | Segal et al. |
| 4,683,202 A | 7/1987 | Mullis |
| 4,816,567 A | 3/1989 | Cabilly et al. |
| 4,975,278 A | 12/1990 | Senter et al. |
| 5,013,556 A | 5/1991 | Woodle et al. |
| 5,053,394 A | 10/1991 | Ellestad et al. |
| 5,208,020 A | 5/1993 | Chari et al. |
| 5,229,275 A | 7/1993 | Goroff |
| 5,416,064 A | 5/1995 | Chari et al. |
| 5,500,362 A | 3/1996 | Robinson et al. |
| 5,545,806 A | 8/1996 | Lonberg et al. |
| 5,545,807 A | 8/1996 | Surani et al. |
| 5,567,610 A | 10/1996 | Borrebaeck et al. |
| 5,569,825 A | 10/1996 | Lonberg et al. |
| 5,571,894 A | 11/1996 | Wels et al. |
| 5,587,458 A | 12/1996 | King et al. |
| 5,591,669 A | 1/1997 | Krimpenfort et al. |
| 5,641,870 A | 6/1997 | Rinderknecht et al. |
| 5,648,237 A | 7/1997 | Carter |
| 5,712,374 A | 1/1998 | Kuntsmann et al. |
| 5,714,586 A | 2/1998 | Kunstmann et al. |
| 5,731,168 A | 3/1998 | Carter et al. |
| 5,739,116 A | 4/1998 | Hamann et al. |
| 5,739,277 A | 4/1998 | Presta et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,789,199 A | 8/1998 | Joly et al. |
| 5,821,337 A | 10/1998 | Carter et al. |
| 5,837,234 A | 11/1998 | Gentile et al. |
| 5,840,523 A | 11/1998 | Simmons et al. |
| 5,869,046 A | 2/1999 | Presta et al. |
| 5,877,296 A | 3/1999 | Hamann et al. |
| 6,331,415 B1 | 12/2001 | Cabilly et al. |

(Continued)

FOREIGN PATENT DOCUMENTS

| | | |
|---|---|---|
| EP | 73657 A1 | 3/1983 |
| EP | 183070 A2 | 6/1986 |

(Continued)

OTHER PUBLICATIONS

Paul, Fundamental Immunology, 3rd Edition, 1993, pp. 292-295.*
Dall'Acqua et al., Methods 2005; 36:43-60.*
McGregor & Choi, Expert Opin. Drug Metab Toxicol, 2011; 7(10):1245-65.*
Jacob et al., Virology 2013 dx.doi.org/10.1016/j.virol.2013.06.002.*
Altschul et al. "Basic Local Alignment Search Tool." *J. Mol. Bio.* 215.3(Oct. 1990):403-410.
Altschul et al. "Gapped BLAST and PSI-BLAST: A New Generation of Protein Database Search Programs." *Proc. Natl. Acad. Sci. USA.* 25.17(1997):3389-3402.
ATCC No. 12424 retrieved Aug. 26, 2011.
ATCC No. 16045 retrieved Aug. 26, 2011.

(Continued)

*Primary Examiner* — Ram R Shukla
*Assistant Examiner* — Jessica H Roark

(57) ABSTRACT

The present invention provides anti-cytomegalovirus antibodies and related compositions and methods. These antibodies may be used in the diagnosis, prevention, and treatment of cytomegalovirus infection.

4 Claims, 16 Drawing Sheets

(56) References Cited

U.S. PATENT DOCUMENTS

| | | | | |
|---|---|---|---|---|
| 6,818,749 | B1* | 11/2004 | Kashmiri et al. | 530/388.85 |
| 6,824,780 | B1 | 11/2004 | Devaux et al. | |
| 8,173,362 | B2* | 5/2012 | Shenk et al. | 435/5 |
| 8,268,309 | B2* | 9/2012 | Olsen | 424/130.1 |
| 2008/0089837 | A1 | 4/2008 | Laing et al. | |
| 2012/0020980 | A1* | 1/2012 | Kauvar et al. | 424/142.1 |
| 2013/0142823 | A1* | 6/2013 | Picker et al. | 424/199.1 |

FOREIGN PATENT DOCUMENTS

| | | |
|---|---|---|
| EP | 244234 A2 | 11/1987 |
| EP | 402226 A1 | 12/1990 |
| EP | 0404097 A2 | 12/1990 |
| EP | 0425235 A2 | 5/1991 |
| WO | WO-8101145 A1 | 4/1981 |
| WO | WO-8807378 A1 | 10/1988 |
| WO | WO-9013646 A1 | 11/1990 |
| WO | WO-9100360 A1 | 1/1991 |
| WO | WO-9220373 A1 | 11/1992 |
| WO | WO-9308829 A1 | 5/1993 |
| WO | WO-9311161 A1 | 6/1993 |
| WO | WO-9316185 A2 | 8/1993 |
| WO | WO-9321232 A1 | 10/1993 |
| WO | WO-9321952 A1 | 11/1993 |
| WO | WO-9404690 A1 | 3/1994 |
| WO | WO-9411026 A2 | 5/1994 |
| WO | WO-9607321 A1 | 3/1996 |
| WO | WO-9616673 A1 | 6/1996 |
| WO | WO-9717852 A1 | 5/1997 |
| WO | WO-9738731 A1 | 10/1997 |
| WO | WO-9802463 A1 | 1/1998 |
| WO | WO-03083061 A2 | 10/2003 |

OTHER PUBLICATIONS

ATCC No. 24178 retrieved Aug. 26, 2011.
ATCC No. 27325 retrieved Aug. 26, 2011.
ATCC No. 31446 retrieved Aug. 26, 2011.
ATCC No. 31537 retrieved Aug. 26, 2011.
ATCC No. 36906 retrieved Aug. 26, 2011.
ATCC No. 56500 retrieved Aug. 26, 2011.
ATCC No. CCL 10 retrieved Aug. 26, 2011.
ATCC No. CCL 2 retrieved Aug. 26, 2011.
ATCC No. CCL 34 retrieved Aug. 26, 2011.
ATCC No. CCL 51 retrieved Aug. 26, 2011.
ATCC No. CCL 70 retrieved Aug. 26, 2011.
ATCC No. CCL 75 retrieved Aug. 26, 2011.
ATCC No. CRL 1442 retrieved Aug. 26, 2011.
ATCC No. CRL 1587 retrieved Aug. 26, 2011.
ATCC No. CRL 1651 retrieved Aug. 26, 2011.
ATCC No. HB 8065 retrieved Aug. 26, 2011.
Babcock et al. "A Novel Strategy for Generating Monoclonal Antibodies from Single, Isolated Lymphocytes Producing ANtibodies of Defined Specifications." *Proc. Natl. Acad. Sci. USA.* 93.15(1996):7483-7848.
Bird et al. "Single-Chain Antigen-Binding Proteins." *Science.* 242(1988):423-426.
Bitter et al. "Expression and Secretion Vectors for Yeast." *Methods Enzymol.* 153(987):516-544, (1987).
Bolton et al. "The Labelling of Proteins to High Specific Radioactivities by Conjugation to a 125I-Containing Acylating Agent." *Biochem. J.* 133(1973):529-538.
Brennan et al. "Preparation of Bispecific Antibodies by Chemical Recombination of Monoclonal Immunoglobulin G1 Fragments." *Science.* 229(1985):81-83.
Broglie et al. "Light-Regulated Expression of a Pea Ribulose-1,5-Biophosphate Carboxylase Small Subunit Gene in Transformed Plant Cells." *Science.* 244(1984):838-843.
Brüggemann et al. "Designer Mice: The Production of Human Antibody Repertoires in Transgenic Animals." *Year Immunol.* 7(1993):33-40.
Byers. "What Can Randomized Controlled Trials Tells Us About Nutrition and Cancer Prevention." *CA Cancer J.* 49(1999):353-361.
Capel et al. "Heterogeneity of Human IgG Fc Receptors." *ImmunoMethods.* 4.1(1994):25-34.
Carlsson et al. "Protein Thiolation and Reversible Protein-Protein Conjugation." *Biochem. J.* 173(1978):723-737.
Caron et al. "Engineered Humanized Dimeric Forms of IgC are More Effective Antibodies." *J. Exp. Med.* 176.4(1992):1191-1195.
Carter et al. "High Level *Escherichia coli* Expression and Production of a Bivalent Humanized Antibody Fragment." *Biotechnology.* 10.2(1992):163-167.
Casset et al. "A Peptide Mimetic of an Anti-CD4 Monoclonal Antibody by Rational Design." *Biochem. Biophys. Res. Commun.* 307(2003):198-205.
Chari et al. "Immunoconjugates Containing Novel Maytansinoids: Promising Anticancer Drugs." *Cancer Res.* 52.1(1992):127-131.
Chen et al. "Selection and Analysis of an Optimized Anti-VEGF Antibody: Crystal Structures of an Affinity Matured Fab in Complex With Antigen." *J. Mol. Biol.* 293(1999):865-881.
Chothia et al. "Canonical Structures for the Hypervariable Regions of Immunoglobulins." *J. Mol. Biol.* 196.4(1987):901-917.
Chothia et al. "Conformations of Immunoglobulin Hypervariable Regions." *Nature.* 342.625 (1989):877-883.
Clackson et al. "Making Antibody Fragments Using Phage Display Libraries." *Nature.* 352.6336(1991):624-628.
Clynes et al. "Fe Receptors are Required in Passive and Active Immunity to Melanoma." *PNAS.* 95.2(1998):652-656.
Colbére-Garapin et al. "A New Dominant Hybrid Selective Marker for Higher Eukaryotic Cells." *J. Mol. Biol.* 150.1(1981):1-14.
Coruzzi et al. "Tissue-Specific and Light-Regulated Expression of a Pea Nuclear Gene Encoding the Small Subunit of Ribulose-1,5-Bisphosphate Carboxylase." *EMBO J.* 3.8(1984):1671-1679.
Cunningham et al. "High-Resolution Epitope Mapping of hGH-Receptor Interactions by Alanine-Scanning Mutagenesis." *Science.* 244(1989):1081-1085.
Dayhoff. "A Model of Evolutionary Change in Proteins—Matrices for Detecting Distant Relationships." *Atlas of Protein Sequence and Structure.* National Biomedical Research Foundation, Washington, DC. 5.Suppl. 3(1978):345-358.
Daëron. "Fc Receptor Biology." *Annu. Rev. Immunol.* 15(1997):203-234.
de Haas et al. "Fc Receptors of Phagocytes." *J. Lab. Clin. Med.* 126(1995):330-341.
De Pascalis et al. "Grafting of Abbreviated Complementarity Determing Regions Containing Specificity Determining Residues Essential for Ligand Contact to Engineer a Less Immunogenic Humanized Monoclonal Antibody." *J. Immunol.* 169(2002):3076-3084.
Dessain et al. "Exploring the Native Human Antibody Repertoire to Create Antiviral Therapeutics." *Current Topics in Microbiology and Immunology.* New York: Springer-Verlage. 317(2008):155-183.
Engelhard et al. "The Insect Tracheal System: A Conduit for the Systemic Spread of Authographa Californica M Nuclear Pholyhedrodid Virus." *PNAS.* 91.8(1994):3224-3227.
Eppstein et al. "Biological Activity of Liposome-Encapsulated Murine Interferon Gamma is Mediated by a Cell Membrane Receptor." *PNAS.* 82.11(1985):3688-3692.
Fraker et al. "Protein and Cell Membrane Iodinations with a Sparingly Soluble Chlorodamide, 1,3,4,6-Tertachloro-3a,5a-DiphenylgIcoluril." *Biochem. Biophys. Res. Comm.* 80(1978):49-57.
Freshney. *A Culture of Animal Cells.* New York: Alan R. Liss, Inc. (1983):3-4.
Gabizon et al. "Pharmacokinetics and Tissue Distribution of Doxorubicin Encapsulated in Stable Liposomes with Long Circulation Times." *J. Natl. Cancer Inst.* 81.19(1989):1484-1488.
Gazzano-Santoro et al. "A Non-Radioactive Complement-Dependent Cytotoxicity Assay for Anti-CD20 Monoclonal Antibody." *J. Immunol. Meth.* 202.2(1997):163-171.
GenBank Accession No. K02768, Jan. 5, 1995.
GenBank Accession No. L06616, Aug. 1, 1995.
GenBank Accession No. L06617, Nov. 9, 1994.
GenBank Accession No. L19271, Jul. 27, 1994.
GenBank Accession No. L19272, Jul. 27, 1994.

(56) References Cited

OTHER PUBLICATIONS

GenBank Accession No. M77327, Jan. 3, 1995.
GenBank Accession No. M77339, Feb. 26, 2002.
GenBank Accession No. M99663, Oct. 17, 2007.
GenBank Accession No. X01668, Mar. 1, 1999.
GenBank Accession No. X17264, Nov. 14, 2006.
GenBank Accession No. X92214, Oct. 30, 1995.
Graham et al. "Characteristics of a Human Cell Line Transformed by DNA From Human Adenovirus Type 5." *J. Gen. Virol.* 36.1(1977):59-72.
Granziero et al. "Adoptive Immunotherapy Prevents Prostate Cacner in a Transgenic Animal Model." *Eur. J. Immunol.* 29(1999):1127-1138.
Gruber et al. "Efficient Tumor Cell Lysis Mediated by a Bispecific Single Chain Antibody Expressed in *Escherichia coli.*" *J. Immunol.* 152.11(1994):5368-5374.
Guss et al. "Structure of the IgC-Binding Regions of Streptococcal Protein G." *EMBO J.* 5.7(1986):1567-1575.
Guyer et al. "Immunoglobulin Binding by Mouse Intestinal Epithelial Cell Receptors." *J. Immunol.* 117.2(1976):587-593.
Hartman et al. "Two Dominiant-Acting Selectable Markers for Gene Transfer Studies in Mammalian Cells." *PNAS.* 85.21(1988):8047-8051.
Hein. "Unified Approach to Alignment and Phylogenes." *Methods in Enzymology.* San Diego: Academic Press, Inc. 183(1990):626-645.
Henikoff et al. "Amino Acid Substitution Matrices from Protein Blocks." *PNAS.* 89(1992):10915-10919.
Higgins et al. "Fast and Sensitive Multiple Sequence Alignments on a Microcomputer." *CABIOS.* 5.2(1989):151-153.
Hollinger et al. "Disabodies: Small Bivalent and Bispecific Antibody Fragments." *PNAS.* 90.14(1993):6444-6448.
Holm et al. "Functional Mapping and Single Chain Construction of the Anti-Cytokeratin 8 Monoclonal Antibody TS1." *Mol. Immunol.* 44(2007):1075-1084.
Honegger et al. "Yet Another Numbering System for Immunoglobulin Variable Domains: An Automatic Modeling and Analysis Tool." *J. Mol. Biol.* 309.3(2001):657-670.
Hwang et al. "Hepatic Uptake and Degradation of Unilamellar Sphingomyelin/Cholesterol Liposomes: A Kinetic Study." *PNAS.* 77.7(1980):4030-4034.
Jakobovits et al. "Analysis of Homozygous Mutant Chimeric Mice: Deletion of the Immunoglobulin Heavy-Chain Joining Region Block B-Cell Development and Antibody Production." *PNAS.* 90.6(1993):2551-2555.
Jakobovits et al. "Germ-Line Transmission and Expression of a Human-Derived Yeast Artificial Chromosome." *Nature.* 362.6417(1993):255-258.
Jones et al. "Replacing the Complementarity-Determing Regions in a Human Antibody with Those from a Mouse." *Nature.* 321.6069(May 1986):522-525.
Kim et al. "Localization of the SIte of the Murine IgG1 Molecule That is Involved in Binding to the Murine Intestinal Fc Receptor." *Eur. J. Immunol.* 24(1994):2429-2434.
Kostelny et al. "Formation of a Bispecific Antibody by the Use of Leucine Zippers." *J. Immunol.* 148.5(1992):1547-1553.
Kroll et al. "A Multifunctional Prokaryotic Protein Expression System: Overproduction, Affinity Purification, and Selective Detection." *DNA Cell Biol.* 12.5(1993):441-453.
Kyte et al. "A Simple Method for Displaying the Hydropathic Character of a Protein." *J. Mol. Biol.* 157.1(1982):105-132.
Köhler et al. "Continuous Cultures of Fused Cells Secreting Antibody of Predefined Specificity." *Nature.* 256.5517(1975):495.
Lefranc et al. "IMGt, the International ImMunoGeneTics Database." *Nucl. Acid Res.* 27.1(1999):209-212.
Lindmark et al. "Binding of Immunoglobulins to Protein A and Immunoglobulin Levels in Mammalian Sera." *J. Immunol. Meth.* 62.1(1983):1-13.
Liu et al. "Eradication of Large Colon Tumor Xenografts by Targeted Delivery of Maytansinoids." *PNAS.* 93.16(1996):8618-8623.

Logan et al. "Adenovirus Tripartite Leader Sequence Enhances Translation of mRNAs Late after Infection." *PNAS.* 81.12(1984):3655-3659.
Lowy et al. "Isolation of Transforming DNA: Cloning the Hamster aprt Gene." *Cell.* 22.3(1980):817-823.
MacCallum et al. "Antibody-Antigen Interactions: Contact Analyses and Binding Site Topography . . ." *J. Mol. Biol.* 262(1996):732-745.
Maddox et al. "Elevated Serum Levels in Human Pregnancy of a Molecule Immunochemically Similar to Eosinophil Granule Major Basic Protein." *J. Exp. Med.* 158(1983):1211-1226.
Marks et al. "By-Passing Immunization: Human Antibodies from V-Gene Libraries Displayed on Phage." *J. Mol. Biol.* 222.3(1991):581-597.
Martin et al. "Irreversible Coupling of Immunoglobulin Fragments to Performed Vesicles." *J. Biol. Chem.* 257(1982):286-288.
Mather et al. "Culture of Testicular Cells in Hormone-Supplemented Serum-Free Medium." *Ann. NY Acad. Sci.* 383(1982):44-68.
Mather. "Establishment and Characterization of Two Distinct Mouse Testicular Epithelial Cell Lines." *Biol. Reprod.* 23.1(1980):243-251.
McGregor et al. "Molecular Cloning of the Guinea Pig Cytomegalovirus (GPCMV) Genome as an Infectious Bacterial Artificial Chromosome (BAC) in *Escherichia coli.*" *Mol. Genetics Metab.* 72.1(2001):15-26.
Mclean et al. "Recognition of Human Cytomegalovirus by Human Primary Immunoglobulins Identifies an Innate Foundation to an Adaptive Immune Response." *J. Immunol.* 174.8(2005):4768-4778.
Millstein et al. "Hybrid Hybridomas and Their Use in Immunohistochemistry." *Nature.* 305.5934(1983):537-539.
Morimoto et al. "Single-Step Purification of F(ab')$_2$ Fragments of Mouse Monoclonal Antibodies (Immunoglobulins G1) by Hydrophobic Interaction High Performance Liquid Chromatography Using TSKgel Phenyl-5PW." *J. Biochem. Biophys. Meth.* 24.1-2(1992):101-117.
Morrison et al. "Chimeric Human Antibody Molecules: Mouse Antigen-Binding Domains with Human Constant Region Domains." *PNAS.* 81.21(1984):6851-6855.
Morrison. "The Determination of the Exposed Proteins on Membranes by the Use of Lactoperoxidase." *Meth. Enzym.* 32(1974):103-109.
Murakami et al. "Cell Cycle Regulations, Oncogenes, and Antieoplastic Drugs." Mendelsohn et al., eds. *The Molecular Basis of Cancer.* Philadelphia: W.B. Saunders. (1995)Ch. 1:3-17.
Myers et al. "Optimal Alignments in Linear Space." *CABIOS.* 4.1(1988):11-17.
Needleman et al. "A General Method Applicable to the Search for Similarities in the Amino Acid Sequence of Two Proteins." *J. Mol. Bio.* 48.3(1970):443-453.
Neuberget et al. "Recombinant Antibodies Possessing Novel Effector Functions." *Nature.* 321(1984):604-608.
Ohlin et al. "Fine Specificity of the Human Immune Response to the Major Neutralization Epitopes Expressed on Cytomegalovirus gp58/116 (gB), as Determined with Human Monoclonal Antibodies." *J. Virol.* 67.2(1993):703-710.
Pearson et al. "Improved Tools for Biological Sequence Comparison." *PNAS.* 85.8(1988):2444-2448.
Plückthun. *The Pharmacology of Monoclonal Antibodies.* Rosenberg et al., eds. New York: Springer-Verlag. 113(1994):269-315.
Porath. "Immobilized Metal Ion Affinity Chromatography." *Prot. Expr. Purif.* 3.4(1992):263-281.
Presta. "Antibody Engineering." *Curr. Op. Struct. Biol.* 2.4(1992):593-596.
Ravetch et al. "Fc Receptors." *Annu. Rev. Immunol.* 9(1991):457-492.
Reichmann et al. "Reshaping Human Antibodies for Therapy." *Nature.* (1988):323-327.
Rhodes et al. "Transformation of Maize by Electroporation of Embryos." *Methods Mol. Biol.* 55(1995):121-131.
Robinson. "Comparison of Labeled Trees with Valency Three." *J. Comb. Theor.* 11(1971):105-119.
Rothlein et al. "Two Distinct Mechanisms of Cytotoxicity by Porcine Alveolar Macrophages in Antibody-Dependent and Immobilized Immune Complex-Dependent Cellular Cytotoxicity." *J. Immunol.* 131.3(1983):1438-1442.

(56) References Cited

OTHER PUBLICATIONS

Rudikoff et al. "Single Amino Acid Substitution Altering Antigen-Binding Specificity." *PNAS*. 79(1982):1979-1983.

Ruiz et al. "IMGt, the International ImMunoGeneTics Database." *Nucl. Acid Res.* 28.1(2000):219-221.

Saitou et al. "The Neighbour-Joining Method:A New Method for Reconstructing Phylogenetic Trees." *Mol. Biol. Evol.* 4.4(1987):406-425.

Scatchard. "The Attractions of Proteins for Small Molecules and Ions." *Ann. N.Y. Acad. Sci. USA*. 51.4(1949):660-672.

Schrader et al. "Location, Location, Timing: Analysis of Cytomegalovirus Epitopes for Neutralizing Antibodies." *Immunol. Lett.* 112.1(2007):58-60.

Shalaby et al. "Development of Humanized Bispecific Antibodies Reactive with Cytotoxic Lymphocytes and Tumor Cells Overexpressing the HER2 Protooncogene." *J. Exp. Med.* 175.1(1992):217-225.

Shopes. "A Genetically Engineered Human IgC Mutant with Enhanced Cytolytic Activity." *J. Immunol.* 148.9(1992):2918-2922.

Skolnick et al. "From Genes to Protein Structure and Function: Novel Applications of Computational Approaches in the Genomic Era." *Trends Biotechnol.* 18(2000):34-39.

Smith et al. "Comparison of Biosequences." *Adv. Apl. Math.* 2.4(1981):482-489.

Stevenson. "A Chimeric Antibody with Dual Fc Regions (bisFaFc) Prepared by Manipulations at the IgC Hinge." *Anti-Cancer Drug Design*. 3(1989):219-230.

Stites et al., ed. *Basic and Clinical Immunology*. Norwalk, CT: Appleton & Lange. 8th ed. (1994)ch 6:71.

Suresh et al. "Bispecific Monoclonal Antibodies from Hybrid Hybridomas." *Methods in Enzymology*. 121(1986):210-228.

Syvanen et al. "Preparation of $^{125}$I-Catalytic Subunit of Aspartate Transcarbamylase and Its Use in Studies of the Regulatory Subunit." *J. Biol. Chem.* 248(1973):3762-3768.

Takamatsu et al. "Expression of Bacterial Chloramphenicol Acetyltransferase Gene in Tobacco Plants Mediated by TMV-RNA." *EMBO J.* 6.2(1987):307-311.

Traunecker et al. "Bispecific Single Chain Molecules (Janusins) Target Cytotoxic Lymphocytes on HIV Infected Cells." *EMBO J.* 10.12(1991):3655-3659.

Tutt et al. "Trispecific F(ab')$_3$ Derivatives that use Cooperative Signaling Via the TCR/CD3 Complex and CD2 to Activate and Redirect Resting Cytotoxic T Cells." *J. Immunol.* 147.1(1991):60-69.

Urlaub et al. "Isolation of Chinese Hamster Cell Mutants Deficient in Dihydrofolate Reductase Activity." *PNAS*. 77.7(1980):4216-4220.

Vadjos et al. "Comprehensive Functional Maps of the Antigen-Binding Site of an Anti-ErbB2 Antibody Obtained With Shotgun Scanning Mutagenesis." *J. Mol. Biol.* 320(2002):415-428.

Van Heeke et al. "Expression of Human Asparagine Synthetaste in *Escherichia coli*." *J. Biol. Chem.* 264(1989):5503-5509.

Verhoeyen et al. "Reshaping Human Antibodies: Grafting an Antilysozyme Activity." *Science*. 239(1988):1534-1536.

Vitetta et al. "Redesigning Nature's Poisons to Create Anti-Tumor Reagents." *Science*. 238(1987):1098-1104.

Wigler et al. "Transfer of Purified Herpes Virus Thymidine Kinase Gene to Cultured Mouse Cells." *Cell*. 11.1(1977):223-232.

Wigler et al. "Transformation of Mammalian Cells with an Amplifiable Dominant-Acting Gene." *PNAS*. 77.6(1980):3567-3570.

Wilbur et al. "Rapid Similarity Searches of Nucleic Acid and Protein Data Banks." *Proc. Natl. Acad. Sci. USA*. 80.3(1983):726-730.

Winter et al. "The Expression of Heat Shock Protein and Cognate Genes During Plant Development." *Results Probl. Cell Differ.* 17(1991):85-105.

Wolff et al. "Monoclonal Antibody Homodimers: Enhanced Antitumor Activity in Nude Mice." *Cancer Res.* 53(1993):2560-2565.

Wu et al. "Humanization of a Murine Monoclonal Antibody by Simultaneous Optimization of Framework and CDR Residues." *J. Mol. Biol.* 294(1999):151-162.

Yaniv. "Enhancing Elements for Activation of Eukaryotic Promoters." *Nature*. 297.5861(1982):17-18.

Zapata et al. "Engineering Linear F(ab')$_2$ Fragments for Efficient Production in *Eschserichia coli* and Enhanced Antiproliferative Activity." *Protein Eng.* 8.10(1995):1057-1062.

Massey et al. "Catalytic Antibodies Catching on: Designer Proteins, Accelerated Syntheses, and Better Purification Procedures are some of the Potential Benefits of a Melding of the Best of Antibodies and Catalysts." *Nature*. 328.6129(1987):457-458.

Murry. "Genetic Engineering." McGraw Hill Yearbook of Science and Tech. New York: McGraw Hill. (1992):191-196.

\* cited by examiner

```
                    SEQUENCE LISTING

<160> NUMBER OF SEQ ID NOS: 126

<210> SEQ ID NO 1
<211> LENGTH: 1422
<212> TYPE: DNA
<213> ORGANISM: Homo sapiens

<400> SEQUENCE: 1
atggagtttg ggctgagctg ggttttcctc gttgctcttt taagaggtgt ccagtgtcag      60
gtacatctgg tggagtcggg gggaggcgtc gtccagcctg gtagggccct gagactctcc     120
tgtgcagcca ctggattcac atttagtaat cacggcatac attgggtccg ccaggctcca     180
ggcaaggggc tggagtggct ggcagttatt tcaagcgatg gagatgatga ccgttacgca     240
gactccgtga agggtcgatt cagcgtctcc agagacaatt ccaagaacac cgtgcatctg     300
cagatgaatg gcctgagacc tgacgacacg gctatttatt tctgtgcgcg agatgggagg     360
tgtggtgaac ctaagtgcta ctcagggttg cctgattact ggggccgggg gaccctggtc     420
accgtctcga gcgcctccac caagggccca tcggtcttcc ccctggcacc ctcctccaag     480
agcacctctg ggggcacagc ggccctgggc tgcctggtca aggactactt ccccgaaccg     540
gtgacggtgt cgtggaactc aggcgccctg accagcggcg tgcacacctt cccggctgtc     600
ctacagtcct caggactcta ctccctcagc agcgtggtga ccgtgccctc cagcagcttg     660
ggcacccaga cctacatctg caacgtgaat cacaagccca gcaacaccaa ggtggacaag     720
agagttgagc ccaaatcttg tgacaaaact cacacatgcc caccgtgccc agcacctgaa     780
ctcctggggg gaccgtcagt cttcctcttc ccccaaaac ccaaggacac cctcatgatc     840
tcccggaccc ctgaggtcac atgcgtggtg gtggacgtga gccacgaaga ccctgaggtc     900
aagttcaact ggtacgtgga cggcgtggag gtgcataatg ccaagacaaa gccgcgggag     960
gagcagtaca acagcacgta ccgtgtggtc agcgtcctca ccgtcctgca ccaggactgg    1020
ctgaatggca aggagtacaa gtgcaaggtc tccaacaaag ccctcccagc ccccatcgag    1080
aaaaccatct ccaaagccaa aggcagcccc gagaaccac aggtgtacac cctgccccca    1140
tcccgggagg agatgaccaa gaaccaggtc agcctgacct gcctggtcaa aggcttctat    1200
cccagcgaca tcgccgtgga gtgggagagc aatgggcagc cggagaacaa ctacaagacc    1260
```

-continued

```
acgcctcccg tgctggactc cgacggctcc ttcttcctct atagcaagct caccgtggac    1320
aagagcaggt ggcagcaggg gaacgtcttc tcatgctccg tgatgcatga ggctctgcac    1380
aaccactaca cgcagaagag cctctccctg tctccgggta aa                       1422
```

```
<210> SEQ ID NO 2
<211> LENGTH: 474
<212> TYPE: PRT
<213> ORGANISM: Homo sapiens

<400> SEQUENCE: 2

Met Glu Phe Gly Leu Ser Trp Val Phe Leu Val Ala Leu Leu Arg Gly
1               5                   10                  15

Val Gln Cys Gln Val His Leu Val Glu Ser Gly Gly Gly Val Val Gln
            20                  25                  30

Pro Gly Arg Ala Leu Arg Leu Ser Cys Ala Ala Thr Gly Phe Thr Phe
        35                  40                  45

Ser Asn His Gly Ile His Trp Val Arg Gln Ala Pro Gly Lys Gly Leu
    50                  55                  60

Glu Trp Leu Ala Val Ile Ser Ser Asp Gly Asp Asp Arg Tyr Ala
65                  70                  75                  80

Asp Ser Val Lys Gly Arg Phe Ser Val Ser Arg Asp Asn Ser Lys Asn
                85                  90                  95

Thr Val His Leu Gln Met Asn Gly Leu Arg Pro Asp Asp Thr Ala Ile
            100                 105                 110

Tyr Phe Cys Ala Arg Asp Gly Arg Cys Gly Glu Pro Lys Cys Tyr Ser
        115                 120                 125

Gly Leu Pro Asp Tyr Trp Gly Arg Gly Thr Leu Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
```

```
            340                 345                 350
Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 3
<211> LENGTH: 705
<212> TYPE: DNA
<213> ORGANISM: Homo sapiens

<400> SEQUENCE: 3
atggaagccc cagcgcagct tctcttcctc ctgctactct ggctcccagc taccaccgga      60
gagattgttt tgacacagtc tccagccacc ctgtctttgt ctccagggga cagagccacc     120
ctctcctgca gggccagtca gagtgttggc gggtacttag cctggtatca acaaaagcct     180
ggccaggctc ccaggctcct cctctatgat gcatccaaca gggccactgg catcccagcc     240
aggttcagtg gcagtgggtc tgggacagac ttcactctca ccatcagcag cctagagcct     300
gaagattttg cactttatta ctgtcttcag cgtaacacgt ggcctccgct cactttcggg     360
ggagggacca aggtggagat caaacgtacg gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca aagcagacta cgagaaacac aaagtctacg cctgcgaagt cacccatcag     660
ggcctgagct cgcccgtcac aaagagcttc aacaggggag agtgt               705

<210> SEQ ID NO 4
<211> LENGTH: 235
<212> TYPE: PRT
<213> ORGANISM: Homo sapiens

<400> SEQUENCE: 4

Met Glu Ala Pro Ala Gln Leu Leu Phe Leu Leu Leu Leu Trp Leu Pro
1               5                   10                  15

Ala Thr Thr Gly Glu Ile Val Leu Thr Gln Ser Pro Ala Thr Leu Ser
            20                  25                  30

Leu Ser Pro Gly Asp Arg Ala Thr Leu Ser Cys Arg Ala Ser Gln Ser
        35                  40                  45

Val Gly Gly Tyr Leu Ala Trp Tyr Gln Gln Lys Pro Gly Gln Ala Pro
    50                  55                  60

Arg Leu Leu Leu Tyr Asp Ala Ser Asn Arg Ala Thr Gly Ile Pro Ala
```

```
            65                  70                  75                  80
Arg Phe Ser Gly Ser Gly Ser Gly Thr Asp Phe Thr Leu Thr Ile Ser
                85                  90                  95

Ser Leu Glu Pro Glu Asp Phe Ala Leu Tyr Tyr Cys Leu Gln Arg Asn
                100                 105                 110

Thr Trp Pro Pro Leu Thr Phe Gly Gly Gly Thr Lys Val Glu Ile Lys
                115                 120                 125

Arg Thr Val Ala Ala Pro Ser Val Phe Ile Phe Pro Pro Ser Asp Glu
            130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
                180                 185                 190

Thr Tyr Ser Leu Ser Ser Thr Leu Thr Leu Ser Lys Ala Asp Tyr Glu
                195                 200                 205

Lys His Lys Val Tyr Ala Cys Glu Val Thr His Gln Gly Leu Ser Ser
        210                 215                 220

Pro Val Thr Lys Ser Phe Asn Arg Gly Glu Cys
225                 230                 235

<210> SEQ ID NO 5
<211> LENGTH: 1422
<212> TYPE: DNA
<213> ORGANISM: Homo sapiens

<400> SEQUENCE: 5
atggagttgg ggctgtgctg ggttttcctc gttgctcttt taagaggtgt ccagtgccag     60
gtgcagctgg tggactctgg gggaggcatg gtccagcctg gaggtccct gagactctcc     120 tgttcagcct ctggactcac cttcagcaat tatggcatgc actgggtccg ccaggctcca     180
ggcaaggggc tggagtgggt ggcagttata tcaagtgatg gaagtaatga gcactacgca     240
gactccgtga agggccgatt cactatctcc agagacaatt caacaacat gctgtatctg     300 caaatgaaca gcctgagagc tgaggacacg gctgtctatt acagtgcgag agatgggagg     360
tgtcctgatg ttaactgcta ctcagggttg attgactatt ggggccaggg gaccctggtc     420
accgtctcga gcgcctccac caagggccca tcggtcttcc ccctggcacc ctcctccaag     480
agcacctctg ggggcacagc ggccctgggc tgcctggtca aggactactt ccccgaaccg     540
gtgacggtgt cgtggaactc aggcgccctg accagcggcg tgcacacctt cccggctgtc     600
ctacagtcct caggactcta ctccctcagc agcgtggtga ccgtgccctc agcagcttg     660 ggcacccaga cctacatctg caacgtgaat cacaagccca gcaacaccaa ggtggacaag     720
agagttgagc ccaaatcttg tgacaaaact cacacatgcc caccgtgccc agcacctgaa     780
ctcctggggg gaccgtcagt cttcctcttc ccccaaaac ccaaggacac cctcatgatc     840
tcccggaccc ctgaggtcac atgcgtggtg gtggacgtga gccacgaaga ccctgaggtc     900
aagttcaact ggtacgtgga cggcgtggag gtgcataatg ccaagacaaa gccgcgggag     960
gagcagtaca acagcacgta ccgtgtggtc agcgtcctca ccgtcctgca ccaggactgg     1020
ctgaatggca aggagtacaa gtgcaaggtc tccaacaaag ccctcccagc ccccatcgag     1080
aaaaccatct ccaaagccaa agggcagccc cgagaaccac aggtgtacac cctgccccca     1140
tcccgggagg agatgaccaa gaaccaggtc agcctgacct gcctggtcaa aggcttctat     1200
```

```
cccagcgaca tcgccgtgga gtgggagagc aatgggcagc cggagaacaa ctacaagacc    1260
acgcctcccg tgctggactc cgacggctcc ttcttcctct atagcaagct caccgtggac    1320
aagagcaggt ggcagcaggg gaacgtcttc tcatgctccg tgatgcatga ggctctgcac    1380
aaccactaca cgcagaagag cctctccctg tctccgggta aa                      1422
```

<210> SEQ ID NO 6
<211> LENGTH: 474
<212> TYPE: PRT
<213> ORGANISM: Homo sapiens

<400> SEQUENCE: 6

```
Met Glu Leu Gly Leu Cys Trp Val Phe Leu Val Ala Leu Leu Arg Gly
1               5                   10                  15

Val Gln Cys Gln Val Gln Leu Val Asp Ser Gly Gly Gly Met Val Gln
            20                  25                  30

Pro Gly Arg Ser Leu Arg Leu Ser Cys Ser Ala Ser Gly Leu Thr Phe
        35                  40                  45

Ser Asn Tyr Gly Met His Trp Val Arg Gln Ala Pro Gly Lys Gly Leu
    50                  55                  60

Glu Trp Val Ala Val Ile Ser Ser Asp Gly Ser Asn Glu His Tyr Ala
65                  70                  75                  80

Asp Ser Val Lys Gly Arg Phe Thr Ile Ser Arg Asp Asn Phe Asn Asn
                85                  90                  95

Met Leu Tyr Leu Gln Met Asn Ser Leu Arg Ala Glu Asp Thr Ala Val
            100                 105                 110

Tyr Tyr Ser Ala Arg Asp Gly Arg Cys Pro Asp Val Asn Cys Tyr Ser
        115                 120                 125

Gly Leu Ile Asp Tyr Trp Gly Gln Gly Thr Leu Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335
```

```
His Gln Asp Trp Leu Asn Gly Lys Glu Tyr Lys Cys Lys Val Ser Asn
            340                 345                 350
Lys Ala Leu Pro Ala Pro Ile Glu Lys Thr Ile Ser Lys Ala Lys Gly
            355                 360                 365
Gln Pro Arg Glu Pro Gln Val Tyr Thr Leu Pro Ser Arg Glu Glu
        370                 375                 380
Met Thr Lys Asn Gln Val Ser Leu Thr Cys Leu Val Lys Gly Phe Tyr
385                 390                 395                 400
Pro Ser Asp Ile Ala Val Glu Trp Glu Ser Asn Gly Gln Pro Glu Asn
                405                 410                 415
Asn Tyr Lys Thr Thr Pro Pro Val Leu Asp Ser Asp Gly Ser Phe Phe
            420                 425                 430
Leu Tyr Ser Lys Leu Thr Val Asp Lys Ser Arg Trp Gln Gln Gly Asn
            435                 440                 445
Val Phe Ser Cys Ser Val Met His Glu Ala Leu His Asn His Tyr Thr
            450                 455                 460
Gln Lys Ser Leu Ser Leu Ser Pro Gly Lys
465                 470
```

<210> SEQ ID NO 7
<211> LENGTH: 705
<212> TYPE: DNA
<213> ORGANISM: Homo sapiens

<400> SEQUENCE: 7

```
atggaagccc cagcgcagct tctcttcctc ctgctactct ggctcccaga taccaccgga      60
gaaattgtct tgacacagtc tccagccacc ctgtctttgt ctccagggga agagccacc     120
ctctcctgca gggccagtca gagtgttggc agatacttag cctggtacca acagaaaggt     180
ggccaggctc ccaggctcct catctatgat gcatccaaca gggccactgg catcccagcc     240
aggttcagtg gcagtgggtc tgggacagac ttcactctca ccatcgacag cctagagcct     300
gaagattttg cagtttatta ctgtcagcag cgtagcaact ggcctccgct cactttcggc     360
ggagggtcca aggtggagat caaacgtacg gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca agcagactac gagaaacac aaagtctacg cctgcgaagt cacccatcag     660
ggcctgagct cgcccgtcac aaagagcttc aacaggggag agtgt                     705
```

<210> SEQ ID NO 8
<211> LENGTH: 235
<212> TYPE: PRT
<213> ORGANISM: Homo sapiens

<400> SEQUENCE: 8

```
Met Glu Ala Pro Ala Gln Leu Leu Phe Leu Leu Leu Leu Trp Leu Pro
1               5                   10                  15
Asp Thr Thr Gly Glu Ile Val Leu Thr Gln Ser Pro Ala Thr Leu Ser
            20                  25                  30
Leu Ser Pro Gly Glu Arg Ala Thr Leu Ser Cys Arg Ala Ser Gln Ser
        35                  40                  45
Val Gly Arg Tyr Leu Ala Trp Tyr Gln Gln Lys Gly Gly Gln Ala Pro
    50                  55                  60
```

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Asp
            85                  90                  95

Ser Leu Glu Pro Glu Asp Phe Ala Val Tyr Tyr Cys Gln Gln Arg Ser
        100                 105                 110

Asn Trp Pro Pro Leu Thr Phe Gly Gly Gly Ser Lys Val Glu Ile Lys
            115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 9
<211> LENGTH: 1422
<212> TYPE: DNA
<213> ORGANISM: Homo sapiens

<400> SEQUENCE: 9
atggagttgg ggctgcgctg gttttcctc gttgctcttt taagaggtgt ccagtgtcag     60
gtgcagctgg tggagtctgg gggaggcgtg gtccagcctg gaggtccct gagactctcc    120 tgtgcagcct ctggattcac cttcagtagt aatggcatac actgggtccg ccaggctcca   180
ggcaaggggc tggactgggt ggcagttata tcatctgatg caaatgataa acaatacgca   240
gactccgtga agggccgatt caccatctcc agagacaatt ccaagaacat ggtgtatctg    300
caaatgaaca gcctgagagt tgaagacacg gctgtctatt tctgtgcgag agatgggacg    360
tgcagtggtg gtaactgcta ctcagggttg attgactatt ggggccgggg aattctggtc    420
accgtctcga gcgcctccac caagggccca tcggtcttcc ccctggcacc ctcctccaag    480
agcacctctg ggggcacagc ggccctgggc tgcctggtca aggactactt ccccgaaccg    540
gtgacggtgt cgtggaactc aggcgccctg accagcggcg tgcacacctt cccggctgtc    600
ctacagtcct caggactcta ctccctcagc agcgtggtga ccgtgccctc agcagcttg     660 ggcacccaga cctacatctg caacgtgaat cacaagccca gcaacaccaa ggtgacaag     720 agagttgagc ccaaatcttg tgacaaaact cacacatgcc caccgtgccc agcacctgaa    780
ctcctggggg gaccgtcagt cttcctcttc cccccaaaac ccaaggacac cctcatgatc    840
tcccggaccc ctgaggtcac atgcgtggtg gtggacgtga gccacgaaga ccctgaggtc    900
aagttcaact ggtacgtgga cggcgtggag gtgcataatg ccaagacaaa gccgcgggag    960
gagcagtaca acagcacgta ccgtgtggtc agcgtcctca ccgtcctgca ccaggactgg   1020
ctgaatggca aggagtacaa gtgcaaggtc tccaacaaag ccctcccagc ccccatcgag   1080
aaaaccatct ccaaagccaa agggcagccc cgagaaccac aggtgtacac cctgcccca   1140

```
tcccgggagg agatgaccaa gaaccaggtc agcctgacct gcctggtcaa aggcttctat    1200
cccagcgaca tcgccgtgga gtgggagagc aatgggcagc cggagaacaa ctacaagacc    1260
acgcctcccg tgctggactc cgacggctcc ttcttcctct atagcaagct caccgtggac    1320
aagagcaggt ggcagcaggg gaacgtcttc tcatgctccg tgatgcatga ggctctgcac    1380
aaccactaca cgcagaagag cctctccctg tctccgggta aa                       1422
```

<210> SEQ ID NO 10
<211> LENGTH: 474
<212> TYPE: PRT
<213> ORGANISM: Homo sapiens

<400> SEQUENCE: 10

```
Met Glu Leu Gly Leu Arg Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Asn Gly Ile His Trp Val Arg Gln Ala Pro Gly Lys Gly Leu
    50                  55                  60

Asp Trp Val Ala Val Ile Ser Ser Asp Ala Asn Asp Lys Gln Tyr Ala
65                  70                  75                  80

Asp Ser Val Lys Gly Arg Phe Thr Ile Ser Arg Asp Asn Ser Lys Asn
                85                  90                  95

Met Val Tyr Leu Gln Met Asn Ser Leu Arg Val Glu Asp Thr Ala Val
            100                 105                 110

Tyr Phe Cys Ala Arg Asp Gly Thr Cys Ser Gly Gly Asn Cys Tyr Ser
        115                 120                 125

Gly Leu Ile Asp Tyr Trp Gly Arg Gly Ile Leu Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320
```

```
Glu Gln Tyr Asn Ser Thr Tyr Arg Val Val Ser Val Leu Thr Val Leu
            325                 330                 335

His Gln Asp Trp Leu Asn Gly Lys Glu Tyr Lys Cys Lys Val Ser Asn
        340                 345                 350

Lys Ala Leu Pro Ala Pro Ile Glu Lys Thr Ile Ser Lys Ala Lys Gly
            355                 360                 365

Gln Pro Arg Glu Pro Gln Val Tyr Thr Leu Pro Pro Ser Arg Glu Glu
        370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 11
<211> LENGTH: 711
<212> TYPE: DNA
<213> ORGANISM: Homo sapiens

<400> SEQUENCE: 11
atggacatga gggtcccagc tcagcttctc ttcctcctgc tactctggct cccagatacc      60
accggagaaa ttgtgttgac acagtctcca gccaccttgt ctttgtctcc aggtgaaaga    120
gccaccctct cctgcagggc cagtcagagt gttggcggct acttagcctg gtaccaacag    180
aaacctggcc aggctcccag gctcctcatc tacgatgcct ccatcagggc cactggcatc    240
ccagccaggt tcagtggcag tgggtctggg acagacttca ctctcaccat cagcagccta    300
gagcctgaag attttgcagt ttattactgt caccagcgta gcaactggcc tccgctcact    360
ttcggcggag ggaccaaggt ggatatcaaa cgtacggtgg ctgcaccatc tgtcttcatc    420
ttcccgccat ctgatgagca gttgaaatct ggaactgcct ctgttgtgtg cctgctgaat    480
aacttctatc ccagagaggc caaagtacag tggaaggtgg ataacgccct ccaatcgggt    540
aactcccagg agagtgtcac agagcaggac agcaaggaca gcacctacag cctcagcagc    600
accctgacgc tgagcaaagc agactacgag aaacacaaag tctacgcctg cgaagtcacc    660
catcagggcc tgagctcgcc cgtcacaaag agcttcaaca ggggagagtg t             711

<210> SEQ ID NO 12
<211> LENGTH: 235
<212> TYPE: PRT
<213> ORGANISM: Homo sapiens

<400> SEQUENCE: 12

Met Arg Val Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45
```

Val Gly Gly Tyr Leu Ala Trp Tyr Gln Gln Lys Pro Gly Gln Ala Pro
 50                  55                  60
Arg Leu Leu Ile Tyr Asp Ala Ser Ile Arg Ala Thr Gly Ile Pro Ala
 65                  70                  75                  80
Arg Phe Ser Gly Ser Gly Ser Gly Thr Asp Phe Thr Leu Thr Ile Ser
                 85                  90                  95
Ser Leu Glu Pro Glu Asp Phe Ala Val Tyr Tyr Cys His Gln Arg Ser
            100                 105                 110
Asn Trp Pro Pro Leu Thr Phe Gly Gly Gly Thr Lys Val Asp Ile Lys
        115                 120                 125
Arg Thr Val Ala Ala Pro Ser Val Phe Ile Phe Pro Pro Ser Asp Glu
    130                 135                 140
Gln Leu Lys Ser Gly Thr Ala Ser Val Val Cys Leu Leu Asn Asn Phe
145                 150                 155                 160
Tyr Pro Arg Glu Ala Lys Val Gln Trp Lys Val Asp Asn Ala Leu Gln
                165                 170                 175
Ser Gly Asn Ser Gln Glu Ser Val Thr Glu Gln Asp Ser Lys Asp Ser
            180                 185                 190
Thr Tyr Ser Leu Ser Ser Thr Leu Thr Leu Ser Lys Ala Asp Tyr Glu
        195                 200                 205
Lys His Lys Val Tyr Ala Cys Glu Val Thr His Gln Gly Leu Ser Ser
    210                 215                 220
Pro Val Thr Lys Ser Phe Asn Arg Gly Glu Cys
225                 230                 235

<210> SEQ ID NO 13
<211> LENGTH: 1422
<212> TYPE: DNA
<213> ORGANISM: Homo sapiens

<400> SEQUENCE: 13
atggagttgg ggctgagctg gttttcctc gttgctcttt taagaggtgt ccagtgtcag      60
gtgcagctgg tggagtcggg gggaggcgtg atccagcctg gaggtccct gagactctcc    120
tgtgttgcct ctaaattcat cttcagtaac catggcatac actgggtccg ccaggctcca    180
ggcaaggggc tggagtgggt ggcggttata tcaaaagatg gactaatgc acactacgca    240
gactccgtga gggccgatt tagcatctcc agagacaact ccaaggacac tgtctttctg    300
gaaatgcgca gcctgcgacc tgaagacacg gctgtgtatt actgtgcgag agagggccgg    360
tgtattgaag aaaactgcta ctccggacag attgactatt ggggccaggg atccctggtc    420
accgtctcga gcgcctccac caagggccca tcggtcttcc ccctggcacc ctcctccaag    480
agcacctctg gggcacagc ggccctgggc tgcctggtca aggactactt ccccgaaccg    540
gtgacggtgt cgtggaactc aggcgccctg accagcggcg tgcacacctt cccggctgtc    600
ctacagtcct caggactcta ctccctcagc agcgtggtga ccgtgccctc agcagcttg    660
ggcacccaga cctacatctg caacgtgaat cacaagccca gcaacaccaa ggtggacaag    720
agagttgagc ccaaatcttg tgacaaaact cacacatgcc caccgtgccc agcacctgaa    780
ctcctggggg gaccgtcagt cttcctcttc cccccaaaac ccaaggacac cctcatgatc    840
tcccggaccc ctgaggtcac atgcgtggtg gtggacgtga gccacgaaga ccctgaggtc    900
aagttcaact ggtacgtgga cggcgtggag gtgcataatg ccaagacaaa gccgcgggag    960
gagcagtaca acagcacgta ccgtgtggtc agcgtcctca ccgtcctgca ccaggactgg   1020
ctgaatggca aggagtacaa gtgcaaggtc tccaacaaag ccctcccagc ccccatcgag   1080

```
aaaaccatct ccaaagccaa agggcagccc cgagaaccac aggtgtacac cctgcccca      1140 tcccgggagg agatgaccaa gaaccaggtc agcctgacct gcctggtcaa aggcttctat      1200
cccagcgaca tcgccgtgga gtgggagagc aatgggcagc cggagaacaa ctacaagacc      1260
acgcctcccg tgctggactc cgacggctcc ttcttcctct atagcaagct caccgtggac      1320
aagagcaggt ggcagcaggg gaacgtcttc tcatgctccg tgatgcatga ggctctgcac      1380
aaccactaca cgcagaagag cctctccctg tctccgggta aa                        1422
```

<210> SEQ ID NO 14
<211> LENGTH: 474
<212> TYPE: PRT
<213> ORGANISM: Homo sapiens

<400> SEQUENCE: 14

```
Met Glu Leu Gly Leu Ser Trp Val Phe Leu Val Ala Leu Leu Arg Gly
1               5                   10                  15

Val Gln Cys Gln Val Gln Leu Val Glu Ser Gly Gly Gly Val Ile Gln
            20                  25                  30

Pro Gly Arg Ser Leu Arg Leu Ser Cys Val Ala Ser Lys Phe Ile Phe
        35                  40                  45

Ser Asn His Gly Ile His Trp Val Arg Gln Ala Pro Gly Lys Gly Leu
    50                  55                  60

Glu Trp Val Ala Val Ile Ser Lys Asp Gly Thr Asn Ala His Tyr Ala
65                  70                  75                  80

Asp Ser Val Arg Gly Arg Phe Ser Ile Ser Arg Asp Asn Ser Lys Asp
                85                  90                  95

Thr Val Phe Leu Glu Met Arg Ser Leu Arg Pro Glu Asp Thr Ala Val
            100                 105                 110

Tyr Tyr Cys Ala Arg Glu Gly Arg Cys Ile Glu Glu Asn Cys Tyr Ser
        115                 120                 125

Gly Gln Ile Asp Tyr Trp Gly Gln Gly Ser Leu Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
```

```
                305                 310                 315                 320
Glu Gln Tyr Asn Ser Thr Tyr Arg Val Val Ser Val Leu Thr Val Leu
                    325                 330                 335

His Gln Asp Trp Leu Asn Gly Lys Glu Tyr Lys Cys Lys Val Ser Asn
                340                 345                 350

Lys Ala Leu Pro Ala Pro Ile Glu Lys Thr Ile Ser Lys Ala Lys Gly
            355                 360                 365

Gln Pro Arg Glu Pro Gln Val Tyr Thr Leu Pro Pro Ser Arg Glu Glu
        370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 15
<211> LENGTH: 705
<212> TYPE: DNA
<213> ORGANISM: Homo sapiens

<400> SEQUENCE: 15
atggaagccc cagcgcagct tctcttcctc ctgctactct ggctcccaga taccaccgga      60
gaaattctat tgacacagtc tccagccacc ctgtctttgt ctccagggga agagccacc     120 ctctcctgca gggccagtca gagtgttggc aggtacatgg cctggtatca acagagacct    180
ggccaggctc ccaggctcct catctatgat gcatccatca gggccactgg catcccagcc    240
aggttcagtg gcagtgggtc tgggacagac ttcactctca ccatcagcag cctacagcct    300
gaagattttg caatttatta ctgtcagcag cgtagcagct ggccccgct cactttcggc     360 ggagggacca aggttgagat caaacgtacg gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca agcagactac gagaaacac aaagtctacg cctgcgaagt cacccatcag    660
ggcctgagct cgcccgtcac aaagagcttc aacagggag agtgt                      705

<210> SEQ ID NO 16
<211> LENGTH: 235
<212> TYPE: PRT
<213> ORGANISM: Homo sapiens

<400> SEQUENCE: 16

Met Glu Ala Pro Ala Gln Leu Leu Phe Leu Leu Leu Leu Trp Leu Pro
1               5                   10                  15

Asp Thr Thr Gly Glu Ile Leu Leu Thr Gln Ser Pro Ala Thr Leu Ser
            20                  25                  30

Leu Ser Pro Gly Glu Arg Ala Thr Leu Ser Cys Arg Ala Ser Gln Ser
```

|  |  | 35 |  |  |  | 40 |  |  |  | 45 |  |  |
|---|---|---|---|---|---|---|---|---|---|---|---|---|

Val Gly Arg Tyr Met Ala Trp Tyr Gln Gln Arg Pro Gly Gln Ala Pro
 50                      55                      60

Arg Leu Leu Ile Tyr Asp Ala Ser Ile Arg Ala Thr Gly Ile Pro Ala
 65                   70                      75                  80

Arg Phe Ser Gly Ser Gly Ser Gly Thr Asp Phe Thr Leu Thr Ile Ser
                 85                       90                   95

Ser Leu Gln Pro Glu Asp Phe Ala Ile Tyr Tyr Cys Gln Gln Arg Ser
             100                     105                 110

Ser Trp Pro Pro Leu Thr Phe Gly Gly Gly Thr Lys Val Glu Ile Lys
         115                     120                 125

Arg Thr Val Ala Ala Pro Ser Val Phe Ile Phe Pro Pro Ser Asp Glu
 130                     135                     140

Gln Leu Lys Ser Gly Thr Ala Ser Val Val Cys Leu Leu Asn Asn Phe
145                     150                     155                 160

Tyr Pro Arg Glu Ala Lys Val Gln Trp Lys Val Asp Asn Ala Leu Gln
                 165                     170                 175

Ser Gly Asn Ser Gln Glu Ser Val Thr Glu Gln Asp Ser Lys Asp Ser
             180                     185                 190

Thr Tyr Ser Leu Ser Ser Thr Leu Thr Leu Ser Lys Ala Asp Tyr Glu
         195                     200                 205

Lys His Lys Val Tyr Ala Cys Glu Val Thr His Gln Gly Leu Ser Ser
 210                     215                     220

Pro Val Thr Lys Ser Phe Asn Arg Gly Glu Cys
225                     230                     235

<210> SEQ ID NO 17
<211> LENGTH: 1422
<212> TYPE: DNA
<213> ORGANISM: Homo sapiens

<400> SEQUENCE: 17

| atggagttgg ggctgcgctg ggttttcctc gttgctcttt taagaggtgt ccagtgtcag | 60 |
|---|---|
| gtgcagctgg tggagtcggg gggaggcgtg atccagcctg gaggtccct gagactctcc | 120 |
| tgtgttgcct ctaaattcat cttcagtaac catggcatac actgggtccg ccaggctcca | 180 |
| ggcaaggggc tggagtgggt ggcggttata tcaaaggatg gactaatgc acactacgca | 240 |
| gactccgtga ggggccgatt tagcatctcc agagacaact ccaaggacac tgtctttctg | 300 |
| gaaatgcgca gcctgcgacc tgaagacacg gctgtctatt actgtgcgag agagggccgg | 360 |
| tgtattgaag aaaagtgcta ctccggacag attgactatt gggggcaggg atccctggtc | 420 |
| accgtctcga gcgcctccac caagggccca tcggtcttcc ccctggcacc ctcctccaag | 480 |
| agcacctctg ggggcacagc ggccctgggc tgcctggtca aggactactt ccccgaaccg | 540 |
| gtgacggtgt cgtggaactc aggcgccctg accagcggcg tgcacacctt cccggctgtc | 600 |
| ctacagtcct caggactcta ctccctcagc agcgtggtga ccgtgccctc agcagcttg | 660 |
| ggcacccaga cctacatctg caacgtgaat cacaagccca gcaacaccaa ggtggacaag | 720 |
| agagttgagc ccaaatcttg tgacaaaact cacacatgcc caccgtgccc agcacctgaa | 780 |
| ctcctggggg gaccgtcagt cttcctcttc cccccaaaac ccaaggacac cctcatgatc | 840 |
| tcccggaccc ctgaggtcac atgcgtggtg gtggacgtga gccacgaaga ccctgaggtc | 900 |
| aagttcaact ggtacgtgga cggcgtggag gtgcataatg ccaagacaaa gccgcgggag | 960 |
| gagcagtaca acagcacgta ccgtgtggtc agcgtcctca ccgtcctgca ccaggactgg | 1020 |

```
ctgaatggca aggagtacaa gtgcaaggtc tccaacaaag ccctcccagc ccccatcgag    1080
aaaaccatct ccaaagccaa agggcagccc cgagaaccac aggtgtacac cctgccccca    1140
tcccgggagg agatgaccaa gaaccaggtc agcctgacct gcctggtcaa aggcttctat    1200
cccagcgaca tcgccgtgga gtgggagagc aatgggcagc cggagaacaa ctacaagacc    1260
acgcctcccg tgctggactc cgacggctcc ttcttcctct atagcaagct caccgtggac    1320
aagagcaggt ggcagcaggg gaacgtcttc tcatgctccg tgatgcatga ggctctgcac    1380
aaccactaca cgcagaagag cctctccctg tctccgggta aa                      1422
```

<210> SEQ ID NO 18  
<211> LENGTH: 474  
<212> TYPE: PRT  
<213> ORGANISM: Homo sapiens

<400> SEQUENCE: 18

```
Met Glu Leu Gly Leu Arg Trp Val Phe Leu Val Ala Leu Leu Arg Gly
1               5                   10                  15

Val Gln Cys Gln Val Gln Leu Val Glu Ser Gly Gly Gly Val Ile Gln
                20                  25                  30

Pro Gly Arg Ser Leu Arg Leu Ser Cys Val Ala Ser Lys Phe Ile Phe
            35                  40                  45

Ser Asn His Gly Ile His Trp Val Arg Gln Ala Pro Gly Lys Gly Leu
        50                  55                  60

Glu Trp Val Ala Val Ile Ser Lys Asp Gly Thr Asn Ala His Tyr Ala
65                  70                  75                  80

Asp Ser Val Arg Gly Arg Phe Ser Ile Ser Arg Asp Asn Ser Lys Asp
                85                  90                  95

Thr Val Phe Leu Glu Met Arg Ser Leu Arg Pro Glu Asp Thr Ala Val
            100                 105                 110

Tyr Tyr Cys Ala Arg Glu Gly Arg Cys Ile Glu Glu Lys Cys Tyr Ser
        115                 120                 125

Gly Gln Ile Asp Tyr Trp Gly Gln Gly Ser Leu Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300
```

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
            325                 330                 335

His Gln Asp Trp Leu Asn Gly Lys Glu Tyr Lys Cys Lys Val Ser Asn
        340                 345                 350

Lys Ala Leu Pro Ala Pro Ile Glu Lys Thr Ile Ser Lys Ala Lys Gly
    355                 360                 365

Gln Pro Arg Glu Pro Gln Val Tyr Thr Leu Pro Pro Ser Arg Glu Glu
370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
            405                 410                 415

Asn Tyr Lys Thr Thr Pro Pro Val Leu Asp Ser Asp Gly Ser Phe Phe
        420                 425                 430

Leu Tyr Ser Lys Leu Thr Val Asp Lys Ser Arg Trp Gln Gln Gly Asn
    435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 19
<211> LENGTH: 705
<212> TYPE: DNA
<213> ORGANISM: Homo sapiens

<400> SEQUENCE: 19
atggaagccc cagcgcagct tctcttcctc ctgctactct ggctcccaga taccaccgga      60
gaaattctat tgacacagtc tccagccacc ctgtctttgt ctccagggga aagagccacc     120
ctctcctgca gggccagtca gagtgttggc aggtacatgg cctggtatca acagagacct     180
ggccaggctc ccaggctcct catctatgat gcatccatca gggccactgg catcccagcc     240
aggttcagtg gcagtgggtc tgggacagac ttcactctca ccatcagcag cctacagact     300
gaagattttg caatttatta ctgtcagcag cgtagcagct ggccccccgct cactttcggc     360 ggagggacca aggttgagat caaacgtacg gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag gacagcacct acagcctcag cagcaccctg     600
acgctgagca aagcagacta cgagaaacac aaagtctacg cctgcgaagt cacccatcag     660
ggcctgagct cgcccgtcac aaagagcttc aacaggggag agtgt                     705

<210> SEQ ID NO 20
<211> LENGTH: 235
<212> TYPE: PRT
<213> ORGANISM: Homo sapiens

<400> SEQUENCE: 20

Met Glu Ala Pro Ala Gln Leu Leu Phe Leu Leu Leu Leu Trp Leu Pro
1               5                   10                  15

Asp Thr Thr Gly Glu Ile Leu Leu Thr Gln Ser Pro Ala Thr Leu Ser
            20                  25                  30

Leu Ser Pro Gly Glu Arg Ala Thr Leu Ser Cys Arg Ala Ser Gln Ser
            35                  40                  45

Val Gly Arg Tyr Met Ala Trp Tyr Gln Gln Arg Pro Gly Gln Ala Pro
 50                  55                  60

Arg Leu Leu Ile Tyr Asp Ala Ser Ile Arg Ala Thr Gly Ile Pro Ala
 65                  70                  75                  80

Arg Phe Ser Gly Ser Gly Ser Gly Thr Asp Phe Thr Leu Thr Ile Ser
                85                  90                  95

Ser Leu Gln Thr Glu Asp Phe Ala Ile Tyr Tyr Cys Gln Gln Arg Ser
            100                 105                 110

Ser Trp Pro Pro Leu Thr Phe Gly Gly Gly Thr Lys Val Glu Ile Lys
            115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
            195                 200                 205

Lys His Lys Val Tyr Ala Cys Glu Val Thr His Gln Gly Leu Ser Ser
        210                 215                 220

Pro Val Thr Lys Ser Phe Asn Arg Gly Glu Cys
225                 230                 235

<210> SEQ ID NO 21
<211> LENGTH: 1422
<212> TYPE: DNA
<213> ORGANISM: Homo sapiens

<400> SEQUENCE: 21
atggagttgg ggctgtgctg ggttttcctc gttgctcttt taagaggtgt ccagtgtcag     60
gtgcagctgg tggactctgg gggaggcgtg gtccagcctg gaggtccct gagactctcc    120 tgtgcagcct ctggactcac cttcagtgat tatggtatgc actgggtccg ccaggctcca    180 ggcaagggc tggagtgggt ggcagtcatc tcaaaggatg aactaacac acactatgca     240 gactccgtga ggcccgatt caccatctcc agagacaact ccaagaacat tttctatctg    300
caaatgaacg gcctgagagc tgaggacacg gctgtctatt acagtgggag agatgggaag    360
tgtcctgatc ttaagtgcta ctcagggttg attgactact ggggccaggg gaccctggtc    420
accgtctcga gcgcctccac caagggccca tcggtcttcc ccctggcacc ctcctccaag    480
agcacctctg gggcacagc ggccctgggc tgcctggtca aggactactt ccccgaaccg     540
gtgacggtgt cgtggaactc aggcgccctg accagcggcg tgcacacctt ccggctgtc    600 ctacagtcct caggactcta ctccctcagc agcgtggtga ccgtgccctc agcagcttg    660 ggcacccaga cctacatctg caacgtgaat cacaagccca gcaacaccaa ggtggacaag    720
agagttgagc ccaaatcttg tgacaaaact cacacatgcc caccgtgccc agcacctgaa    780
ctcctggggg gaccgtcagt cttcctcttc cccccaaaac ccaaggacac cctcatgatc    840
tcccggaccc ctgaggtcac atgcgtggtg gtggacgtga gccacgaaga ccctgaggtc    900
aagttcaact ggtacgtgga cggcgtggag gtgcataatg ccaagacaaa gccgcgggag    960

```
gagcagtaca acagcacgta ccgtgtggtc agcgtcctca ccgtcctgca ccaggactgg    1020
ctgaatggca aggagtacaa gtgcaaggtc tccaacaaag ccctcccagc ccccatcgag    1080
aaaaccatct ccaaagccaa agggcagccc cgagaaccac aggtgtacac cctgccccca    1140
tcccgggagg agatgaccaa gaaccaggtc agcctgacct gcctggtcaa aggcttctat    1200
cccagcgaca tcgccgtgga gtgggagagc aatgggcagc cggagaacaa ctacaagacc    1260
acgcctcccg tgctggactc cgacggctcc ttcttcctct atagcaagct caccgtggac    1320
aagagcaggt ggcagcaggg gaacgtcttc tcatgctccg tgatgcatga ggctctgcac    1380
aaccactaca cgcagaagag cctctccctg tctccgggta aa                       1422
```

<210> SEQ ID NO 22
<211> LENGTH: 474
<212> TYPE: PRT
<213> ORGANISM: Homo sapiens

<400> SEQUENCE: 22

```
Met Glu Leu Gly Leu Cys Trp Val Phe Leu Val Ala Leu Leu Arg Gly
1               5                   10                  15

Val Gln Cys Gln Val Gln Leu Val Asp Ser Gly Gly Gly Val Val Gln
            20                  25                  30

Pro Gly Arg Ser Leu Arg Leu Ser Cys Ala Ala Ser Gly Leu Thr Phe
        35                  40                  45

Ser Asp Tyr Gly Met His Trp Val Arg Gln Ala Pro Gly Lys Gly Leu
    50                  55                  60

Glu Trp Val Ala Val Ile Ser Lys Asp Gly Thr Asn Thr His Tyr Ala
65                  70                  75                  80

Asp Ser Val Arg Gly Arg Phe Thr Ile Ser Arg Asp Asn Ser Lys Asn
                85                  90                  95

Ile Phe Tyr Leu Gln Met Asn Gly Leu Arg Ala Glu Asp Thr Ala Val
            100                 105                 110

Tyr Tyr Ser Gly Arg Asp Gly Lys Cys Pro Asp Leu Lys Cys Tyr Ser
        115                 120                 125

Gly Leu Ile Asp Tyr Trp Gly Gln Gly Thr Leu Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285
```

Val Val Val Asp Val Ser His Glu Asp Pro Glu Val Lys Phe Asn Trp
            290                 295                 300
Tyr Val Asp Gly Val Glu Val His Asn Ala Lys Thr Lys Pro Arg Glu
305                 310                 315                 320
Glu Gln Tyr Asn Ser Thr Tyr Arg Val Val Ser Val Leu Thr Val Leu
                325                 330                 335
His Gln Asp Trp Leu Asn Gly Lys Glu Tyr Lys Cys Lys Val Ser Asn
            340                 345                 350
Lys Ala Leu Pro Ala Pro Ile Glu Lys Thr Ile Ser Lys Ala Lys Gly
            355                 360                 365
Gln Pro Arg Glu Pro Gln Val Tyr Thr Leu Pro Pro Ser Arg Glu Glu
370                 375                 380
Met Thr Lys Asn Gln Val Ser Leu Thr Cys Leu Val Lys Gly Phe Tyr
385                 390                 395                 400
Pro Ser Asp Ile Ala Val Glu Trp Glu Ser Asn Gly Gln Pro Glu Asn
                405                 410                 415
Asn Tyr Lys Thr Thr Pro Pro Val Leu Asp Ser Asp Gly Ser Phe Phe
            420                 425                 430
Leu Tyr Ser Lys Leu Thr Val Asp Lys Ser Arg Trp Gln Gln Gly Asn
            435                 440                 445
Val Phe Ser Cys Ser Val Met His Glu Ala Leu His Asn His Tyr Thr
450                 455                 460
Gln Lys Ser Leu Ser Leu Ser Pro Gly Lys
465                 470

<210> SEQ ID NO 23
<211> LENGTH: 705
<212> TYPE: DNA
<213> ORGANISM: Homo sapiens

<400> SEQUENCE: 23
atggaagccc cagcgcagct tctcttcctc ctgctactct ggctcccaga taccaccgga      60
gaaattgtgt tgacacagtc tccggccacc ctgtctttgt ctccagggga agagccacc     120
ctctcctgca gggccagtca gagtgttggc ggctacttag cctggtacca acagaagcct     180
ggccaggctc ccaggctcct catctatgat gcatccaaaa gggccactgg catcccagcc     240
aggttcagtg gcagtgggtc tgggacagac ttcactctca ccatcagcac cctagagcct     300
gaagattttg caatttatta ctgtcaccag cgtagcagct ggcctccgct cactttcggc     360
ggagggacca aggtggatat caaacgtacg gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg ccctccaatc gggtaactcc     540
caggagagtg tcacagagca ggacagcaag acagcacct acagcctcag cagcccctg     600
acgctgagca aagcagacta cgagaaacac aaagtctacg cctgcgaagt cacccatcag     660
ggcctgagct cgcccgtcac aaagagcttc aacaggggag agtgt                    705

<210> SEQ ID NO 24
<211> LENGTH: 235
<212> TYPE: PRT
<213> ORGANISM: Homo sapiens

<400> SEQUENCE: 24

Met Glu Ala Pro Ala Gln Leu Leu Phe Leu Leu Leu Leu Trp Leu Pro
1               5                   10                  15

```
Asp Thr Thr Gly Glu Ile Val Leu Thr Gln Ser Pro Ala Thr Leu Ser
             20                  25                  30

Leu Ser Pro Gly Glu Arg Ala Thr Leu Ser Cys Arg Ala Ser Gln Ser
         35                  40                  45

Val Gly Gly Tyr Leu Ala Trp Tyr Gln Gln Lys Pro Gly Gln Ala Pro
     50                  55                  60

Arg Leu Leu Ile Tyr Asp Ala Ser Lys Arg Ala Thr Gly Ile Pro Ala
 65                  70                  75                  80

Arg Phe Ser Gly Ser Gly Ser Gly Thr Asp Phe Thr Leu Thr Ile Ser
                 85                  90                  95

Thr Leu Glu Pro Glu Asp Phe Ala Ile Tyr Tyr Cys His Gln Arg Ser
             100                 105                 110

Ser Trp Pro Pro Leu Thr Phe Gly Gly Gly Thr Lys Val Asp Ile Lys
         115                 120                 125

Arg Thr Val Ala Ala Pro Ser Val Phe Ile Phe Pro Pro Ser Asp Glu
     130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                 165                 170                 175

Ser Gly Asn Ser Gln Glu Ser Val Thr Glu Gln Asp Ser Lys Asp Ser
             180                 185                 190

Thr Tyr Ser Leu Ser Ser Thr Leu Thr Leu Ser Lys Ala Asp Tyr Glu
         195                 200                 205

Lys His Lys Val Tyr Ala Cys Glu Val Thr His Gln Gly Leu Ser Ser
     210                 215                 220

Pro Val Thr Lys Ser Phe Asn Arg Gly Glu Cys
225                 230                 235

<210> SEQ ID NO 25
<211> LENGTH: 54
<212> TYPE: PRT
<213> ORGANISM: Human Cytometalovirus

<400> SEQUENCE: 25

Val Ser His Thr Ala Asn Glu Thr Ile Tyr Asn Thr Thr Leu Lys Tyr
 1               5                  10                  15

Gly Asp Val Val Gly Val Asn Thr Thr Lys Tyr Pro Tyr Arg Val Cys
             20                  25                  30

Ser Met Ala Gln Gly Thr Asp Leu Ile Arg Phe Glu Arg Asn Ile Val
         35                  40                  45

Cys Thr Pro Met Lys Pro
     50

<210> SEQ ID NO 26
<211> LENGTH: 54
<212> TYPE: PRT
<213> ORGANISM: Human Cytomegalovirus

<400> SEQUENCE: 26

Val Ser His Thr Ala Asn Glu Thr Ile Tyr Asn Thr Thr Leu Lys Tyr
 1               5                  10                  15

Gly Asp Val Val Gly Val Asn Thr Thr Lys Tyr Pro Tyr Arg Val Cys
             20                  25                  30

Ser Met Ala Gln Gly Thr Asp Leu Ile Arg Phe Glu Arg Asn Ile Val
         35                  40                  45
```

Cys Thr Pro Met Lys Pro
    50

<210> SEQ ID NO 27
<211> LENGTH: 54
<212> TYPE: PRT
<213> ORGANISM: Human Cytomegalovirus

<400> SEQUENCE: 27

Val Ser His Gly Val Asn Glu Thr Ile Tyr Asn Thr Thr Leu Lys Tyr
1               5                   10                  15

Gly Asp Val Val Gly Val Asn Thr Thr Lys Tyr Pro Tyr Arg Val Cys
            20                  25                  30

Ser Met Ala Gln Gly Thr Asp Leu Ile Arg Phe Glu Arg Asn Ile Val
        35                  40                  45

Cys Thr Ser Met Lys Pro
    50

<210> SEQ ID NO 28
<211> LENGTH: 54
<212> TYPE: PRT
<213> ORGANISM: Human Cytomegalovirus

<400> SEQUENCE: 28

Val Ser His Arg Ala Asn Glu Thr Ile Tyr Asn Thr Thr Leu Lys Tyr
1               5                   10                  15

Gly Asp Val Val Gly Val Asn Thr Thr Lys Tyr Pro Tyr Arg Val Cys
            20                  25                  30

Ser Met Ala Gln Gly Thr Asp Leu Ile Arg Phe Asp Arg Asn Ile Val
        35                  40                  45

Cys Thr Pro Met Lys Pro
    50

<210> SEQ ID NO 29
<211> LENGTH: 47
<212> TYPE: PRT
<213> ORGANISM: Guinea Pig Cytomegalovirus

<400> SEQUENCE: 29

Ser Arg Asn Asn Thr Val Ile Arg Asn Leu Thr Ala Ser Val Asp Phe
1               5                   10                  15

Ser Gln Arg Lys Leu Tyr Arg Ile Cys Ser Met Ser Met Gly Thr Asp
            20                  25                  30

Leu Val Arg Phe Ala Arg Thr Ile Gln Cys Val Pro Phe Asn Pro
        35                  40                  45

<210> SEQ ID NO 30
<211> LENGTH: 54
<212> TYPE: PRT
<213> ORGANISM: Artificial Sequence
<220> FEATURE:
<223> OTHER INFORMATION: Consensus sequence of SEQ ID NOs: 25-29

<400> SEQUENCE: 30

Val Ser His Arg Ala Asn Glu Thr Ile Tyr Asn Thr Thr Leu Lys Tyr
1               5                   10                  15

Gly Asp Val Val Gly Val Asn Thr Thr Lys Tyr Pro Tyr Arg Val Cys
            20                  25                  30

Ser Met Ala Gln Gly Thr Asp Leu Ile Arg Phe Glu Arg Asn Ile Val
        35                  40                  45

```
Cys Thr Pro Met Lys Pro
    50

<210> SEQ ID NO 31
<211> LENGTH: 25
<212> TYPE: PRT
<213> ORGANISM: Homo sapiens

<400> SEQUENCE: 31

Ser His Arg Ala Asn Glu Thr Ile Tyr Asn Thr Thr Leu Lys Tyr Gly
1               5                   10                  15

Asp Thr Thr Gly Thr Asn Thr Thr Lys
            20                  25

<210> SEQ ID NO 32
<211> LENGTH: 18
<212> TYPE: PRT
<213> ORGANISM: Homo sapiens

<400> SEQUENCE: 32

Asn Glu Thr Ile Tyr Asn Thr Thr Leu Lys Tyr Gly Asp Val Val Gly
1               5                   10                  15

Val Asn

<210> SEQ ID NO 33
<211> LENGTH: 16
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (3)..(3)
<223> OTHER INFORMATION: wherein the amino acid is Y or R
<220> FEATURE:
<221> NAME/KEY: VARIANT
<222> LOCATION: (5)..(5)
<223> OTHER INFORMATION: wherein the amino acid is T or L
<220> FEATURE:
<221> NAME/KEY: VARIANT
<222> LOCATION: (7)..(7)
<223> OTHER INFORMATION: wherein the amino acid is L or A
<220> FEATURE:
<221> NAME/KEY: VARIANT
<222> LOCATION: (8)..(8)
<223> OTHER INFORMATION: wherein the amino acid is K or S
<220> FEATURE:
<221> NAME/KEY: VARIANT
<222> LOCATION: (9)..(9)
<223> OTHER INFORMATION: wherein the amino acid is Y or V
<220> FEATURE:
<221> NAME/KEY: VARIANT
<222> LOCATION: (10)..(10)
<223> OTHER INFORMATION: wherein the amino acid is G or D
<220> FEATURE:
<221> NAME/KEY: VARIANT
<222> LOCATION: (11)..(11)
<223> OTHER INFORMATION: wherein the amino acid is D or F
<220> FEATURE:
<221> NAME/KEY: VARIANT
<222> LOCATION: (12)..(12)
<223> OTHER INFORMATION: wherein the amino acid is V or S
<220> FEATURE:
<221> NAME/KEY: VARIANT
<222> LOCATION: (13)..(13)
<223> OTHER INFORMATION: wherein the amino acid is V or Q
<220> FEATURE:
<221> NAME/KEY: VARIANT
<222> LOCATION: (14)..(14)
<223> OTHER INFORMATION: wherein the amino acid is G or none
<220> FEATURE:
<221> NAME/KEY: VARIANT
```

```
<222> LOCATION: (15)..(15)
<223> OTHER INFORMATION: wherein the amino acid is V or none
<220> FEATURE:
<221> NAME/KEY: VARIANT
<222> LOCATION: (16)..(16)
<223> OTHER INFORMATION: wherein the amino acid is N or none

<400> SEQUENCE: 33

Asn Ile Xaa Asn Xaa Thr Xaa Xaa Xaa Xaa Xaa Xaa Xaa Xaa Xaa
1               5                   10                  15

<210> SEQ ID NO 34
<211> LENGTH: 372
<212> TYPE: DNA
<213> ORGANISM: Homo sapiens

<400> SEQUENCE: 34
caggtacatc tggtggagtc gggggaggc gtcgtccagc ctggtagggc cctgagactc       60
tcctgtgcag ccactggatt cacatttagt aatcacggca tacattgggt ccgccaggct     120
ccaggcaagg ggctggagtg gctggcagtt atttcaagcg atggagatga tgaccgttac     180
gcagactccg tgaagggtcg attcagcgtc tccagagaca attccaagaa caccgtgcat     240
ctgcagatga atggcctgag acctgacgac acggctattt atttctgtgc gcgagatggg     300
aggtgtggtg aacctaagtg ctactcaggg ttgcctgatt actggggccg ggggaccctg     360
gtcaccgtct cg                                                        372

<210> SEQ ID NO 35
<211> LENGTH: 124
<212> TYPE: PRT
<213> ORGANISM: Homo sapiens

<400> SEQUENCE: 35

Gln Val His Leu Val Glu Ser Gly Gly Gly Val Val Gln Pro Gly Arg
1               5                   10                  15

Ala Leu Arg Leu Ser Cys Ala Ala Thr Gly Phe Thr Phe Ser Asn His
            20                  25                  30

Gly Ile His Trp Val Arg Gln Ala Pro Gly Lys Gly Leu Glu Trp Leu
        35                  40                  45

Ala Val Ile Ser Ser Asp Gly Asp Asp Arg Tyr Ala Asp Ser Val
    50                  55                  60

Lys Gly Arg Phe Ser Val Ser Arg Asp Asn Ser Lys Asn Thr Val His
65                  70                  75                  80

Leu Gln Met Asn Gly Leu Arg Pro Asp Asp Thr Ala Ile Tyr Phe Cys
                85                  90                  95

Ala Arg Asp Gly Arg Cys Gly Glu Pro Lys Cys Tyr Ser Gly Leu Pro
            100                 105                 110

Asp Tyr Trp Gly Arg Gly Thr Leu Val Thr Val Ser
        115                 120

<210> SEQ ID NO 36
<211> LENGTH: 6
<212> TYPE: PRT
<213> ORGANISM: Homo sapiens

<400> SEQUENCE: 36

Ser Asn His Gly Ile His
1               5

<210> SEQ ID NO 37
```

```
<211> LENGTH: 17
<212> TYPE: PRT
<213> ORGANISM: Homo sapiens

<400> SEQUENCE: 37

Val Ile Ser Ser Asp Gly Asp Asp Asp Arg Tyr Ala Asp Ser Val Lys
1               5                   10                  15
Gly

<210> SEQ ID NO 38
<211> LENGTH: 16
<212> TYPE: PRT
<213> ORGANISM: Homo sapiens

<400> SEQUENCE: 38

Asp Gly Arg Cys Gly Glu Pro Lys Cys Tyr Ser Gly Leu Pro Asp Tyr
1               5                   10                  15

<210> SEQ ID NO 39
<211> LENGTH: 6
<212> TYPE: PRT
<213> ORGANISM: Homo sapiens

<400> SEQUENCE: 39

Gly Phe Thr Phe Ser Asn
1               5

<210> SEQ ID NO 40
<211> LENGTH: 10
<212> TYPE: PRT
<213> ORGANISM: Homo sapiens

<400> SEQUENCE: 40

Val Ile Ser Ser Asp Gly Asp Asp Asp Arg
1               5                   10

<210> SEQ ID NO 41
<211> LENGTH: 330
<212> TYPE: DNA
<213> ORGANISM: Homo sapiens

<400> SEQUENCE: 41
gagattgttt tgacacagtc tccagccacc ctgtctttgt ctccagggga cagagccacc      60
ctctcctgca gggccagtca gagtgttggc gggtacttag cctggtatca acaaaagcct     120
ggccaggctc ccaggctcct cctctatgat gcatccaaca gggccactgg catcccagcc     180
aggttcagtg gcagtgggtc tgggacagac ttcactctca ccatcagcag cctagagcct     240
gaagattttg cactttatta ctgtcttcag cgtaacacgt ggcctccgct cactttcggg     300
ggagggacca aggtggagat caaacgtacg                                      330

<210> SEQ ID NO 42
<211> LENGTH: 110
<212> TYPE: PRT
<213> ORGANISM: Homo sapiens

<400> SEQUENCE: 42

Glu Ile Val Leu Thr Gln Ser Pro Ala Thr Leu Ser Leu Ser Pro Gly
1               5                   10                  15

Asp Arg Ala Thr Leu Ser Cys Arg Ala Ser Gln Ser Val Gly Gly Tyr
            20                  25                  30

Leu Ala Trp Tyr Gln Gln Lys Pro Gly Gln Ala Pro Arg Leu Leu Leu
```

```
                35                  40                  45
Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Leu Tyr Tyr Cys Leu Gln Arg Asn Thr Trp Pro Pro
                 85                  90                  95

Leu Thr Phe Gly Gly Gly Thr Lys Val Glu Ile Lys Arg Thr
            100                 105                 110
```

<210> SEQ ID NO 43
<211> LENGTH: 11
<212> TYPE: PRT
<213> ORGANISM: Homo sapiens

<400> SEQUENCE: 43

```
Arg Ala Ser Gln Ser Val Gly Gly Tyr Leu Ala
 1               5                  10
```

<210> SEQ ID NO 44
<211> LENGTH: 7
<212> TYPE: PRT
<213> ORGANISM: Homo sapiens

<400> SEQUENCE: 44

```
Asp Ala Ser Asn Arg Ala Thr
 1               5
```

<210> SEQ ID NO 45
<211> LENGTH: 10
<212> TYPE: PRT
<213> ORGANISM: Homo sapiens

<400> SEQUENCE: 45

```
Leu Gln Arg Asn Thr Trp Pro Pro Leu Thr
 1               5                  10
```

<210> SEQ ID NO 46
<211> LENGTH: 372
<212> TYPE: DNA
<213> ORGANISM: Homo sapiens

<400> SEQUENCE: 46

```
caggtgcagc tggtggactc tgggggaggc atggtccagc ctggaggtc  cctgagactc       60
tcctgttcag cctctggact caccttcagc aattatggca tgcactgggt ccgccaggct      120
ccaggcaagg ggctggagtg ggtggcagtt atatcaagtg atggaagtaa tgagcactac      180
gcagactccg tgaagggccg attcactatc tccagagaca atttcaacaa catgctgtat      240
ctgcaaatga acagcctgag agctgaggac acggctgtct attacagtgc gagagatggg      300
aggtgtcctg atgttaactg ctactcaggg ttgattgact attggggcca ggggaccctg      360
gtcaccgtct cg                                                          372
```

<210> SEQ ID NO 47
<211> LENGTH: 124
<212> TYPE: PRT
<213> ORGANISM: Homo sapiens

<400> SEQUENCE: 47

```
Gln Val Gln Leu Val Asp Ser Gly Gly Gly Met Val Gln Pro Gly Arg
 1               5                  10                  15
```

```
Ser Leu Arg Leu Ser Cys Ser Ala Ser Gly Leu Thr Phe Ser Asn Tyr
        20                  25                  30

Gly Met His Trp Val Arg Gln Ala Pro Gly Lys Gly Leu Glu Trp Val
        35                  40                  45

Ala Val Ile Ser Ser Asp Gly Ser Asn Glu His Tyr Ala Asp Ser Val
    50                  55                  60

Lys Gly Arg Phe Thr Ile Ser Arg Asp Asn Phe Asn Asn Met Leu Tyr
65                  70                  75                  80

Leu Gln Met Asn Ser Leu Arg Ala Glu Asp Thr Ala Val Tyr Tyr Ser
                85                  90                  95

Ala Arg Asp Gly Arg Cys Pro Asp Val Asn Cys Tyr Ser Gly Leu Ile
            100                 105                 110

Asp Tyr Trp Gly Gln Gly Thr Leu Val Thr Val Ser
            115                 120
```

<210> SEQ ID NO 48
<211> LENGTH: 6
<212> TYPE: PRT
<213> ORGANISM: Homo sapiens

<400> SEQUENCE: 48

```
Ser Asn Tyr Gly Met His
1               5
```

<210> SEQ ID NO 49
<211> LENGTH: 17
<212> TYPE: PRT
<213> ORGANISM: Homo sapiens

<400> SEQUENCE: 49

```
Val Ile Ser Ser Asp Gly Ser Asn Glu His Tyr Ala Asp Ser Val Lys
1               5                   10                  15

Gly
```

<210> SEQ ID NO 50
<211> LENGTH: 16
<212> TYPE: PRT
<213> ORGANISM: Homo sapiens

<400> SEQUENCE: 50

```
Asp Gly Arg Cys Pro Asp Val Asn Cys Tyr Ser Gly Leu Ile Asp Tyr
1               5                   10                  15
```

<210> SEQ ID NO 51
<211> LENGTH: 10
<212> TYPE: PRT
<213> ORGANISM: Homo sapiens

<400> SEQUENCE: 51

```
Val Ile Ser Ser Asp Gly Ser Asn Glu His
1               5                   10
```

<210> SEQ ID NO 52
<211> LENGTH: 110
<212> TYPE: PRT
<213> ORGANISM: Homo sapiens

<400> SEQUENCE: 52

```
Glu Ile Val Leu Thr Gln Ser Pro Ala Thr Leu Ser Leu Ser Pro Gly
1               5                   10                  15
```

```
Glu Arg Ala Thr Leu Ser Cys Arg Ala Ser Gln Ser Val Gly Arg Tyr
            20                  25                  30

Leu Ala Trp Tyr Gln Gln Lys Gly Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Asp Ser Leu Glu Pro
65                  70                  75                  80

Glu Asp Phe Ala Val Tyr Tyr Cys Gln Gln Arg Ser Asn Trp Pro Pro
                85                  90                  95

Leu Thr Phe Gly Gly Gly Ser Lys Val Glu Ile Lys Arg Thr
            100                 105                 110
```

<210> SEQ ID NO 53
<211> LENGTH: 11
<212> TYPE: PRT
<213> ORGANISM: Homo sapiens

<400> SEQUENCE: 53

```
Arg Ala Ser Gln Ser Val Gly Arg Tyr Leu Ala
1               5                   10
```

<210> SEQ ID NO 54
<211> LENGTH: 10
<212> TYPE: PRT
<213> ORGANISM: Homo sapiens

<400> SEQUENCE: 54

```
Gln Gln Arg Ser Asn Trp Pro Pro Leu Thr
1               5                   10
```

<210> SEQ ID NO 55
<211> LENGTH: 372
<212> TYPE: DNA
<213> ORGANISM: Homo sapiens

<400> SEQUENCE: 55

```
caggtgcagc tggtggagtc tgggggaggc gtggtccagc ctggggaggtc cctgagactc    60
tcctgtgcag cctctggatt caccttcagt agtaatggca tacactgggt ccgccaggct   120
ccaggcaagg ggctggactg ggtggcagtt atatcatctg atgcaaatga taaacaatac   180
gcagactccg tgaagggccg attcaccatc tccagagaca attccaagaa catggtgtat   240
ctgcaaatga acagcctgag agttgaagac acggctgtct atttctgtgc gagagatggg   300
acgtgcagtg gtggtaactg ctactcaggg ttgattgact attggggccg gggaattctg   360
gtcaccgtct cg                                                      372
```

<210> SEQ ID NO 56
<211> LENGTH: 124
<212> TYPE: PRT
<213> ORGANISM: Homo sapiens

<400> SEQUENCE: 56

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Asn
            20                  25                  30

Gly Ile His Trp Val Arg Gln Ala Pro Gly Lys Gly Leu Asp Trp Val
        35                  40                  45
```

```
Ala Val Ile Ser Ser Asp Ala Asn Asp Lys Gln Tyr Ala Asp Ser Val
         50                  55                  60
Lys Gly Arg Phe Thr Ile Ser Arg Asp Asn Ser Lys Asn Met Val Tyr
 65                  70                  75                  80
Leu Gln Met Asn Ser Leu Arg Val Glu Asp Thr Ala Val Tyr Phe Cys
                 85                  90                  95
Ala Arg Asp Gly Thr Cys Ser Gly Gly Asn Cys Tyr Ser Gly Leu Ile
                100                 105                 110
Asp Tyr Trp Gly Arg Gly Ile Leu Val Thr Val Ser
            115                 120
```

<210> SEQ ID NO 57
<211> LENGTH: 6
<212> TYPE: PRT
<213> ORGANISM: Homo sapiens

<400> SEQUENCE: 57

```
Ser Ser Asn Gly Ile His
 1               5
```

<210> SEQ ID NO 58
<211> LENGTH: 17
<212> TYPE: PRT
<213> ORGANISM: Homo sapiens

<400> SEQUENCE: 58

```
Val Ile Ser Ser Asp Ala Asn Asp Lys Gln Tyr Ala Asp Ser Val Lys
 1               5                  10                  15
Gly
```

<210> SEQ ID NO 59
<211> LENGTH: 16
<212> TYPE: PRT
<213> ORGANISM: Homo sapiens

<400> SEQUENCE: 59

```
Asp Gly Thr Cys Ser Gly Gly Asn Cys Tyr Ser Gly Leu Ile Asp Tyr
 1               5                  10                  15
```

<210> SEQ ID NO 60
<211> LENGTH: 6
<212> TYPE: PRT
<213> ORGANISM: Homo sapiens

<400> SEQUENCE: 60

```
Gly Phe Thr Phe Ser Ser
 1               5
```

<210> SEQ ID NO 61
<211> LENGTH: 10
<212> TYPE: PRT
<213> ORGANISM: Homo sapiens

<400> SEQUENCE: 61

```
Val Ile Ser Ser Asp Ala Asn Asp Lys Gln
 1               5                  10
```

<210> SEQ ID NO 62
<211> LENGTH: 330
<212> TYPE: DNA
<213> ORGANISM: Homo sapiens

<400> SEQUENCE: 62

```
gaaattgtgt tgacacagtc tccagccacc ttgtctttgt ctccaggtga aagagccacc    60
ctctcctgca gggccagtca gagtgttggc ggctacttag cctggtacca acagaaacct   120
ggccaggctc ccaggctcct catctacgat gcctccatca gggccactgg catcccagcc   180
aggttcagtg gcagtgggtc tgggacagac ttcactctca ccatcagcag cctagagcct   240
gaagattttg cagtttatta ctgtcaccag cgtagcaact ggcctccgct cactttcggc   300
ggagggacca aggtggatat caaacgtacg                                    330
```

<210> SEQ ID NO 63
<211> LENGTH: 110
<212> TYPE: PRT
<213> ORGANISM: Homo sapiens

<400> SEQUENCE: 63

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Gly Tyr
            20                  25                  30

Leu Ala Trp Tyr Gln Gln Lys Pro Gly Gln Ala Pro Arg Leu Leu Ile
        35                  40                  45

Tyr Asp Ala Ser Ile Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys His Gln Arg Ser Asn Trp Pro Pro
                85                  90                  95

Leu Thr Phe Gly Gly Gly Thr Lys Val Asp Ile Lys Arg Thr
            100                 105                 110
```

<210> SEQ ID NO 64
<211> LENGTH: 6
<212> TYPE: PRT
<213> ORGANISM: Homo sapiens

<400> SEQUENCE: 64

```
Ala Ser Ile Arg Ala Thr
1               5
```

<210> SEQ ID NO 65
<211> LENGTH: 10
<212> TYPE: PRT
<213> ORGANISM: Homo sapiens

<400> SEQUENCE: 65

```
His Gln Arg Ser Asn Trp Pro Pro Leu Thr
1               5                   10
```

<210> SEQ ID NO 66
<211> LENGTH: 372
<212> TYPE: DNA
<213> ORGANISM: Homo sapiens

<400> SEQUENCE: 66

```
caggtgcagc tggtggagtc ggggggaggc gtgatccagc tgggaggtc cctgagactc     60 tcctgtgttg cctctaaatt catcttcagt aaccatggca tacactgggt ccgccaggct   120
ccaggcaagg ggctggagtg ggtggcggtt atatcaaaag atgggactaa tgcacactac   180
gcagactccg tgaggggccg atttagcatc tccagagaca actccaagga cactgtcttt   240
```

```
ctggaaatgc gcagcctgcg acctgaagac acggctgtgt attactgtgc gagagagggc        300
cggtgtattg aagaaaactg ctactccgga cagattgact attggggcca gggatccctg        360
gtcaccgtct cg                                                            372
```

```
<210> SEQ ID NO 67
<211> LENGTH: 124
<212> TYPE: PRT
<213> ORGANISM: Homo sapiens

<400> SEQUENCE: 67
```

Gln Val Gln Leu Val Glu Ser Gly Gly Val Ile Gln Pro Gly Arg
1               5                   10                  15

Ser Leu Arg Leu Ser Cys Val Ala Ser Lys Phe Ile Phe Ser Asn His
                20                  25                  30

Gly Ile His Trp Val Arg Gln Ala Pro Gly Lys Gly Leu Glu Trp Val
            35                  40                  45

Ala Val Ile Ser Lys Asp Gly Thr Asn Ala His Tyr Ala Asp Ser Val
        50                  55                  60

Arg Gly Arg Phe Ser Ile Ser Arg Asp Asn Ser Lys Asp Thr Val Phe
65                  70                  75                  80

Leu Glu Met Arg Ser Leu Arg Pro Glu Asp Thr Ala Val Tyr Tyr Cys
                85                  90                  95

Ala Arg Glu Gly Arg Cys Ile Glu Glu Asn Cys Tyr Ser Gly Gln Ile
                100                 105                 110

Asp Tyr Trp Gly Gln Gly Ser Leu Val Thr Val Ser
        115                 120

```
<210> SEQ ID NO 68
<211> LENGTH: 17
<212> TYPE: PRT
<213> ORGANISM: Homo sapiens

<400> SEQUENCE: 68
```

Val Ile Ser Lys Asp Gly Thr Asn Ala His Tyr Ala Asp Ser Val Arg
1               5                   10                  15

Gly

```
<210> SEQ ID NO 69
<211> LENGTH: 16
<212> TYPE: PRT
<213> ORGANISM: Homo sapiens

<400> SEQUENCE: 69
```

Glu Gly Arg Cys Ile Glu Glu Asn Cys Tyr Ser Gly Gln Ile Asp Tyr
1               5                   10                  15

```
<210> SEQ ID NO 70
<211> LENGTH: 6
<212> TYPE: PRT
<213> ORGANISM: Homo sapiens

<400> SEQUENCE: 70
```

Lys Phe Ile Phe Ser Asn
1               5

```
<210> SEQ ID NO 71
<211> LENGTH: 10
<212> TYPE: PRT
<213> ORGANISM: Homo sapiens
```

<400> SEQUENCE: 71

Val Ile Ser Lys Asp Gly Thr Asn Ala His
1               5                   10

<210> SEQ ID NO 72
<211> LENGTH: 330
<212> TYPE: DNA
<213> ORGANISM: Homo sapiens

<400> SEQUENCE: 72

```
gaaattctat tgacacagtc tccagccacc ctgtctttgt ctccagggga aagagccacc      60
ctctcctgca gggccagtca gagtgttggc aggtacatgg cctggtatca acagagacct     120
ggccaggctc ccaggctcct catctatgat gcatccatca gggccactgg catcccagcc     180
aggttcagtg gcagtgggtc tgggacagac ttcactctca ccatcagcag cctacagcct     240
gaagattttg caatttatta ctgtcagcag cgtagcagct ggccccgct cactttcggc      300
ggagggacca aggttgagat caaacgtacg                                      330
```

<210> SEQ ID NO 73
<211> LENGTH: 110
<212> TYPE: PRT
<213> ORGANISM: Homo sapiens

<400> SEQUENCE: 73

Glu Ile Leu Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Arg Tyr
            20                  25                  30

Met Ala Trp Tyr Gln Gln Arg Pro Gly Gln Ala Pro Arg Leu Leu Ile
        35                  40                  45

Tyr Asp Ala Ser Ile Arg Ala Thr Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Gln Gln Arg Ser Ser Trp Pro Pro
                85                  90                  95

Leu Thr Phe Gly Gly Gly Thr Lys Val Glu Ile Lys Arg Thr
            100                 105                 110

<210> SEQ ID NO 74
<211> LENGTH: 11
<212> TYPE: PRT
<213> ORGANISM: Homo sapiens

<400> SEQUENCE: 74

Arg Ala Ser Gln Ser Val Gly Arg Tyr Met Ala
1               5                   10

<210> SEQ ID NO 75
<211> LENGTH: 7
<212> TYPE: PRT
<213> ORGANISM: Homo sapiens

<400> SEQUENCE: 75

Asp Ala Ser Ile Arg Ala Thr
1               5

<210> SEQ ID NO 76

```
<211> LENGTH: 10
<212> TYPE: PRT
<213> ORGANISM: Homo sapiens

<400> SEQUENCE: 76

Gln Gln Arg Ser Ser Trp Pro Pro Leu Thr
1               5                   10

<210> SEQ ID NO 77
<211> LENGTH: 372
<212> TYPE: PRT
<213> ORGANISM: Homo sapiens

<400> SEQUENCE: 77

Cys Ala Gly Gly Thr Gly Cys Ala Gly Cys Thr Gly Thr Gly Gly
1               5                   10                  15

Ala Gly Thr Cys Gly Gly Gly Gly Gly Ala Gly Gly Cys Gly Thr
                20                  25                  30

Gly Ala Thr Cys Cys Ala Gly Cys Cys Thr Gly Gly Ala Gly Gly
                35                  40                  45

Thr Cys Cys Cys Thr Gly Ala Gly Ala Cys Thr Cys Thr Cys Thr
                50                  55                  60

Gly Thr Gly Thr Thr Gly Cys Cys Thr Cys Thr Ala Ala Thr Thr
65                  70                  75                  80

Cys Ala Thr Cys Thr Thr Cys Ala Gly Thr Ala Ala Cys Cys Ala
                85                  90                  95

Gly Gly Cys Ala Thr Ala Cys Ala Cys Thr Gly Gly Gly Thr Cys
                100                 105                 110

Gly Cys Cys Ala Gly Gly Cys Thr Cys Cys Ala Gly Gly Cys Ala
                115                 120                 125

Gly Gly Gly Gly Cys Thr Gly Gly Ala Gly Thr Gly Gly Thr Gly
                130                 135                 140

Gly Cys Gly Gly Thr Thr Ala Thr Ala Thr Cys Ala Ala Gly Gly
145                 150                 155                 160

Ala Thr Gly Gly Gly Ala Cys Thr Ala Ala Thr Gly Cys Ala Cys
                165                 170                 175

Cys Thr Ala Cys Gly Cys Ala Gly Ala Cys Thr Cys Cys Gly Thr
                180                 185                 190

Ala Gly Gly Gly Gly Cys Cys Gly Ala Thr Thr Cys Ala Cys Cys
                195                 200                 205

Thr Cys Thr Cys Cys Ala Gly Ala Gly Ala Cys Ala Ala Cys Thr
                210                 215                 220

Cys Ala Ala Gly Gly Ala Cys Ala Cys Gly Gly Cys Thr Thr Thr
225                 230                 235                 240

Cys Thr Gly Gly Ala Ala Thr Gly Cys Gly Cys Ala Gly Cys Cys
                245                 250                 255

Thr Gly Cys Gly Ala Cys Cys Thr Gly Ala Gly Ala Cys Ala Cys
                260                 265                 270

Gly Gly Cys Thr Gly Thr Cys Thr Ala Thr Ala Cys Thr Gly Thr
                275                 280                 285

Gly Cys Gly Ala Gly Ala Gly Ala Gly Cys Cys Gly Gly Thr
                290                 295                 300

Gly Thr Ala Thr Thr Gly Ala Ala Gly Ala Ala Ala Gly Thr Gly
305                 310                 315                 320

Cys Thr Ala Cys Thr Cys Cys Gly Gly Ala Cys Ala Gly Ala Thr
                325                 330                 335
```

```
Gly Ala Cys Thr Ala Thr Thr Gly Gly Gly Gly Cys Ala Gly Gly
                340                 345                 350

Gly Ala Thr Cys Cys Thr Gly Gly Thr Cys Ala Cys Cys Gly Thr
                355                 360                 365

Cys Thr Cys Gly
        370

<210> SEQ ID NO 78
<211> LENGTH: 124
<212> TYPE: PRT
<213> ORGANISM: Homo sapiens

<400> SEQUENCE: 78

Gln Val Gln Leu Val Glu Ser Gly Gly Val Ile Gln Pro Gly Arg
1               5                   10                  15

Ser Leu Arg Leu Ser Cys Val Ala Ser Lys Phe Ile Phe Ser Asn His
                20                  25                  30

Gly Ile His Trp Val Arg Gln Ala Pro Gly Lys Gly Leu Glu Trp Val
            35                  40                  45

Ala Val Ile Ser Lys Asp Gly Thr Asn Ala His Tyr Ala Asp Ser Val
    50                  55                  60

Arg Gly Arg Phe Ser Ile Ser Arg Asp Asn Ser Lys Asp Thr Val Phe
65                  70                  75                  80

Leu Glu Met Arg Ser Leu Arg Pro Glu Asp Thr Ala Val Tyr Tyr Cys
                85                  90                  95

Ala Arg Glu Gly Arg Cys Ile Glu Glu Lys Cys Tyr Ser Gly Gln Ile
                100                 105                 110

Asp Tyr Trp Gly Gln Gly Ser Leu Val Thr Val Ser
            115                 120

<210> SEQ ID NO 79
<211> LENGTH: 18
<212> TYPE: PRT
<213> ORGANISM: Homo sapiens

<400> SEQUENCE: 79

Val Ile Ser Lys Asp Gly Thr Asn Ala His Tyr Ala Asp Ser Val Arg
1               5                   10                  15

Gly Arg

<210> SEQ ID NO 80
<211> LENGTH: 16
<212> TYPE: PRT
<213> ORGANISM: Homo sapiens

<400> SEQUENCE: 80

Glu Gly Arg Cys Ile Glu Glu Lys Cys Tyr Ser Gly Gln Ile Asp Tyr
1               5                   10                  15

<210> SEQ ID NO 81
<211> LENGTH: 330
<212> TYPE: DNA
<213> ORGANISM: Homo sapiens

<400> SEQUENCE: 81
gaaattctat tgacacagtc tccagccacc ctgtctttgt ctccagggga aagagccacc    60
ctctcctgca gggccagtca gagtgttggc aggtacatgg cctggtatca acagagacct   120
ggccaggctc ccaggctcct catctatgat gcatccatca gggccactgg catcccagcc   180
```

```
aggttcagtg gcagtgggtc tgggacagac ttcactctca ccatcagcag cctacagact    240
gaagattttg caatttatta ctgtcagcag cgtagcagct ggccccccgct cactttcggc    300 ggagggacca aggttgagat caaacgtacg                                     330
```

<210> SEQ ID NO 82
<211> LENGTH: 110
<212> TYPE: PRT
<213> ORGANISM: Homo sapiens

<400> SEQUENCE: 82

```
Glu Ile Leu Leu Thr Gln Ser Pro Ala Thr Leu Ser Leu Ser Pro Gly
1               5                  10                   15

Glu Arg Ala Thr Leu Ser Cys Arg Ala Ser Gln Ser Val Gly Arg Tyr
            20                  25                  30

Met Ala Trp Tyr Gln Gln Arg Pro Gly Gln Ala Pro Arg Leu Leu Ile
        35                  40                  45

Tyr Asp Ala Ser Ile Arg Ala Thr Gly Ile Pro Ala Arg Phe Ser Gly
    50                  55                  60

Ser Gly Ser Gly Thr Asp Phe Thr Leu Thr Ile Ser Ser Leu Gln Thr
65                  70                  75                   80

Glu Asp Phe Ala Ile Tyr Tyr Cys Gln Gln Arg Ser Ser Trp Pro Pro
                85                  90                  95

Leu Thr Phe Gly Gly Gly Thr Lys Val Glu Ile Lys Arg Thr
            100                 105                 110
```

<210> SEQ ID NO 83
<211> LENGTH: 372
<212> TYPE: DNA
<213> ORGANISM: Homo sapiens

<400> SEQUENCE: 83

```
caggtgcagc tggtggactc tggggggaggc gtggtccagc ctgggaggtc cctgagactc     60
tcctgtgcag cctctggact caccttcagt gattatggta tgcactgggt ccgccaggct    120
ccaggcaagg gctggagtg gtggcagtc atctcaaagg atggaactaa cacacactat    180
gcagactccg tgaggggccg attcaccatc tccagagaca actccaagaa catttttctat    240 ctgcaaatga acggcctgag agctgaggac acggctgtct attacagtgg gagagatggg    300
aagtgtcctg atcttaagtg ctactcaggg ttgattgact actggggcca ggggaccctg    360
gtcaccgtct cg                                                       372
```

<210> SEQ ID NO 84
<211> LENGTH: 124
<212> TYPE: PRT
<213> ORGANISM: Homo sapiens

<400> SEQUENCE: 84

```
Gln Val Gln Leu Val Asp Ser Gly Gly Gly Val Val Gln Pro Gly Arg
1               5                  10                  15

Ser Leu Arg Leu Ser Cys Ala Ala Ser Gly Leu Thr Phe Ser Asp Tyr
            20                  25                  30

Gly Met His Trp Val Arg Gln Ala Pro Gly Lys Gly Leu Glu Trp Val
        35                  40                  45

Ala Val Ile Ser Lys Asp Gly Thr Asn Thr His Tyr Ala Asp Ser Val
    50                  55                  60

Arg Gly Arg Phe Thr Ile Ser Arg Asp Asn Ser Lys Asn Ile Phe Tyr
```

```
                65                  70                  75                  80
Leu Gln Met Asn Gly Leu Arg Ala Glu Asp Thr Ala Val Tyr Tyr Ser
                    85                  90                  95
Gly Arg Asp Gly Lys Cys Pro Asp Leu Lys Cys Tyr Ser Gly Leu Ile
                    100                 105                 110
Asp Tyr Trp Gly Gln Gly Thr Leu Val Thr Val Ser
                    115                 120
```

<210> SEQ ID NO 85
<211> LENGTH: 6
<212> TYPE: PRT
<213> ORGANISM: Homo sapiens

<400> SEQUENCE: 85

```
Ser Asp Tyr Gly Met His
1               5
```

<210> SEQ ID NO 86
<211> LENGTH: 17
<212> TYPE: PRT
<213> ORGANISM: Homo sapiens

<400> SEQUENCE: 86

```
Val Ile Ser Lys Asp Gly Thr Asn Thr His Tyr Ala Asp Ser Val Arg
1               5                   10                  15
Gly
```

<210> SEQ ID NO 87
<211> LENGTH: 16
<212> TYPE: PRT
<213> ORGANISM: Homo sapiens

<400> SEQUENCE: 87

```
Asp Gly Lys Cys Pro Asp Leu Lys Cys Tyr Ser Gly Leu Ile Asp Tyr
1               5                   10                  15
```

<210> SEQ ID NO 88
<211> LENGTH: 6
<212> TYPE: PRT
<213> ORGANISM: Homo sapiens

<400> SEQUENCE: 88

```
Gly Leu Thr Phe Ser Asp
1               5
```

<210> SEQ ID NO 89
<211> LENGTH: 10
<212> TYPE: PRT
<213> ORGANISM: Homo sapiens

<400> SEQUENCE: 89

```
Val Ile Ser Lys Asp Gly Thr Asn Thr His
1               5                   10
```

<210> SEQ ID NO 90
<211> LENGTH: 330
<212> TYPE: PRT
<213> ORGANISM: Homo sapiens

<400> SEQUENCE: 90

```
Gly Ala Ala Ala Thr Thr Gly Thr Gly Thr Gly Ala Cys Ala Cys
1               5                   10                  15
```

Ala Gly Thr Cys Thr Cys Gly Gly Cys Cys Ala Cys Cys Thr
         20                  25                  30

Gly Thr Cys Thr Thr Thr Gly Thr Cys Thr Cys Ala Gly Gly Gly
             35                  40                  45

Gly Ala Ala Ala Gly Ala Gly Cys Cys Ala Cys Cys Thr Cys Thr
50                  55                  60

Cys Cys Thr Gly Cys Ala Gly Gly Gly Cys Cys Ala Gly Thr Cys Ala
65                  70                  75                  80

Gly Ala Gly Thr Gly Thr Thr Gly Gly Cys Gly Gly Cys Thr Ala Cys
             85                  90                  95

Thr Thr Ala Gly Cys Cys Thr Gly Gly Thr Ala Cys Cys Ala Ala Cys
                 100                 105                 110

Ala Gly Ala Ala Gly Cys Cys Thr Gly Gly Cys Cys Ala Gly Gly Cys
             115                 120                 125

Thr Cys Cys Cys Ala Gly Gly Cys Thr Cys Cys Thr Cys Ala Thr Cys
             130                 135                 140

Thr Ala Thr Gly Ala Thr Gly Cys Ala Thr Cys Cys Ala Ala Ala Ala
145                 150                 155                 160

Gly Gly Gly Cys Cys Ala Cys Thr Gly Gly Cys Ala Thr Cys Cys Cys
             165                 170                 175

Ala Gly Cys Cys Ala Gly Gly Thr Thr Cys Ala Gly Thr Gly Gly Cys
             180                 185                 190

Ala Gly Thr Gly Gly Gly Thr Cys Thr Gly Gly Gly Ala Cys Ala Gly
             195                 200                 205

Ala Cys Thr Thr Cys Ala Cys Thr Cys Thr Cys Ala Cys Cys Ala Thr
             210                 215                 220

Cys Ala Gly Cys Ala Cys Cys Thr Ala Gly Ala Gly Cys Cys Thr
225                 230                 235                 240

Gly Ala Ala Gly Ala Thr Thr Thr Thr Gly Cys Ala Ala Thr Thr Thr
             245                 250                 255

Ala Thr Thr Ala Cys Thr Gly Thr Cys Ala Cys Ala Gly Cys Gly Gly
             260                 265                 270

Thr Ala Gly Cys Ala Gly Cys Thr Gly Gly Cys Cys Thr Cys Cys Gly
             275                 280                 285

Cys Thr Cys Ala Cys Thr Thr Thr Cys Gly Gly Cys Gly Gly Ala Gly
             290                 295                 300

Gly Gly Ala Cys Cys Ala Ala Gly Gly Thr Gly Gly Ala Thr Ala Thr
305                 310                 315                 320

Cys Ala Ala Ala Cys Gly Thr Ala Cys Gly
             325                 330

<210> SEQ ID NO 91
<211> LENGTH: 110
<212> TYPE: PRT
<213> ORGANISM: Homo sapiens

<400> SEQUENCE: 91

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Gly Tyr
             20                  25                  30

Leu Ala Trp Tyr Gln Gln Lys Pro Gly Gln Ala Pro Arg Leu Leu Ile
             35                  40                  45

Tyr Asp Ala Ser Lys Arg Ala Thr Gly Ile Pro Ala Arg Phe Ser Gly
         50                  55                  60

```
Ser Gly Ser Gly Thr Asp Phe Thr Leu Thr Ile Ser Thr Leu Glu Pro
 65                  70                  75                  80

Glu Asp Phe Ala Ile Tyr Tyr Cys His Gln Arg Ser Ser Trp Pro Pro
                 85                  90                  95

Leu Thr Phe Gly Gly Gly Thr Lys Val Asp Ile Lys Arg Thr
            100                 105                 110
```

<210> SEQ ID NO 92
<211> LENGTH: 7
<212> TYPE: PRT
<213> ORGANISM: Homo sapiens

<400> SEQUENCE: 92

```
Asp Ala Ser Lys Arg Ala Thr
 1               5
```

<210> SEQ ID NO 93
<211> LENGTH: 10
<212> TYPE: PRT
<213> ORGANISM: Homo sapiens

<400> SEQUENCE: 93

```
His Gln Arg Ser Ser Trp Pro Pro Leu Thr
 1               5                   10
```

<210> SEQ ID NO 94
<211> LENGTH: 330
<212> TYPE: DNA
<213> ORGANISM: Homo sapiens

<400> SEQUENCE: 94

```
gaaattgtct tgacacagtc tccagccacc ctgtctttgt ctccagggga aagagccacc    60
ctctcctgca gggccagtca gagtgttggc agatacttag cctggtacca acagaaaggt   120
ggccaggctc ccaggctcct catctatgat gcatccaaca gggccactgg catcccagcc   180
aggttcagtg gcagtgggtc tgggacagac ttcactctca ccatcgacag cctagagcct   240
gaagattttg cagtttatta ctgtcagcag cgtagcaact ggcctccgct cactttcggc   300
ggagggtcca aggtggagat caaacgtacg                                    330
```

<210> SEQ ID NO 95
<211> LENGTH: 6
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 95

```
Ser Xaa Xaa Gly Xaa His
 1               5
```

<210> SEQ ID NO 96
<211> LENGTH: 17
<212> TYPE: PRT
<213> ORGANISM: Artificial Sequence
<220> FEATURE:

```
<223> OTHER INFORMATION: Consensus Sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(10)
<223> OTHER INFORMATION: Xaa can be any naturally occurring amino acid

<400> SEQUENCE: 96

Val Ile Ser Xaa Asp Xaa Xaa Xaa Xaa Xaa Tyr Ala Asp Ser Val Arg
1               5                   10                  15

Gly

<210> SEQ ID NO 97
<211> LENGTH: 15
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid

<400> SEQUENCE: 97

Xaa Cys Xaa Cys Xaa Xaa Xaa Cys Tyr Ser Gly Xaa Xaa Asp Tyr
1               5                   10                  15

<210> SEQ ID NO 98
<211> LENGTH: 6
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 98

Ser Xaa Xaa Gly Ile His
1               5

<210> SEQ ID NO 99
<211> LENGTH: 17
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
```

```
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 99

Val Ile Ser Xaa Asp Gly Xaa Asn Xaa His Tyr Ala Asp Ser Val Xaa
1               5                   10                  15

Gly

<210> SEQ ID NO 100
<211> LENGTH: 16
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 100

Asp Gly Xaa Cys Ser Xaa Xaa Xaa Cys Tyr Ser Gly Leu Xaa Asp Tyr
1               5                   10                  15

<210> SEQ ID NO 101
<211> LENGTH: 6
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (2)..(2)
<223> OTHER INFORMATION: Xaa can be any naturally occurring amino acid

<400> SEQUENCE: 101

Ser Xaa Tyr Gly Met His
1               5

<210> SEQ ID NO 102
<211> LENGTH: 16
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (8)..(8)
<223> OTHER INFORMATION: Xaa can be any naturally occurring amino acid

<400> SEQUENCE: 102

Glu Gly Arg Cys Ile Glu Glu Xaa Cys Tyr Ser Gly Gln Ile Asp Tyr
1               5                   10                  15

<210> SEQ ID NO 103
<211> LENGTH: 16
<212> TYPE: PRT
<213> ORGANISM: Artificial Sequence
```

```
<220> FEATURE:
<223> OTHER INFORMATION: Consensus Sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 103

Asp Gly Xaa Cys Pro Asp Xaa Xaa Cys Tyr Ser Gly Leu Ile Asp Tyr
1               5                   10                  15

<210> SEQ ID NO 104
<211> LENGTH: 6
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 104

Xaa Xaa Xaa Phe Ser Xaa
1               5

<210> SEQ ID NO 105
<211> LENGTH: 10
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(10)
<223> OTHER INFORMATION: Xaa can be any naturally occurring amino acid

<400> SEQUENCE: 105

Val Ile Ser Xaa Asp Xaa Xaa Xaa Xaa Xaa
1               5                   10

<210> SEQ ID NO 106
<211> LENGTH: 16
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(8)
<223> OTHER INFORMATION: Xaa can be any naturally occurring amino acid
<220> FEATURE:
<221> NAME/KEY: misc_feature
```

<222> LOCATION: (13)..(14)
<223> OTHER INFORMATION: Xaa can be any naturally occurring amino acid

<400> SEQUENCE: 106

```
Xaa Gly Xaa Cys Xaa Xaa Xaa Xaa Cys Tyr Ser Gly Xaa Xaa Asp Tyr
1               5                   10                  15
```

<210> SEQ ID NO 107
<211> LENGTH: 6
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 107

```
Gly Xaa Thr Phe Ser Xaa
1               5
```

<210> SEQ ID NO 108
<211> LENGTH: 10
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (9)..(9)
<223> OTHER INFORMATION: Xaa can be any naturally occurring amino acid

<400> SEQUENCE: 108

```
Val Ile Ser Lys Asp Gly Thr Asn Xaa His
1               5                   10
```

<210> SEQ ID NO 109
<211> LENGTH: 16
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(8)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 109

```
Asp Gly Xaa Cys Xaa Xaa Xaa Xaa Cys Tyr Ser Gly Leu Xaa Asp Tyr
1               5                   10                  15
```

<210> SEQ ID NO 110
<211> LENGTH: 16
<212> TYPE: PRT
<213> ORGANISM: Artificial Sequence
<220> FEATURE:
<223> OTHER INFORMATION: Consensus Sequence
<220> FEATURE:

```
<221> NAME/KEY: misc_feature
<222> LOCATION: (8)..(8)
<223> OTHER INFORMATION: Xaa can be any naturally occurring amino acid

<400> S

```
<220> FEATURE:
<221> NAME/KEY: misc_feature
<222> LOCATION: (8)..(8)
<223> OTHER INFORMATION: Xaa can be any naturally occurring amino acid

<400> SEQUENCE: 114

Arg Ala Ser Gln Ser Val Gly Xaa Tyr Leu Ala
1               5                   10

<210> SEQ ID NO 115
<211> LENGTH: 7
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 115

Asp Ala Ser Xaa Arg Ala Thr
1               5

<210> SEQ ID NO 116
<211> LENGTH: 10
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (5)..(5)
<223> OTHER INFORMATION: Xaa can be any naturally occurring amino acid

<400> SEQUENCE: 116

His Gln Arg Ser Xaa Trp Pro Pro Leu Thr
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (5)..(5)
<223> OTHER INFORMATION: Xaa can be any naturally occurring amino acid

<400> SEQUENCE: 117

Gln Gln Arg Ser Xaa Trp Pro Pro Leu Thr
1               5                   10

<210> SEQ ID NO 118
<211> LENGTH: 6
<212> TYPE: PRT
<213> ORGANISM: Homo sapiens

<400> SEQUENCE: 118

Gly Leu Thr Phe Ser Asn
1               5

<210> SEQ ID NO 119
<211> LENGTH: 124
<212> TYPE: PRT
<213> ORGANISM: Homo sapiens

<400> SEQUENCE: 119
```

Gln Val Gln Leu Val Glu Ser Gly Gly Gly Val Ile Gln Pro Gly Arg
1               5                   10                  15

Ser Leu Arg Leu Ser Cys Val Ala Ser Lys Phe Ile Phe Ser Asn His
            20                  25                  30

Gly Ile His Trp Val Arg Gln Ala Pro Gly Lys Gly Leu Glu Trp Val
        35                  40                  45

Ala Val Ile Ser Lys Asp Gly Thr Asn Ala His Tyr Ala Asp Ser Val
    50                  55                  60

Arg Gly Arg Phe Ser Ile Ser Arg Asp Asn Ser Lys Asp Thr Val Phe
65                  70                  75                  80

Leu Glu Met Arg Ser Leu Arg Pro Glu Asp Thr Ala Val Tyr Tyr Cys
                85                  90                  95

Ala Arg Glu Gly Arg Cys Ile Glu Glu Asn Cys Tyr Ser Gly Gln Ile
            100                 105                 110

Asp Tyr Trp Gly Gln Gly Ser Leu Val Thr Val Ser
        115                 120

<210> SEQ ID NO 120
<211> LENGTH: 124
<212> TYPE: PRT
<213> ORGANISM: Homo sapiens

<400> SEQUENCE: 120

Gln Val Gln Leu Val Glu Ser Gly Gly Gly Val Ile Gln Pro Gly Arg
1               5                   10                  15

Ser Leu Arg Leu Ser Cys Val Ala Ser Lys Phe Ile Phe Ser Asn His
            20                  25                  30

Gly Ile His Trp Val Arg Gln Ala Pro Gly Lys Gly Leu Glu Trp Val
        35                  40                  45

Ala Val Ile Ser Lys Asp Gly Thr Asn Ala His Tyr Ala Asp Ser Val
    50                  55                  60

Arg Gly Arg Phe Ser Ile Ser Arg Asp Asn Ser Lys Asp Thr Val Phe
65                  70                  75                  80

Leu Glu Met Arg Ser Leu Arg Pro Glu Asp Thr Ala Val Tyr Tyr Cys
                85                  90                  95

Ala Arg Glu Gly Arg Cys Ile Glu Glu Lys Cys Tyr Ser Gly Gln Ile
            100                 105                 110

Asp Tyr Trp Gly Gln Gly Ser Leu Val Thr Val Ser
        115                 120

<210> SEQ ID NO 121
<211> LENGTH: 124
<212> TYPE: PRT
<213> ORGANISM: Homo sapiens

<400> SEQUENCE: 121

Gln Val Gln Leu Val Glu Ser Gly Gly Gly Val Ile Gln Pro Gly Arg
1               5                   10                  15

Ser Leu Arg Leu Ser Cys Val Ala Ser Lys Phe Ile Phe Ser Asn His
            20                  25                  30

Gly Ile His Trp Val Arg Gln Ala Pro Gly Lys Gly Leu Glu Trp Val
        35                  40                  45

Ala Val Ile Ser Lys Asp Gly Thr Asn Ala His Tyr Ala Asp Ser Val
    50                  55                  60

Arg Gly Arg Phe Ser Ile Ser Arg Asp Asn Ser Lys Asp Thr Val Phe
65                  70                  75                  80

```
Leu Glu Met Arg Ser Leu Arg Pro Glu Asp Thr Ala Val Tyr Tyr Cys
                85                  90                  95

Ala Arg Glu Gly Arg Cys Ile Glu Glu Lys Cys Tyr Ser Gly Gln Ile
            100                 105                 110

Asp Tyr Trp Gly Gln Gly Ser Leu Val Thr Val Ser
        115                 120

<210> SEQ ID NO 122
<211> LENGTH: 124
<212> TYPE: PRT
<213> ORGANISM: Artificial Sequence
<220> FEATURE:
<223> OTHER INFORMATION: Consensus Sequence

<400> SEQUENCE: 122

Gln Val Gln Leu Val Glu Ser Gly Gly Gly Val Ile Gln Pro Gly Arg
1               5                   10                  15

Ser Leu Arg Leu Ser Cys Val Ala Ser Lys Phe Ile Phe Ser Asn His
            20                  25                  30

Gly Ile His Trp Val Arg Gln Ala Pro Gly Lys Gly Leu Glu Trp Val
        35                  40                  45

Ala Val Ile Ser Lys Asp Gly Thr Asn Ala His Tyr Ala Asp Ser Val
    50                  55                  60

Arg Gly Arg Phe Ser Ile Ser Arg Asp Asn Ser Lys Asp Thr Val Phe
65                  70                  75                  80

Leu Glu Met Arg Ser Leu Arg Pro Glu Asp Thr Ala Val Tyr Tyr Cys
                85                  90                  95

Ala Arg Glu Gly Arg Cys Ile Glu Glu Lys Cys Tyr Ser Gly Gln Ile
            100                 105                 110

Asp Tyr Trp Gly Gln Gly Ser Leu Val Thr Val Ser
        115                 120

<210> SEQ ID NO 123
<211> LENGTH: 110
<212> TYPE: PRT
<213> ORGANISM: Homo sapiens

<400> SEQUENCE: 123

Glu Ile Leu Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Arg Tyr
            20                  25                  30

Met Ala Trp Tyr Gln Gln Arg Pro Gly Gln Ala Pro Arg Leu Leu Ile
        35                  40                  45

Tyr Asp Ala Ser Ile Arg Ala Thr Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Gln Gln Arg Ser Ser Trp Pro Pro
                85                  90                  95

Leu Thr Phe Gly Gly Gly Thr Lys Val Asp Ile Lys Arg Thr
            100                 105                 110

<210> SEQ ID NO 124
<211> LENGTH: 108
<212> TYPE: PRT
<213> ORGANISM: Homo sapiens
```

-continued

<400> SEQUENCE: 124

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Gly Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Ala Gly Ile Pro Ser Arg Phe Ser Gly
50                  55                  60

Ser Gly Ser Gly Thr Asp Phe Thr Leu Thr Ile Ser Ser Leu Ala Pro
65                  70                  75                  80

Glu Asp Phe Ala Val Tyr Phe Cys Gln Gln Arg Ser Ser Trp Pro Pro
                85                  90                  95

Leu Thr Phe Gly Gly Gly Thr Lys Val Asp Ile Lys
            100                 105

<210> SEQ ID NO 125
<211> LENGTH: 109
<212> TYPE: PRT
<213> ORGANISM: Homo sapiens

<400> SEQUENCE: 125

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr His Trp
                85                  90                  95

Thr Phe Gly Gln Gly Thr Lys Val Asp Ile Lys Arg Thr
            100                 105

<210> SEQ ID NO 126
<211> LENGTH: 110
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (79)..(79)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid

<400> SEQUENCE: 126

Glu Ile Val Leu Thr Gln Ser Pro Ala Thr Leu Ser Leu Ser Pro Gly

-continued

```
1               5                   10                  15
Glu Arg Ala Thr Leu Ser Cys Arg Ala Ser Gln Ser Val Gly Xaa Tyr
            20                  25                  30

Leu Ala Trp Tyr Gln Gln Lys Pro Gly Gln Ala Pro Arg Leu Leu Ile
            35                  40                  45

Tyr Asp Ala Ser Xaa Arg Ala Thr Gly Ile Pro Ala Arg Phe Ser Gly
    50                  55                  60

Ser Gly Ser Gly Thr Asp Phe Thr Leu Thr Ile Ser Ser Leu Xaa Pro
65                  70                  75                  80

Glu Asp Phe Ala Xaa Tyr Tyr Cys Gln Gln Arg Ser Ser Trp Pro Pro
            85                  90                  95

Leu Thr Phe Gly Gly Gly Thr Lys Val Glu Ile Lys Arg Thr
            100                 105                 110
```

COMPOSITIONS AND METHODS FOR THE THERAPY AND DIAGNOSIS OF CYTOMEGALOVIRUS INFECTIONS

RELATED APPLICATIONS

This application is a continuation application of U.S. Ser. No. 13/109,632, filed May 17, 2011, which is a continuation application of U.S. Ser. No. 12/401,585, filed Mar. 10, 2009 (Now, U.S. Pat. No. 7,982,012), which claims the benefit of provisional application U.S. Ser. No. 61/068,798, filed Mar. 10, 2008, the contents of which are each herein incorporated by reference in their entireties.

INCORPORATION OF SEQUENCE LISTING

The contents of the text file named "37418-504C02US_ST26.txt" which was created on Feb. 5, 2014 and is 107 KB in size, are hereby incorporated by reference in their entirety.

FIELD OF THE INVENTION

The present invention relates generally to therapy, diagnosis and monitoring of cytomegalovirus (CMV) infection. The invention is more specifically related to human CMV (HCMV)-specific antibodies and their manufacture and use. Such antibodies are useful in pharmaceutical compositions for the prevention and treatment of CMV infection, and for the diagnosis and monitoring of CMV infection.

BACKGROUND OF THE INVENTION

CMV is associated with widespread morbidity and mortality. Infection with cytomegalovirus (CMV) is common, and it has been estimated that between 50% and 85% of people in the United States have had a CMV infection by the time they are 40 years old. Although CMV infection generally does not produce symptoms in healthy adults, high-risk groups, including immunocompromised organ transplant recipients and HIV-infected individuals, are at risk of developing CMV-associated disease. In addition, CMV is an important cause of congenital infection in the developed world, leading to mental retardation and developmental disabilities.

CMV is a member of the herpesvirus family in any species. In human, CMV, also referred to as HCMV, is designated as human herpesvirus 5 (HHV-5). CMV is the largest member of the herpesvirus family, with a double-stranded DNA genome of more than 240 kbp, capable of encoding more than 200 potential protein products. CMV is also referred to as a Beta-herpesvirinae, since it is a herpes virus that infects mononuclear cells and lymphocytes. Humans are the only natural host for CMV infection, although other mammals are infected with other forms of CMV.

Medical care for patients suffering from CMV-associated disease consists of nutritional support, supportive care for end-organ syndromes (particularly pneumonia in immuno-compromised patients), and specific antiviral therapy. At least three antiviral therapies are approved by the US Food and Drug Administration (FDA) for treatment or prevention of CMV infection. These include the nucleosides: ganciclovir (GCV) and cidofovir, as well as foscarnet. GCV is commonly used as preemptive therapy in transplant recipients at high risk of developing disease. Acyclovir has also been used as prophylaxis for solid organ transplantation, but the bioavailability is poor, and no data support use in children. Immunoglobulins have also been used as passive immunization for the prevention of CMV-associated disease. In general, while these agents have shown efficacy in treating or preventing CMV infection, nucleosides, in particular, are associated with serious side effects, including anemia and other blood problems. Accordingly, their use in children is limited.

Clearly, there is a need in the art for new agents useful for the treatment and prevention of symptomatic CMV infection and associated diseases, particularly for the treatment of children.

SUMMARY OF THE INVENTION

The invention provides an isolated anti-CMV antibody or fragment thereof, wherein the antibody includes: I: (a) a $V_H$ region including (i) a $V_H$ CDR1 region including the amino acid sequence of SNHGIH (SEQ ID NO: 36); (ii) a $V_H$ CDR2 region including the amino acid sequence of VISSDGD-DDRYADSVKG (SEQ ID NO: 37); (iii) a $V_H$ CDR3 region including the amino acid sequence of DGRCGEPKCYS-GLPDY (SEQ ID NO: 38); and (b) a $V_L$ region including (i) a $V_L$ CDR1 region including the amino acid sequence of RASQSVGGYLA (SEQ ID NO: 43); (ii) a $V_L$ CDR2 region including the amino acid sequence of DASNRAT (SEQ ID NO: 44); (iii) a $V_L$ CDR3 region including the amino acid sequence of LQRNTWPPLT (SEQ ID NO: 45); II: (a) a $V_H$ region including (i) a $V_H$ CDR1 region including the amino acid sequence of SNYGMH (SEQ ID NO: 48); (ii) a $V_H$ CDR2 region including the amino acid sequence of VISSDG-SNEHYADSVKG (SEQ ID NO: 49); (iii) a $V_H$ CDR3 region including the amino acid sequence of DGRCPDVNCYS-GLIDY (SEQ ID NO: 50); and (b) a $V_L$ region including (i) a $V_L$ CDR1 region including the amino acid sequence of RASQSVGRYLA (SEQ ID NO: 53); (ii) a $V_L$ CDR2 region including the amino acid sequence of DASNRAT (SEQ ID NO: 44); (iii) a $V_L$ CDR3 region including the amino acid sequence of QQRSNWPPLT (SEQ ID NO: 54); III: (a) a $V_H$ region including (i) a $V_H$ CDR1 region including the amino acid sequence of SSNGIH (SEQ ID NO: 57); (ii) a $V_H$ CDR2 region including the amino acid sequence of VISSDAND-KQYADSVKG (SEQ ID NO: 58); (iii) a $V_H$ CDR3 region including the amino acid sequence of DGTCSGGNCYS-GLIDY (SEQ ID NO: 59); and (b) a $V_L$ region including (i) a $V_L$ CDR1 region including the amino acid sequence of RASQSVGGYLA (SEQ ID NO: 43); (ii) a $V_L$ CDR2 region including the amino acid sequence of ASIRAT (SEQ ID NO: 64); (iii) a $V_L$ CDR3 region including the amino acid sequence of HQRSNWPPLT (SEQ ID NO: 65); IV: (a) a $V_H$ region including (i) a $V_H$ CDR1 region including the amino acid sequence of SNHGIH (SEQ ID NO: 36); (ii) a $V_H$ CDR2 region including the amino acid sequence of VISKDGT-NAHYADSVRG (SEQ ID NO: 68); (iii) a $V_H$ CDR3 region including the amino acid sequence of EGRCIEENCYSG-QIDY (SEQ ID NO: 69); and (b) a $V_L$ region including (i) a $V_L$ CDR1 region including the amino acid sequence of RASQS-VGRYMA (SEQ ID NO: 74); (ii) a $V_L$ CDR2 region including the amino acid sequence of DASIRAT (SEQ ID NO: 75); (iii) a $V_L$ CDR3 region including the amino acid sequence of QQRSSWPPLT (SEQ ID NO: 76); V: (a) a $V_H$ region including (i) a $V_H$ CDR1 region including the amino acid sequence of SNHGIH (SEQ ID NO: 36); (ii) a $V_H$ CDR2 region including the amino acid sequence of VISKDGTNAHYADSVRGR (SEQ ID NO: 79); (iii) a $V_H$ CDR3 region including the amino acid sequence of EGRCIEEKCYSGQIDY (SEQ ID NO: 80); and (b) a $V_L$ region including (i) a $V_L$ CDR1 region including the amino acid sequence of RASQSVGRYMA (SEQ ID NO: 74); (ii) a $V_L$ CDR2 region including the amino acid sequence of DASIRAT (SEQ ID NO: 75); (iii) a $V_L$ CDR3 region including the amino acid sequence of QQRSSWPPLT (SEQ ID NO: 76); VI: (a) a $V_H$ region including (i) a $V_H$ CDR1 region including the amino acid sequence of SDYGMH (SEQ ID NO: 85); (ii) a $V_H$ CDR2 region including the amino acid sequence of VISKDGTNTHYADSVRG (SEQ ID NO: 86); (iii) a $V_H$ CDR3 region including the amino acid sequence of DGKCPDLKCYSGLIDY (SEQ ID NO: 87); and (b) a $V_L$ region including (i) a $V_L$ CDR1 region including the amino acid sequence of RASQSVGGYLA (SEQ ID NO: 43); (ii) a $V_L$ CDR2 region including the amino acid sequence of DASKRAT (SEQ ID NO: 92); (iii) a $V_L$ CDR3 region including the amino acid sequence of HQRSSWPPLT (SEQ ID NO: 93); VII: (a) a $V_H$ region including (i) a $V_H$ CDR1 region including the amino acid sequence of SXXGXH (SEQ ID NO: 95), SXXGIH (SEQ ID NO: 98), or SXYGMH (SEQ ID NO: 101); (ii) a $V_H$ CDR2 region including the amino acid sequence of VISXDXXXXXYADSVRG (SEQ ID NO: 96) or VISXDGXNXHYADSVXG (SEQ ID NO: 99); (iii) a $V_H$ CDR3 region including the amino acid sequence of DGXC-SXXXCYSGLXDY (SEQ ID NO: 100), EGRCIEEXCYS-GQIDY (SEQ ID NO: 102), or DGXCPDXXCYSGLIDY (SEQ ID NO: 103); and (b) a $V_L$ region including (i) a $V_L$ CDR1 region including the amino acid sequence of RASQS-VGXYXA (SEQ ID NO: 111) or RASQSVGXYLA (SEQ ID NO: 114); (ii) a $V_L$ CDR2 region including the amino acid sequence of XASXRAT (SEQ ID NO: 112) or DASXRAT (SEQ ID NO: 115); (iii) a $V_L$ CDR3 region including the amino acid sequence of XQRXXWPPLT (SEQ ID NO: 113), HQRSXWPPLT (SEQ ID NO: 116), or QQRSXWPPLT (SEQ ID NO: 117).

The invention also provides an isolated anti-CMV antibody or fragment thereof, wherein the antibody comprises: I: (a) a $V_H$ region including (i) a $V_H$ CDR1 region including the amino acid sequence of GFTFSN (SEQ ID NO: 39); (ii) a $V_H$ CDR2 region including the amino acid sequence of VISS-DGDDDR (SEQ ID NO: 40); (iii) a $V_H$ CDR3 region including the amino acid sequence of DGRCGEPKCYSGLPDY (SEQ ID NO: 38); and (b) a $V_L$ region including (i) a $V_L$ CDR1 region including the amino acid sequence of RASQS-VGGYLA (SEQ ID NO: 43); (ii) a $V_L$ CDR2 region including the amino acid sequence of DASNRAT (SEQ ID NO: 44); (iii) a $V_L$ CDR3 region including the amino acid sequence of LQRNTWPPLT (SEQ ID NO: 45); II: (a) a $V_L$ region including (i) a $V_H$ CDR1 region including the amino acid sequence of GLTFSN (SEQ ID NO: 118); (ii) a $V_H$ CDR2 region including the amino acid sequence of VISSDGSNEH (SEQ ID NO: 51); (iii) a $V_H$ CDR3 region including the amino acid sequence of DGRCPDVNCYSGLIDY (SEQ ID NO: 50); and (b) a $V_L$ region including (i) a $V_L$ CDR1 region including the amino acid sequence of RASQSVGRYLA (SEQ ID NO: 53); (ii) a $V_L$ CDR2 region including the amino acid sequence of DASNRAT (SEQ ID NO: 44); (iii) a $V_L$ CDR3 region including the amino acid sequence of QQRSNWPPLT (SEQ ID NO: 54); III: (a) a $V_H$ region including (i) a $V_H$ CDR1 region including the amino acid sequence of GFTFSS (SEQ ID NO: 60); (ii) a $V_H$ CDR2 region including the amino acid sequence of VISSDANDKQ (SEQ ID NO: 61); (iii) a $V_H$ CDR3 region including the amino acid sequence of DGTC-SGGNCYSGLIDY (SEQ ID NO: 59); and (b) a $V_L$ region including (i) a $V_L$ CDR1 region including the amino acid sequence of RASQSVGGYLA (SEQ ID NO: 43); (ii) a $V_L$ CDR2 region including the amino acid sequence of ASIRAT (SEQ ID NO: 64); (iii) a $V_L$ CDR3 region including the amino acid sequence of HQRSNWPPLT (SEQ ID NO: 65); IV: (a) a $V_H$ region including (i) a $V_H$ CDR1 region including the amino acid sequence of KFIFSN (SEQ ID NO: 70); (ii) a $V_H$ CDR2 region including the amino acid sequence of VISKDGTNAH (SEQ ID NO: 71); (iii) a $V_H$ CDR3 region including the amino acid sequence of EGRCIEENCYSG-QIDY (SEQ ID NO: 69); and (b) a $V_L$ region including (i) a $V_L$ CDR1 region including the amino acid sequence of RASQS-VGRYMA (SEQ ID NO: 74); (ii) a $V_L$ CDR2 region including the amino acid sequence of DASIRAT (SEQ ID NO: 75); (iii) a $V_L$ CDR3 region including the amino acid sequence of QQRSSWPPLT (SEQ ID NO: 76); V: (a) a $V_H$ region including (i) a $V_H$ CDR1 region including the amino acid sequence of KFIFSN (SEQ ID NO: 70); (ii) a $V_H$ CDR2 region including the amino acid sequence of VISKDGTNAH (SEQ ID NO: 71); (iii) a $V_H$ CDR3 region including the amino acid sequence of EGRCIEEKCYSGQIDY (SEQ ID NO: 80); and (b) a $V_L$ region including (i) a $V_L$ CDR1 region including the amino acid sequence of RASQSVGRYMA (SEQ ID NO: 74); (ii) a $V_L$ CDR2 region including the amino acid sequence of DASIRAT (SEQ ID NO: 75); (iii) a $V_L$ CDR3 region including the amino acid sequence of QQRSSWPPLT (SEQ ID NO: 76); VI: (a) a $V_H$ region including (i) a $V_H$ CDR1 region including the amino acid sequence of GLTFSD (SEQ ID NO: 88); (ii) a $V_H$ CDR2 region including the amino acid sequence of VISKDGTNTH (SEQ ID NO: 89); (iii) a $V_H$ CDR3 region including the amino acid sequence of DGKCP-DLKCYSGLIDY (SEQ ID NO: 87); and (b) a $V_L$ region including (i) a $V_L$ CDR1 region including the amino acid sequence of RASQSVGGYLA (SEQ ID NO: 43); (ii) a $V_L$ CDR2 region including the amino acid sequence of DASK-RAT (SEQ ID NO: 92); (iii) a $V_L$ CDR3 region including the amino acid sequence of HQRSSWPPLT (SEQ ID NO: 93); VII: (a) a $V_H$ region including (i) a $V_H$ CDR1 region including the amino acid sequence of XXXFSX (SEQ ID NO: 104) or GXTFSX (SEQ ID NO: 107); (ii) a $V_H$ CDR2 region including the amino acid sequence of VISXDXXXXX (SEQ ID NO: 105) or VISKDGTNXH (SEQ NO: 108); (iii) a $V_H$ CDR3 region including the amino acid sequence of XGX-CXXXXCYSGXXDY (SEQ ID NO: 106), DGXCXXXX-CYSGLXDY (SEQ ID NO: 109), or EGRCIEEXCYSG-QIDY (SEQ ID NO: 110); and (b) a $V_L$ region including (i) a $V_L$ CDR1 region including the amino acid sequence of RASQSVGXYXA (SEQ ID NO: 111) or RASQSVGXYLA (SEQ ID NO: 114); (ii) a $V_L$ CDR2 region including the amino acid sequence of XASXRAT (SEQ ID NO: 112) or DASXRAT (SEQ ID NO: 115); (iii) a $V_L$ CDR3 region including the amino acid sequence of XQRXXWPPLT (SEQ ID NO: 113), HQRSXWPPLT (SEQ ID NO: 116), or QQRSXWPPLT (SEQ ID NO: 117).

The invention further provides an isolated anti-CMV antibody including: (a) a heavy chain sequence including the amino acid sequence of SEQ ID NO: 35 and a light chain sequence including amino acid sequence SEQ ID NO: 42 or (b) a heavy chain sequence including the amino acid sequence of SEQ ID NO: 47 and a light chain sequence including amino acid sequence SEQ ID NO: 52 or (c) a heavy chain sequence including the amino acid sequence of SEQ ID NO: 56 and a light chain sequence including amino acid sequence SEQ ID NO: 63 or (d) a heavy chain sequence including the amino acid sequence of SEQ ID NO: 67 and a light chain sequence including amino acid sequence SEQ ID NO: 73 or (e) a heavy chain sequence including the amino acid sequence of SEQ ID NO: 78 and a light chain sequence including amino acid sequence SEQ ID NO: 82 or f) a heavy chain sequence including the amino acid sequence of SEQ ID NO: 84 and a light chain sequence including amino acid sequence SEQ ID NO: 91.

The anti-CMV antibody of the invention binds an epitope of the glycoprotein b (gB) envelope protein of the CMV virus.

In one aspect of the invention, the epitope comprises the antigenic determinant 2 site 1 of gB, gp116.

The invention provides a composition including one or more of the antibodies described herein. In certain embodiments, the composition also includes an anti-viral treatment. Non-limiting examples of anti-viral treatments are ganciclovir, foscarnet, cidofovir, valganciclovir, and intravenous immunoglobulin (IVIG). In other embodiments, the composition further includes a second anti-CMV antibody.

The invention further provides an anti-CMV antibody, such as those described herein, wherein the antibody is operably-linked to a therapeutic agent or a detectable label.

The invention provides a method for the treatment or prevention of a CMV infection in a subject, including administering to the subject the composition described herein. In one aspect, this method further includes administering an anti-viral treatment. Anti-viral treatments include, but are not limited to, the following examples: ganciclovir, foscarnet, cidofovir, valganciclovir, and intravenous immunoglobulin (IVIG). In another aspect of the above method, the composition containing an anti-CMV antibody is administered prior to or after exposure to CMV at a dose sufficient to neutralize CMV infection.

Additional methods of the invention are provided for determining the presence of a CMV infection in a patient, including the steps of: (a) contacting a biological sample obtained from the patient with an antibody described herein; (b) detecting an amount of the antibody that binds to the biological sample; and (c) comparing the amount of antibody that binds to the biological sample to a control value, and therefrom determining the presence of the influenza virus in the patient.

The invention also provides a kit including an antibody described herein.

Alternatively, or in addition, the invention provides an isolated human monoclonal antibody, wherein the monoclonal antibody binds to an epitope in the extracellular domain of the glycoprotein gB complex of a cytomegalovirus (CMV). In a preferred embodiment, the CMV is a human CMV (HCMV). In another preferred embodiment, the antibody is isolated from a B-cell from a human donor.

In certain aspects of the invention, the epitope of the isolated human monoclonal antibody antibody includes the AD-2 region of the CMV gB complex. Specifically, the epitope includes the amino acids at positions 70-88 of a CMV gB polypeptide, wherein amino acid position numbers are in accordance with SEQ ID NO: 30. Alternatively, the epitope includes the amino acids at positions 65-93 of a CMV gB complex, wherein amino acid position numbers are in accordance with SEQ ID NO: 30. A further alternative epitope includes the amino acids at positions 60-98 of a CMV gB complex, wherein amino acid position numbers are in accordance with SEQ ID NO: 30.

In certain embodiments of the invention, the epitope of the antibody described herein is wholly of partially comprises the amino acid sequence NETIYNTTLKYGDVVGVN (SEQ ID NO: 32) or $NIX_3NX_4TX_5X_6X_7X_8X_9X_{10}X_{11}X_{12}X_{13}X_{14}$ (SEQ ID NO: 33) wherein $X_1$=amino acid E or T, $X_2$=T or V, $X_3$=Y or R, $X_4$=T or L, $X_5$=L or A, $X_6$=K or S, $X_7$=Y or V, $X_8$=G or D, $X_9$=D or F, $X_{10}$=V or S, $X_{11}$=V or Q, $X_{12}$=G or none, $X_{13}$=V or none, and $X_{14}$=N or none. In a further embodiment, the epitope wholly of partially includes the amino acid sequence SHRANETIYNTTLKYGDTTGTNTTK (SEQ ID NO: 31).

The isolated human monoclonal antibody of the invention is 2F10, 2M16, 2N9, 3C21, 4P12, 5P9, or 9C16. Alternatively, or in addition, the invention provides an antibody that binds the same epitope as 2F10, 2M16, 2N9, 3C21, 4P12, 5P9, or 9C16. In a preferred embodiment, the invention provides an isolated human monoclonal antibody that binds the same epitope as 2F10, 2M16, 2N9, 3C21, 4P12, 5P9, or 9C16.

The invention also provides an isolated human monoclonal anti-CMV antibody or fragment thereof, wherein the antibody includes a heavy chain variable region ($V_H$) including CDR1 and CDR2, wherein the region is encoded by a human IGHV3 $V_H$ germline sequence, or a nucleic acid sequence that is homologous to the said $V_H$ germline gene sequence. In one aspect, the nucleic acid sequence that is homologous to the germline sequence is at least 90% homologous to the IGHV3 germline sequence. The antibody of the invention further includes a light chain variable region (VL) encoded by a human IGKV3 $V_L$ germline gene sequence, or a nucleotide acid sequence that is homologous to the said $V_L$ germline gene sequence. In one aspect, the nucleic acid sequence that is homologous to the $V_L$ germline sequence is at least 90% homologous to the IGKV3 $V_L$ germline sequence.

DETAILED DESCRIPTION OF THE INVENTION

Figure 1A:
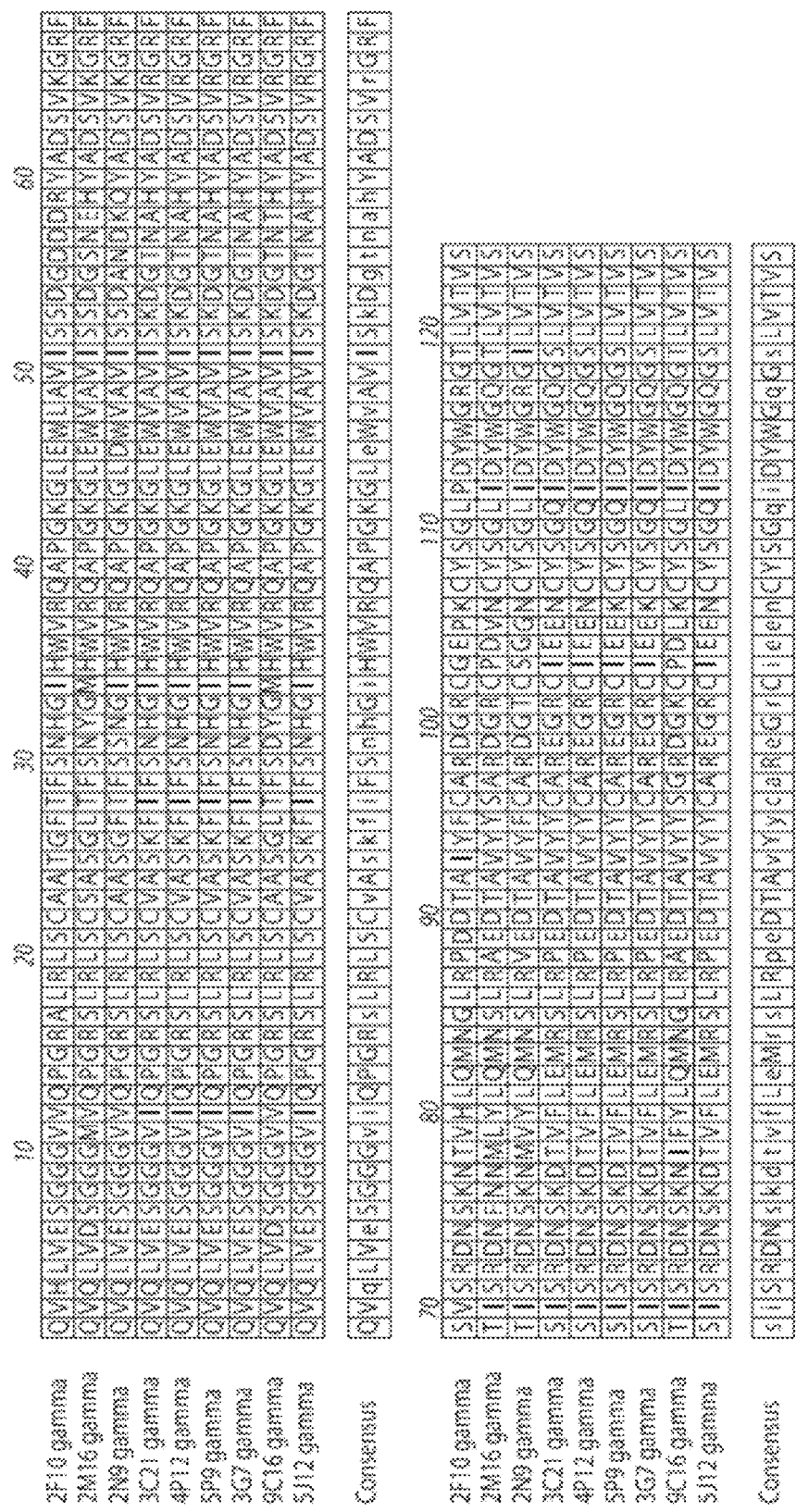
FIG. 1A provides an alignment of the gamma heavy chain variable regions for the following sequences: 2F10 (SEQ ID NO: 35); M16 (SEQ ID NO: 47); 2N9 (SEQ ID NO: 56); 3C21 (SEQ ID NO: 119); 4P12 (SEQ ID NO: 67); 5P9 (SEQ ID NO: 78); 3G7 (SEQ ID NO: 120); 9C16 (SEQ ID NO: 84); and 5J12 (SEQ ID NO: 121), and FIG. 1B provides an alignment of the kappa light chain variable regions for the following sequences: 2F10 (SEQ ID NO: 42); 2M16 (SEQ ID NO: 52); 2N9 (SEQ ID NO: 63); 3C21 (SEQ ID NO: 123); 4P12 (SEQ ID NO: 73); ITC88 (SEQ ID NO: 124); 3G7 (SEQ ID NO: 125); 5P9 (SEQ ID NO: 82); and 9C16 (SEQ ID NO: 91). Consensus sequences (SEQ ID NO: 122 and SEQ ID NO: 126 respectively) are shown below each alignment.

The present invention is directed generally to compositions and their use in the diagnosis, prevention, and therapy of cytomegalovirus (CMV) infection. As described further below, illustrative compositions of the present invention include, but are not restricted to, HCMV-specific antibodies, and fragments and derivatives thereof.

In one embodiment, the anti-CMV antibodies of the invention bind wholly or partially to the amino acid sequence SHRANETIYNTTLKYGDTTGTNTTK (SEQ ID NO: 31) or NETIYNTTLKYGDVVGVN (SEQ ID NO: 32). Most preferably, the anti-CMV antibodies of the invention bind wholly or partially to the amino acid sequence NIX$_3$NX$_4$TX$_5$X$_6$X$_7$X$_8$X$_9$X$_{10}$X$_{11}$X$_{12}$X$_{13}$X$_{14}$ (SEQ ID NO: 33) wherein X$_1$=amino acid E or T, X$_2$=T or V, X$_3$=Y or R, X$_4$=T or L, X$_5$=L or A, X$_6$=K or S, X$_7$=Y or V, X$_8$=G or D, X$_9$=D or F, X$_{10}$=V or S, X$_{11}$=V or Q, X$_{12}$=G or none, X$_{13}$=V or none, and X$_{14}$=N or none. Exemplary anti-CMV monoclonal antibodies that bind to this epitope are the 2F10, 2M16, 2N9, 4P12, 5P9, 9C16 antibodies described herein.

The amino acids encompassing the CDRs as defined by Chothia, C. et al. (1989, Nature, 342: 877-883) are italicized and those defined by Kabat E. A. et al. (1991, Sequences of Proteins of Immunological Interest, 5$^{th}$ edit., NIH Publication no. 91-3242 U.S. Department of Health and Human Services.) are underlined in bold in the sequences as described in the Examples herein. One of ordinary skill in the art would readily recognize that there are several standard methods of defining CDRs within the variable region of an antibody. Two of the most widely used are shown herein. The ordinarily skilled artisan would also readily recognize that other art-recognized methods of delineating CDRs are encompassed by the invention.

The 2F10 antibody includes a heavy chain variable region (SEQ ID NO: 35) encoded by the nucleic acid sequence shown below in SEQ ID NO: 34, and a light chain variable region (SEQ ID NO: 42) encoded by the nucleic acid sequence shown in SEQ ID NO: 41.

The heavy chain CDRs of the 2F10 antibody have the following sequences per Kabat definition: SNHGIH (SEQ ID NO: 36), VISSDGDDDRYADSVKG (SEQ ID NO: 37), and DGRCGEPKCYSGLPDY (SEQ ID NO: 38). The light chain CDRs of the 2F10 antibody have the following sequences per Kabat definition: RASQSVGGYLA (SEQ ID NO: 43), DASNRAT (SEQ ID NO: 44), and LQRNTWPPLT (SEQ ID NO: 45).

The heavy chain CDRs of the 2F10 antibody have the following sequences per Chothia definition: GFTFSN (SEQ ID NO: 39), VISSDGDDDR (SEQ ID NO: 40), and DGRCGEPKCYSGLPDY (SEQ ID NO: 38). The light chain CDRs of the 2F10 antibody have the following sequences per Chothia definition: RASQSVGGYLA (SEQ ID NO: 43), DASNRAT (SEQ ID NO: 44), and LQRNTWPPLT (SEQ ID NO: 45).

The 2M16 antibody includes a heavy chain variable region (SEQ ID NO: 47) encoded by the nucleic acid sequence shown below in SEQ ID NO: 46, and a light chain variable region (SEQ ID NO: 52) encoded by the nucleic acid sequence shown in SEQ ID NO: 94.

The heavy chain CDRs of the 2M16 antibody have the following sequences per Kabat definition: SNYGMH (SEQ ID NO: 48), VISSDGSNEHYADSVKG (SEQ ID NO: 49), and DGRCPDVNCYSGLIDY (SEQ ID NO: 50). The light chain CDRs of the 2M16 antibody have the following sequences per Kabat definition: RASQSVGRYLA (SEQ ID NO: 53), DASNRAT (SEQ ID NO: 44), and QQRSNWPPLT (SEQ ID NO: 54).

The heavy chain CDRs of the 2M16 antibody have the following sequences per Chothia definition: GLTFSN (SEQ ID NO: 118), VISSDGSNEH (SEQ ID NO: 51), and DGRCPDVNCYSGLIDY (SEQ ID NO: 50). The light chain CDRs of the 2M16 antibody have the following sequences per Chothia definition: RASQSVGRYLA (SEQ ID NO: 53), DASNRAT (SEQ ID NO: 44), and QQRSNWPPLT (SEQ ID NO: 54).

The 2N9 antibody includes a heavy chain variable region (SEQ ID NO: 56) encoded by the nucleic acid sequence shown below in SEQ ID NO: 55, and a light chain variable region (SEQ ID NO: 63) encoded by the nucleic acid sequence shown in SEQ ID NO: 62.

The heavy chain CDRs of the 2N9 antibody have the following sequences per Kabat definition: SSNGIH (SEQ ID NO: 57), VISSDANDKQYADSVKG (SEQ ID NO: 58), and DGTCSGGNCYSGLIDY (SEQ ID NO: 59). The light chain CDRs of the 2N9 antibody have the following sequences per Kabat definition: RASQSVGGYLA (SEQ ID NO: 43), ASIRAT (SEQ ID NO: 64), and HQRSNWPPLT (SEQ ID NO: 65).

The heavy chain CDRs of the 2N9 antibody have the following sequences per Chothia definition: GFTFSS (SEQ ID NO: 60), VISSDANDKQ (SEQ ID NO: 61), and DGTCSG-GNCYSGLIDY (SEQ ID NO: 59). The light chain CDRs of the 2N9 antibody have the following sequences per Chothia definition: RASQSVGGYLA (SEQ ID NO: 43), ASIRAT (SEQ ID NO: 64), and HQRSNWPPLT (SEQ ID NO: 65).

The 4P12 antibody includes a heavy chain variable region (SEQ ID NO: 67) encoded by the nucleic acid sequence shown below in SEQ ID NO: 66, and a light chain variable region (SEQ ID NO: 73) encoded by the nucleic acid sequence shown in SEQ ID NO: 72.

The heavy chain CDRs of the 4P12 antibody have the following sequences per Kabat definition: SNHGIH (SEQ ID NO: 36), VISKDGTNAHYADSVRG (SEQ ID NO: 68), and EGRCIEENCYSGQIDY (SEQ ID NO: 69). The light chain CDRs of the 4P12 antibody have the following sequences per Kabat definition: RASQSVGRYMA (SEQ ID NO: 74), DASIRAT (SEQ ID NO: 75), and QQRSSWPPLT (SEQ ID NO: 76).

The heavy chain CDRs of the 4P12 antibody have the following sequences per Chothia definition: KFIFSN (SEQ ID NO: 70), VISKDGTNAH (SEQ ID NO: 71), and EGR-CIEENCYSGQIDY (SEQ ID NO: 69). The light chain CDRs of the 4P12 antibody have the following sequences per Chothia definition: RASQSVGRYMA (SEQ ID NO: 74), DASIRAT (SEQ ID NO: 75), and QQRSSWPPLT (SEQ ID NO: 76).

The 5P9 antibody includes a heavy chain variable region (SEQ ID NO: 78) encoded by the nucleic acid sequence shown below in SEQ ID NO: 77, and a light chain variable region (SEQ ID NO: 82) encoded by the nucleic acid sequence shown in SEQ ID NO: 81.

The heavy chain CDRs of the 5P9 antibody have the following sequences per Kabat definition: SNHGIH (SEQ ID NO: 36), VISKDGTNAHYADSVRGR (SEQ ID NO: 79), and EGRCIEEKCYSGQIDY (SEQ ID NO: 80). The light chain CDRs of the 5P9 antibody have the following sequences per Kabat definition: RASQSVGRYMA (SEQ ID NO: 74), DASIRAT (SEQ ID NO: 75), and QQRSSWPPLT (SEQ ID NO: 76).

The heavy chain CDRs of the 5P9 antibody have the following sequences per Chothia definition: KFIFSN (SEQ ID NO: 70), VISKDGTNAH (SEQ ID NO: 71), and EGR-CIEEKCYSGQIDY (SEQ ID NO: 80). The light chain CDRs of the 5P9 antibody have the following sequences per Chothia definition: RASQSVGRYMA (SEQ ID NO: 74), DASIRAT (SEQ ID NO: 75), and QQRSSWPPLT (SEQ ID NO: 76).

The 9C16 antibody includes a heavy chain variable region (SEQ ID NO: 84) encoded by the nucleic acid sequence shown below in SEQ ID NO: 83, and a light chain variable region (SEQ ID NO: 91) encoded by the nucleic acid sequence shown in SEQ ID NO: 90.

The heavy chain CDRs of the 9C16 antibody have the following sequences per Kabat definition: SDYGMH (SEQ ID NO: 85), VISKDGTNTHYADSVRG (SEQ ID NO: 86), and DGKCPDLKCYSGLIDY (SEQ ID NO: 87). The light chain CDRs of the 9C16 antibody have the following sequences per Kabat definition: RASQSVGGYLA (SEQ ID NO: 43), DASKRAT (SEQ ID NO: 92), and HQRSSWPPLT (SEQ ID NO: 93).

The heavy chain CDRs of the 9C16 antibody have the following sequences per Chothia definition: GLTFSD (SEQ ID NO: 88), VISKDGTNTH (SEQ ID NO: 89), and DGKCP-DLKCYSGLIDY (SEQ ID NO: 87). The light chain CDRs of the 9C16 antibody have the following sequences per Chothia definition: RASQSVGGYLA (SEQ ID NO: 43), DASKRAT (SEQ ID NO: 92), and HQRSSWPPLT (SEQ ID NO: 93).

An anti-CMV antibody contains a heavy chain variable having the amino acid sequence of SEQ ID NOS: 35, 47, 56, 67, 78, or 84 and a light chain variable having the amino acid sequence of SEQ ID NOS: 42, 52, 63, 73, 82, or 91. Preferably, the three heavy chain CDRs include an amino acid sequence at least 90%, 92%, 95%, 97% 98%, 99% or more identical to the amino acid sequence of SNHGIH (SEQ ID NO: 36), VISSDGDDDRYADSVKG (SEQ ID NO: 37), DGRCGEPKCYSGLPDY (SEQ ID NO: 38), SNYGMH (SEQ ID NO: 48), VISSDGSNEHYADSVKG (SEQ ID NO: 49), DGRCPDVNCYSGLIDY (SEQ ID NO: 50), SSNGIH (SEQ ID NO: 57), VISSDANDKQYADSVKG (SEQ ID NO: 58), DGTCSGGNCYSGLIDY (SEQ ID NO: 59), VISKDGTNAHYADSVRG (SEQ ID NO: 68), EGRCIEEN-CYSGQIDY (SEQ ID NO: 69), VISKDGTNAHYADS-VRGR (SEQ ID NO: 79), EGRCIEEKCYSGQIDY (SEQ ID NO: 80), SDYGMH (SEQ ID NO: 85), VISKDGTNTHY-ADSVRG (SEQ ID NO: 86), DGKCPDLKCYSGLIDY (SEQ ID NO: 87) (as determined by the Kabat method) or GFTFSN (SEQ ID NO: 39), VISSDGDDDR (SEQ ID NO: 40), DGRCGEPKCYSGLPDY (SEQ ID NO: 38), GLTFSN (SEQ ID NO: 39), VISSDGSNEH (SEQ ID NO: 51), DGRCPDVNCYSGLIDY (SEQ ID NO: 50), GFTFSS (SEQ ID NO: 60), VISSDANDKQ (SEQ ID NO: 61), DGTCSG-GNCYSGLIDY (SEQ ID NO: 59), KFIFSN (SEQ ID NO: 70), VISKDGTNAH (SEQ ID NO: 71), EGRCIEENCYSG-QIDY (SEQ ID NO: 69), EGRCIEEKCYSGQIDY (SEQ ID NO: 80), GLTFSD (SEQ ID NO: 88), VISKDGTNTH (SEQ ID NO: 89), DGKCPDLKCYSGLIDY (SEQ ID NO: 87), GLTFSN (SEQ ID NO: 118) (as determined by the Chothia method) and a light chain with three CDRs that include an amino acid sequence at least 90%, 92%, 95%, 97% 98%, 99% or more identical to the amino acid sequence of RASQSVG-GYLA (SEQ ID NO: 43), DASNRAT (SEQ ID NO: 44), LQRNTWPPLT (SEQ ID NO: 45), RASQSVGRYLA (SEQ ID NO: 53), QQRSNWPPLT (SEQ ID NO: 54), ASIRAT (SEQ ID NO: 64), HQRSNWPPLT (SEQ ID NO: 65), RASQSVGRYMA (SEQ ID NO: 74), DASIRAT (SEQ ID NO: 75), QQRSSWPPLT (SEQ ID NO: 76), DASKRAT (SEQ ID NO: 92), HQRSSWPPLT (SEQ ID NO: 93) (as determined by the Kabat method) or RASQSVGGYLA (SEQ ID NO: 43), DASNRAT (SEQ ID NO: 44), LQRNTWPPLT (SEQ ID NO: 45), RASQSVGRYLA (SEQ ID NO: 53), QQRSNWPPLT (SEQ ID NO: 54), ASIRAT (SEQ ID NO: 64), HQRSNWPPLT (SEQ ID NO: 65), RASQSVGRYMA (SEQ ID NO: 74), DASIRAT (SEQ ID NO: 75), QQRSSW-PPLT (SEQ ID NO: 76), DASKRAT (SEQ ID NO: 92), HQRSSWPPLT (SEQ ID NO: 93) (as determined by the Chothia method). The antibody binds CMV gB.

The heavy chain of an anti-CMV antibody is derived from a germ line V (variable) gene such as, for example, the IGHV3 germline gene.

The anti-CMV antibodies of the invention include a variable heavy chain ($V_H$) region encoded by a human IGHV3 germline gene sequence. IGHV3 germline gene sequences are shown, e.g., in Accession numbers M99663, X92214, L06616, L06617, M77327 and M77339. The anti-CMV antibodies of the invention include a $V_H$ region that is encoded by a nucleic acid sequence that is at least 80% homologous to the X germline gene sequence. Preferably, the nucleic acid sequence is at least 90%, 95%, 96%, 97% homologous to the IGHV3 germline gene sequence, and more preferably, at least 98%, 99% homologous to the IGHV3 germline gene sequence. The $V_H$ region of the anti-CMV antibody is at least 80% homologous to the amino acid sequence of the $V_H$ region encoded by the IGHV3 $V_H$ germline gene sequence. Preferably, the amino acid sequence of $V_H$ region of the anti-CMV antibody is at least 90%, 95%, 96%, 97% homologous to the amino acid sequence encoded by the IGHV3 germline gene sequence, and more preferably, at least 98%, 99% homologous to the sequence encoded by the IGHV3 germline gene sequence.

The anti-CMV antibodies of the invention also include a variable light chain ($V_L$) region encoded by a human IGKV3 germline gene sequence. A human IGKV3 $V_L$ germline gene sequence is shown, e.g., Accession numbers X01668, K02768, X17264, L19271, and L19272. Alternatively, the anti-CMV antibodies include a $V_L$ region that is encoded by a nucleic acid sequence that is at least 80% homologous to the IGKV3 germline gene sequence. Preferably, the nucleic acid sequence is at least 90%, 95%, 96%, 97% homologous to the IGKV3 germline gene sequence, and more preferably, at least 98%, 99% homologous to the IGKV3 germline gene sequence. The $V_L$ region of the anti-CMV antibody is at least 80% homologous to the amino acid sequence of the $V_L$ region encoded the IGKV3 germline gene sequence. Preferably, the amino acid sequence of $V_L$ region of the anti CMV antibody is at least 90%, 95%, 96%, 97% homologous to the amino acid sequence encoded by the IGKV3 germline gene sequence, and more preferably, at least 98%, 99% homologous to the sequence encoded by the IGKV3 germline gene sequence.

Unless otherwise defined, scientific and technical terms used in connection with the present invention have the meanings that are commonly understood by those of ordinary skill in the art. Further, unless otherwise required by context, singular terms include pluralities and plural terms include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein.

The practice of the present invention will employ, unless indicated specifically to the contrary, conventional methods of virology, immunology, microbiology, molecular biology and recombinant DNA techniques within the skill of the art, many of which are described below for the purpose of illustration. These techniques are explained fully in the literature. See, e.g., Sambrook, et al. Molecular Cloning: A Laboratory Manual (2nd Edition, 1989); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984).

The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

The following definitions are useful in understanding the present invention:

The term "antibody" (Ab) includes monoclonal antibodies, polyclonal antibodies, multispecific antibodies (e.g., bispecific antibodies), and antibody fragments, so long as they exhibit the desired biological activity. The term "immunoglobulin" (Ig) is used interchangeably with "antibody" herein.

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody is prepared by at least one purification step.

The basic four-chain antibody unit is a heterotetrameric glycoprotein composed of two identical light (L) chains and two identical heavy (H) chains. An IgM antibody consists of 5 of the basic heterotetramer unit along with an additional polypeptide called J chain, and therefore contain 10 antigen binding sites, while secreted IgA antibodies can polymerize to form polyvalent assemblages including 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H$1). Particular amino acid residues form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species are assigned to one of two clearly distinct types, called kappa (κ) and lambda (λ), based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha (α), delta (δ), epsilon (ε), gamma (γ) and mu (μ), respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" refers to the amino acid residues of an antibody that are responsible for antigen binding. The hypervariable region generally includes amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. e al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_H$ when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" refers to an antibody obtained from a population of substantially homogeneous antibodies, i.e., the individual antibodies including the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention are prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" are also isolated from phage antibody libraries using the techniques described in Clackson et al., Nature, 352:624-628 (1991) and Marks et al., J. Mol. Biol., 222:581-597 (1991), for example.

The monoclonal antibodies include "chimeric" antibodies, in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). The present invention provides variable domain antigen-binding sequences derived from human antibodies. Accordingly, chimeric antibodies of primary interest include antibodies containing one or more human antigen binding sequences (e.g., CDRs) and containing one or more sequences derived from a non-human antibody, e.g., an FR or C region sequence. In addition, chimeric antibodies of primary interest herein include those including a human variable domain antigen binding sequence of one antibody class or subclass and another sequence, e.g., FR or C region sequence, derived from another antibody class or subclass. Chimeric antibodies of interest also include those containing variable domain antigen-binding sequences related to those described herein or derived from a different species, such as a non-human primate (e.g., Old World Monkey, Ape, etc). Chimeric antibodies also include primatized and humanized antibodies.

Furthermore, chimeric antibodies may include residues that are not found in the recipient antibody or in the donor antibody. These modifications are made to further refine antibody performance. For further details, see Jones et al., Nature 321:522-525 (1986); Riechmann et al., Nature 332:323-329 (1988); and Presta, Curr. Op. Struct. Biol. 2:593-596 (1992).

A "humanized antibody" is generally considered to be a human antibody that has one or more amino acid residues introduced into it from a source that is non-human. These non-human amino acid residues are often referred to as "import" residues, which are typically taken from an "import" variable domain. Humanization is traditionally performed following the method of Winter and co-workers (Jones et al., Nature, 321:522-525 (1986); Reichmann et al., Nature, 332:323-327 (1988); Verhoeyen et al., Science, 239: 1534-1536 (1988)), by substituting import hypervariable region sequences for the corresponding sequences of a human antibody. Accordingly, these "humanized" antibodies are chimeric antibodies (U.S. Pat. No. 4,816,567), wherein substantially less than an intact human variable domain has been substituted by the corresponding sequence from a non-human species.

A "human antibody" is an antibody containing only sequences present in an antibody naturally produced by a human. Moreover, a human antibody of the invention is a native human antibody, in which the antibody is naturally occurring in a human, as opposed to a recombinant human antibody, in which the individual heavy and light chains are isolated from humans but are assembled randomly creating all forms of natural and unnatural antibodies (of which a negligible number of combinations have been isolated from a human).

Specifically, native human antibodies are those that arise naturally as the result of the functioning of an intact human immune system. The utility of native antibodies for the treatment of human viral diseases has been established through experience with hyperimmune human globulins. Native antibodies, as a class, differ in some respects from those obtained by recombinant library methods (phage or transgenic mouse) and possess distinct properties that may make them ideal therapeutics for human diseases. (See Dessain et al., Exploring the Native Human Antibody Repertoire to Create Antiviral Therapeutics in *Current Topics in Microbiology and Immunology* 317: 155-183 (2008), © Springer-Verlag New York). Specifically, there is a specific advantage of libraries of native antibodies expressed from human B cells over phage-derived antibodies, due to the limitations in a phage approach to recreate all of the original or native heavy chain: light chain pairings, thus preventing important antibody structures from being incorporated into a phage-generated library. Therefore, it is desirable to obtain high-quality native human antibodies expressed from human B cells for detection, diagnosis, treatment and therapy of pathogens by a high-throughput method.

Human antibodies of the invention, however, contain residues or modifications not found in a naturally occurring human antibody, including those modifications and variant sequences described herein. These are typically made to further refine or enhance antibody performance.

An "intact" antibody is one that comprises an antigen-binding site as well as a $C_L$ and at least heavy chain constant domains, $C_H1$, $C_H2$ and $C_H3$. The constant domains may be native sequence constant domains (e.g., human native sequence constant domains) or amino acid sequence variant thereof. Preferably, the intact antibody has one or more effector functions.

An "antibody fragment" includes a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

The phrase "functional fragment or analog" of an antibody is a compound having qualitative biological activity in common with a full-length antibody. For example, a functional fragment or analog of an anti-IgE antibody is one that can bind to an IgE immunoglobulin in such a manner so as to prevent or substantially reduce the ability of such molecule from having the ability to bind to the high affinity receptor, Fc$_\epsilon$RI.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment that roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

The "Fc" fragment includes the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv including only three CDRs specific for an antigen) has the ability to recognize and bind antigen, although at a lower affinity than the entire binding site.

"Single-chain Fv," also abbreviated as "sFv" or "scFv," are antibody fragments that contain the $V_H$ and $V_L$ antibody domains connected into a single polypeptide chain. Preferably, the sFv polypeptide further includes a polypeptide linker between the $V_H$ and $V_L$ domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

An antibody that "internalizes" is one that is taken up by (i.e., enters) the cell upon binding to an antigen on a mammalian cell (e.g., a cell surface polypeptide or receptor). The internalizing antibody includes antibody fragments, human or chimeric antibody, and antibody conjugates. For certain therapeutic applications, internalization in vivo is contemplated. The number of antibody molecules internalized is sufficient or adequate to kill a cell or inhibit its growth, especially an infected cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the infected cell.

An antibody is said to be "immunospecific," "specific for" or to "specifically bind" an antigen if it reacts at a detectable level with the antigen, preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$. Affinity of an antibody for its cognate antigen is also commonly expressed as a dissociation constant $K_D$, and in certain embodiments, HuM2e antibody specifically binds to M2e if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M. Affinities of antibodies are readily determined using conventional techniques, for example, those described by Scatchard et al. (*Ann. N.Y. Acad. Sci. USA* 51:660 (1949)).

Binding properties of an antibody to antigens, cells or tissues thereof are determined and assessed using immunodetection methods including, for example, immunofluorescence-based assays, such as immuno-histochemistry (IHC) and/or fluorescence-activated cell sorting (FACS).

An antibody having a "biological characteristic" of a designated antibody is one that possesses one or more of the biological characteristics of that antibody which distinguish it from other antibodies. For example, in certain embodiments, an antibody with a biological characteristic of a designated antibody binds the same epitope as that bound by the designated antibody and/or have a common effector function as the designated antibody.

The term "antagonist" antibody is used in the broadest sense, and includes an antibody that partially or fully blocks, inhibits, or neutralizes a biological activity of an epitope, polypeptide, or cell that it specifically binds. Methods for identifying antagonist antibodies include contacting a polypeptide or cell specifically bound by a candidate antagonist antibody with the candidate antagonist antibody and measuring a detectable change in one or more biological activities normally associated with the polypeptide or cell.

An antibody that "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). Preferably the cell is an infected cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation is evaluated by any increase in hypodiploid cells. Preferably, the antibody that induces apoptosis is one that results in about 2 to 50 fold, preferably about 5 to 50 fold, and most preferably about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or U.S. Pat. No. 5,821,337 may be performed. Useful effector cells for such assays include peripheral blood mononuclear cells (PBMC) and Natural Killer (NK) cells. Alternatively, or additionally, ADCC activity of the molecule of interest is assessed in vivo, e.g., in a animal model such as that disclosed in Clynes et al., PNAS (USA) 95:652-656 (1998).

"Fc receptor" or "FcR" describes a receptor that binds to the Fc region of an antibody. In certain embodiments, the FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FCγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (see review M. in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes that express one or more FcRs and perform effector functions. Preferably, the cells express at least FcγRIII and perform ADCC effector function. Examples of human leukocytes that mediate ADCC include PBMC, NK cells, monocytes, cytotoxic T cells and neutrophils; with PBMCs and NK cells being preferred. The effector cells are isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) that are bound to their cognate antigen. To assess complement activation, a CDC assay, e.g., as described in Gazzano-Santoro et al., J. Immunol. Methods 202:163 (1996), is performed.

The term "cytomegalovirus," also known as CMV, indicates a member of the herpesvirus family in any species, including human. CMV is also referred to as a Betaherpesvirinae, because it is a herpes virus that infects mononuclear cells and lymphocytes.

The term "human cytomegalovirus, or HCMV" indicates a member of the CMV family that infects humans. HCMV is a beta human herpesvirus with a genome size of 230 Kbp, coding more than 70 viral proteins. HCMV is also designated as human herpesvirus 5 (HHV-5).

A "mammal" for purposes of treating an infection, refers to any mammal, including humans, domestic and farm animals, and zoo, sports, or pet animals, such as dogs, cats, cattle, horses, sheep, pigs, goats, rabbits, etc. Preferably, the mammal is human.

"Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an infection if, after receiving a therapeutic amount of an antibody according to the methods of the present invention, the patient shows observable and/or measurable reduction in or absence of one or more of the following: reduction in the number of infected cells or absence of the infected cells; reduction in the percent of total cells that are infected; and/or relief to some extent, one or more of the symptoms associated with the specific infection; reduced morbidity and mortality, and improvement in quality of life issues. The above parameters for assessing successful treatment and improvement in the disease are readily measurable by routine procedures familiar to a physician.

The term "therapeutically effective amount" refers to an amount of an antibody or a drug effective to "treat" a disease or disorder in a subject or mammal. See preceding definition of "treating."

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

Administration "in combination with" one or more further therapeutic agents includes simultaneous (concurrent) and consecutive administration in any order.

"Carriers" include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ polyethylene glycol (PEG), and PLURONICS™.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Sm^{153}$, $Bi^{212}$, $P^{32}$ and radioactive isotopes of Lu), chemotherapeutic agents e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below.

A "growth inhibitory agent" refers to a compound or composition which inhibits growth of a cell, either in vitro or in vivo. Examples of growth inhibitory agents include agents that block cell cycle progression, such as agents that induce G1 arrest and M-phase arrest. Classical M-phase blockers include the vinca alkaloids (vincristine, vinorelbine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (W B Saunders: Philadelphia, 1995), especially p. 13. The taxanes (paclitaxel and docetaxel) are anticancer drugs both derived from the yew tree. Docetaxel (TAXOTERE™, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Label" refers to a detectable compound or composition that is conjugated directly or indirectly to the antibody so as to generate a "labeled" antibody. The label is detectable by itself (e.g., radioisotope labels or fluorescent labels) or, in the case of an enzymatic label, catalyzes chemical alteration of a substrate compound or composition that is detectable.

The term "epitope tagged" refers to a chimeric polypeptide including a polypeptide fused to a "tag polypeptide." The tag polypeptide has enough residues to provide an epitope against which an antibody can be made, yet is short enough such that it does not interfere with activity of the polypeptide to which it is fused. The tag polypeptide is also preferably fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

A "small molecule" is defined to have a molecular weight below about 500 Daltons.

The terms "nucleic acid" and "polynucleotide" are used interchangeably to refer to single- or double-stranded RNA, DNA, or mixed polymers. Polynucleotides include genomic sequences, extra-genomic and plasmid sequences, and smaller engineered gene segments that express, or are adapted to express polypeptides.

An "isolated nucleic acid" is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. A substantially pure nucleic acid includes isolated forms of the nucleic acid. Of course, this refers to the nucleic acid as originally isolated and does not exclude genes or sequences later added to the isolated nucleic acid by the hand of man.

The term "polypeptide" is used in its conventional meaning, i.e., as a sequence of amino acids. The polypeptides are not limited to a specific length of the product. Peptides, oligopeptides, and proteins are included within the definition of polypeptide, and such terms are used interchangeably unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences including CDRs and being capable of binding CMV or a CMV-infected cell.

An "isolated polypeptide" is one that has been identified and separated and/or recovered from a component of its natural environment. In preferred embodiments, the isolated polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated polypeptide includes the polypeptide in situ within recombinant cells since at least one component of the polypeptide's natural environment is not present. Ordinarily, however, isolated polypeptide is prepared by at least one purification step.

A "native sequence" polynucleotide is one that has the same nucleotide sequence as a polynucleotide derived from nature. A "native sequence" polypeptide is one that has the same amino acid sequence as a polypeptide (e.g., antibody) derived from nature (e.g., from any species). Such native sequence polynucleotides and polypeptides are isolated from nature or are produced by recombinant or synthetic means.

A polynucleotide "variant," is a polynucleotide that typically differs from a polynucleotide specifically disclosed in one or more substitutions, deletions, additions and/or insertions. Such variants are naturally occurring or synthetically generated, for example, by modifying one or more of the polynucleotide sequences of the invention and evaluating one or more biological activities of the encoded polypeptide as described herein and/or using any of a number of techniques well known in the art.

A polypeptide "variant" is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating one or more biological activities of the polypeptide as described herein and/or using any of a number of techniques well known in the art.

Modifications are made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art typically changes one or more of the codons of the encoding DNA sequence.

For example, certain amino acids are substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes are made in the peptide sequences of the disclosed compositions, or corresponding DNA sequences that encode said peptides without appreciable loss of their biological utility or activity.

In many instances, a polypeptide variant contains one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

In making such changes, the hydropathic index of amino acids is considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions are further made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants are also (or alternatively) modified by, for example, the deletion or addition of amino acids that have minimal influence on the immunogenicity, secondary structure and hydropathic nature of the polypeptide.

Polypeptides include a signal (or leader) sequence at the N-terminal end of the protein, which co-translationally or post-translationally directs transfer of the protein. The polypeptide may also be conjugated, e.g. fused in frame to a linker or other sequence for ease of synthesis, purification or identification of the polypeptide (e.g., poly-His), or to enhance binding of the polypeptide to a solid support. For example, a polypeptide is conjugated to an immunoglobulin Fc region.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" refers to a segment of at least about 20 contiguous positions, usually 30 to about 75, 40 to about 50, in which a sequence is compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison is conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85:2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 are used, for example with the parameters described herein, to determine percent sequence identity for the polynucleotides and polypeptides of the invention. Software for performing BLAST analyses is publicly available through the National Center for Biotechnology Information.

In one illustrative example, cumulative scores are calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

"Homology" refers to the percentage of residues in the polynucleotide or polypeptide sequence variant that are identical to the non-variant sequence after aligning the sequences and introducing gaps, if necessary, to achieve the maximum percent homology. In particular embodiments, polynucleotide and polypeptide variants have at least 70%, at least 75%, at least 80%, at least 90%, at least 95%, at least 98%, or at least 99% polynucleotide or polypeptide homology with a polynucleotide or polypeptide described herein.

"Vector" includes shuttle and expression vectors. Typically, the plasmid construct will also include an origin of replication (e.g., the ColE1 origin of replication) and a selectable marker (e.g., ampicillin or tetracycline resistance), for replication and selection, respectively, of the plasmids in bacteria. An "expression vector" refers to a vector that contains the necessary control sequences or regulatory elements for expression of the antibodies including antibody fragment of the invention, in bacterial or eukaryotic cells. Suitable vectors are disclosed below.

As used in this specification and the appended claims, the singular forms "a," "an" and "the" include plural references unless the content clearly dictates otherwise.

Antibodies

The present invention also provides CMV- and CMV-specific antibodies including a polypeptide of the present invention, including those polypeptides encoded by a polynucleotide sequence set forth in Example 1 and amino acid sequences set forth in Example 1 and FIG. 1, and fragments and variants thereof. In one embodiment, the antibody is an antibody designated herein as 2F10, 2M16, 2N9, 3C21, 4P12, 5P9, or 9C16. These antibodies preferentially bind to or specifically bind to CMV-infected cells as compared to uninfected control cells of the same cell type. In preferred embodiments, these antibodies bind to the glycoprotein B (gB) of CMV. In particular embodiments, the antibodies of the present invention bind to the CMV gp116 epitope AD2 site I having the amino acid sequence, SHRANETIYNTTLKYGDTTGTNTTK (SEQ ID NO: 31).

As will be understood by the skilled artisan, general description of antibodies herein and methods of preparing and using the same also apply to individual antibody polypeptide constituents and antibody fragments.

The antibodies of the present invention are polyclonal or monoclonal antibodies. However, in preferred embodiments, they are monoclonal. In particular embodiments, antibodies of the present invention are human antibodies. Methods of producing polyclonal and monoclonal antibodies are known in the art and described generally, e.g., in U.S. Pat. No. 6,824,780. Typically, the antibodies of the present invention are produced recombinantly, using vectors and methods available in the art, as described further below. Human antibodies are also generated by in vitro activated B cells (see U.S. Pat. Nos. 5,567,610 and 5,229,275).

Human antibodies are also produced in transgenic animals (e.g., mice) that are capable of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice results in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); U.S. Pat. No. 5,545,807; and WO 97/17852. Such animals are genetically engineered to produce human antibodies including a polypeptide of the present invention.

In certain embodiments, antibodies of the present invention are chimeric antibodies that contain sequences derived from both human and non-human sources. In particular embodiments, these chimeric antibodies are humanized or Primatized™. In practice, humanized antibodies are typically human antibodies in which some hypervariable region residues and possibly some FR residues are substituted by residues from analogous sites in rodent antibodies.

In the context of the present invention, chimeric antibodies also include fully human antibodies wherein the human hypervariable region or one or more CDRs are retained, but one or more other regions of sequence have been replaced by corresponding sequences from a non-human animal.

The choice of non-human sequences, both light and heavy, to be used in making the chimeric antibodies is important to reduce antigenicity and human anti-non-human antibody responses when the antibody is intended for human therapeutic use. It is further important that chimeric antibodies retain high binding affinity for the antigen and other favorable biological properties. To achieve this goal, according to a preferred method, chimeric antibodies are prepared by a process of analysis of the parental sequences and various conceptual chimeric products using three-dimensional models of the parental human and non-human sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

As noted above, antibodies (or immunoglobulins) can be divided into five different classes, based on differences in the amino acid sequences in the constant region of the heavy chains. All immunoglobulins within a given class have very similar heavy chain constant regions. These differences can be detected by sequence studies or more commonly by serological means (i.e. by the use of antibodies directed to these differences). Antibodies, or fragments thereof, of the present invention are any class, and may, therefore, have a gamma, mu, alpha, delta, or epsilon heavy chain. A gamma chain is gamma 1, gamma 2, gamma 3, or gamma 4; and an alpha chain is alpha 1 or alpha 2.

In a preferred embodiment, an antibody of the present invention, or fragment thereof, is an IgG. IgG is considered the most versatile immunoglobulin, because it is capable of carrying out all of the functions of immunoglobulin molecules. IgG is the major Ig in serum, and the only class of Ig that crosses the placenta. IgG also fixes complement, although the IgG4 subclass does not. Macrophages, monocytes, PMN's and some lymphocytes have Fc receptors for the Fc region of IgG. Not all subclasses bind equally well; IgG2 and IgG4 do not bind to Fc receptors. A consequence of binding to the Fc receptors on PMN's, monocytes and macrophages is that the cell can now internalize the antigen better. IgG is an opsonin that enhances phagocytosis. Binding of IgG to Fc receptors on other types of cells results in the activation of other functions. Antibodies of the present invention may be of any IgG subclass.

In another preferred embodiment, an antibody, or fragment thereof, of the present invention is an IgE. IgE is the least common serum Ig since it binds very tightly to Fc receptors on basophils and mast cells even before interacting with antigen. As a consequence of its binding to basophils an mast cells, IgE is involved in allergic reactions. Binding of the allergen to the IgE on the cells results in the release of various pharmacological mediators that result in allergic symptoms. IgE also plays a role in parasitic helminth diseases. Eosinophils have Fc receptors for IgE and binding of eosinophils to IgE-coated helminths results in killing of the parasite. IgE does not fix complement.

In various embodiments, antibodies of the present invention, and fragments thereof, contain a variable light chain that is either kappa or lambda. The lambda chain is any of subtype, including, e.g., lambda 1, lambda 2, lambda 3, and lambda 4.

As noted above, the present invention further provides antibody fragments including a polypeptide of the present invention. In certain circumstances there are advantages of using antibody fragments, rather than whole antibodies. For example, the smaller size of the fragments allows for rapid clearance, and lead to improved access to certain tissues, such as solid tumors. Examples of antibody fragments include: Fab, Fab', F(ab')$_2$ and Fv fragments; diabodies; linear antibodies; single-chain antibodies; and multispecific antibodies formed from antibody fragments.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from E. coli, thus allowing the facile production of large amounts of these fragments. Fab'-SH fragments can be directly recovered from E. coli and chemically coupled to form F(ab')$_2$ fragments (Carter et al., Bio/Technology 10:163-167 (1992)). According to another approach, F(ab')$_2$ fragments can be isolated directly from recombinant host cell culture. Fab and F(ab')$_2$ fragment with increased in vivo half-life including a salvage receptor binding epitope residues are described in U.S. Pat. No. 5,869,046. Other techniques for the production of antibody fragments will be apparent to the skilled practitioner.

In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions. Thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment is also a "linear antibody", e.g., as described in U.S. Pat. No. 5,641,870 for example. Such linear antibody fragments may be monospecific or bispecific.

In certain embodiments, antibodies of the present invention are bispecific or multi-specific. Bispecific antibodies are antibodies that have binding specificities for at least two different epitopes. Exemplary bispecific antibodies bind to two different epitopes of a single antigen. Other such antibodies combine a first antigen binding site with a binding site for a second antigen. Alternatively, an anti-CMV arm is combined with an arm that binds to a triggering molecule on a leukocyte, such as a T-cell receptor molecule (e.g., CD3), or Fc receptors for IgG (FcγR), such as FcγRI (CD64), FcγRII (CD32) and FcγRIII (CD16), so as to focus and localize cellular defense mechanisms to the infected cell. Bispecific antibodies are also used to localize cytotoxic agents to infected cells. These antibodies possess a CMV-binding arm and an arm that binds the cytotoxic agent (e.g., saporin, anti-interferon-α, vinca alkaloid, ricin A chain, methotrexate or radioactive isotope hapten). Bispecific antibodies are prepared as full length antibodies or antibody fragments (e.g., F(ab')$_2$ bispecific antibodies). WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, including at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate is coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies are made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., J. Exp. Med., 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

Antibodies with more than two valencies are contemplated. For example, trispecific antibodies are prepared. Tutt et al., J. Immunol. 147: 60 (1991). A multivalent antibody may be internalized (and/or catabolized) faster than a bivalent antibody by a cell expressing an antigen to which the antibodies bind. The antibodies of the present invention are multivalent antibodies with three or more antigen binding sites (e.g., tetravalent antibodies), which can be readily produced by recombinant expression of nucleic acid encoding the polypeptide chains of the antibody. The multivalent antibody contains a dimerization domain and three or more antigen binding sites. The preferred dimerization domain includes an Fc region or a hinge region. In this scenario, the antibody contains an Fc region and three or more antigen binding sites amino-terminal to the Fc region. The preferred multivalent antibody includes three to about eight, but preferably four, antigen binding sites. The multivalent antibody includes at least one polypeptide chain (and preferably two polypeptide chains), wherein the polypeptide chain(s) contains two or more variable domains. For instance, the polypeptide chain(s) includes VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) includes: VH-CH1-flexible linker-VH-CH1-Fc region chain; or VH-CH1-VH-CH1-Fc region chain. The multivalent antibody preferably further includes at least two (and preferably four) light chain variable domain polypeptides. The multivalent antibody, for instance, contains from about two to about eight light chain variable domain polypeptides. The light chain variable domain polypeptides contemplated here include a light chain variable domain and, optionally, further contain a $C_L$ domain.

Antibodies of the present invention further include single chain antibodies.

In particular embodiments, antibodies of the present invention are internalizing antibodies.

Amino acid sequence modification(s) of the antibodies described herein are contemplated. For example, the binding affinity and/or other biological properties of the antibody are improved. Amino acid sequence variants of the antibody are prepared by introducing appropriate nucleotide changes into a polynucleotide that encodes the antibody, or a chain thereof, or by peptide synthesis. Exemplary modifications include, for example, deletions from, and/or insertions into and/or substitutions of, residues within the amino acid sequences of the antibody. Any combination of deletion, insertion, and substitution is made to arrive at the final antibody, provided that the final construct possesses the desired characteristics. The amino acid changes also may alter post-translational processes of the antibody, such as changing the number or position of glycosylation sites. Any of the variations and modifications described above for polypeptides of the present invention are included in antibodies of the present invention.

A useful method for identification of certain residues or regions of an antibody that are preferred locations for mutagenesis is called "alanine scanning mutagenesis" as described by Cunningham and Wells in Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with PSCA antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of an antibody include the fusion to the N- or C-terminus of the antibody to an enzyme (e.g., for ADEPT) or a polypeptide that increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative and non-conservative substitutions are contemplated.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Any cysteine residue not involved in maintaining the proper conformation of the antibody is also substituted, generally with serine, to improve the oxidative stability of the molecule and prevent aberrant crosslinking Conversely, cysteine bond(s) are added to the antibody to improve its stability (particularly where the antibody is an antibody fragment such as an Fv fragment).

One type of substitutional variant involves substituting one or more hypervariable region residues of a parent antibody. Generally, the resulting variant(s) selected for further development has improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis is performed to identify hypervariable region residues contributing significantly to antigen binding. Alternatively, or additionally, a crystal structure of the antigen-antibody complex is analyzed to identify contact points between the antibody and an antigen or infected cell. These contact residues and neighboring residues are candidates for substitution according to the techniques elaborated herein. Once these variants are generated, the panel of variants is subjected to screening as described herein and antibodies with superior properties in one or more relevant assays are selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceyl-galactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration is also made by the addition of, or substitution by, one or more serine or threonine residues to the sequence of the original antibody (for O-linked glycosylation sites).

The antibody of the invention is modified with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) are introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med. 176: 1191-1195 (1992) and Shopes, B. J. Immunol. 148:2918-2922 (1992). Homodimeric antibodies with enhanced anti-infection activity are also prepared using heterobifunctional cross-linkers as described in Wolff et al., Cancer Research 53:2560-2565 (1993). Alternatively, an antibody is engineered which has dual Fc regions and thereby may have enhanced complement lysis and ADCC capabilities. See Stevenson et al., Anti-Cancer Drug Design 3:219-230 (1989).

To increase the serum half-life of the antibody, a salvage receptor binding epitope is incorporated into the antibody (especially an antibody fragment) as described in U.S. Pat. No. 5,739,277, for example. The term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Antibodies of the present invention are also modified to include an epitope tag or label, e.g., for use in purification or diagnostic applications. The invention also pertains to therapy with immunoconjugates including an antibody conjugated to an anti-cancer agent such as a cytotoxic agent or a growth inhibitory agent. Chemotherapeutic agents useful in the generation of such immunoconjugates have been described above.

Conjugates of an antibody and one or more small molecule toxins, such as a calicheamicin, maytansinoids, auristatin a trichothene, and CC1065, and the derivatives of these toxins that have toxin activity, are also contemplated herein.

In one preferred embodiment, an antibody (full length or fragments) of the invention is conjugated to one or more maytansinoid molecules. Maytansinoids are mitototic inhibitors that act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1. Liu et al., Proc. Natl. Acad. Sci. USA 93:8618-8623 (1996) described immunoconjugates including a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay.

Antibody-maytansinoid conjugates are prepared by chemically linking an antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody conjugates, including, for example, those disclosed in U.S. Pat. No. 5,208,020 or EP Patent 0 425 235 B1, and Chari et al., Cancer Research 52: 127-131 (1992). The linking groups include disufide groups, thioether groups, acid labile groups, photolabile groups, peptidase labile groups, or esterase labile groups, as disclosed in the above-identified patents, disulfide and thioether groups being preferred.

Immunoconjugates are made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio)propionate (SPDP) (Carlsson et al., Biochem. J. 173:723-737 [1978]) and N-succinimidyl-4-(2-pyridylthio)pentanoate (SPP) to provide for a disulfide linkage. For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker is a "cleavable linker" facilitating release of the cytotoxic drug in the cell. For example, an acid-labile linker, Cancer Research 52: 127-131 (1992); U.S. Pat. No. 5,208,020) may be used.

Another immunoconjugate of interest includes an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Another drug to which the antibody is conjugated is the antifolate, QFA. Both calicheamicin and QFA have intracellular sites of action and do not readily cross the plasma membrane. Therefore, cellular uptake of these agents through antibody mediated internalization greatly enhances their cytotoxic effects.

Examples of other agents that are conjugated to the antibodies of the invention include BCNU, streptozoicin, vincristine and 5-fluorouracil, the family of agents known collectively LL-E33288 complex described in U.S. Pat. Nos. 5,053, 394, 5,770,710, as well as esperamicins (U.S. Pat. No. 5,877, 296).

Enzymatically active toxins and fragments thereof that are used include, e.g., diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232.

The present invention further encompasses an immunoconjugate formed between an antibody and a compound with nucleolytic activity (e.g., a ribonuclease or a DNA endonuclease such as a deoxyribonuclease; DNase).

For selective destruction of infected cells, the antibody contain a highly radioactive atom. A variety of radioactive isotopes are available for the production of radioconjugated anti-PSCA antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for diagnosis, it contains a radioactive atom for scintigraphic studies, for example $tc^{99m}$ or $I^{123}$, or a spin label for nuclear magnetic resonance (NMR) imaging (also known as magnetic resonance imaging, mri), such as iodine-123, iodine-131, indium-111, fluorine-19, carbon-13, nitrogen-15, oxygen-17, gadolinium, manganese or iron.

The radio- or other label is incorporated in the conjugate in known ways. For example, the peptide is biosynthesized or synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ are attached via a cysteine residue in the peptide. Yttrium-90 can be attached via a lysine residue. The IODOGEN method (Fraker et al. (1978) Biochem. Biophys. Res. Commun. 80: 49-57 is used to incorporate iodine-123. "Monoclonal Antibodies in Immunoscintigraphy" (Chatal, CRC Press 1989) describes other methods in detail.

Alternatively, a fusion protein including the antibody and cytotoxic agent is made, e.g., by recombinant techniques or peptide synthesis. The length of DNA includes respective regions encoding the two portions of the conjugate either adjacent one another or separated by a region encoding a linker peptide which does not destroy the desired properties of the conjugate.

The antibodies of the present invention are also used in antibody dependent enzyme mediated prodrug therapy (ADEPT) by conjugating the antibody to a prodrug-activating enzyme which converts a prodrug (e.g., a peptidyl chemotherapeutic agent, see WO81/01145) to an active anti-cancer drug (see, e.g., WO 88/07378 and U.S. Pat. No. 4,975,278).

The enzyme component of the immunoconjugate useful for ADEPT includes any enzyme capable of acting on a prodrug in such a way so as to convert it into its more active, cytotoxic form. Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, Nature 328: 457-458 (1987)). Antibody-abzyme conjugates can be prepared as described herein for delivery of the abzyme to a infected cell population.

The enzymes of this invention are covalently bound to the antibodies by techniques well known in the art such as the use of the heterobifunctional crosslinking reagents discussed above. Alternatively, fusion proteins including at least the antigen binding region of an antibody of the invention linked to at least a functionally active portion of an enzyme of the invention is constructed using recombinant DNA techniques well known in the art (see, e.g., Neuberger et al., Nature, 312: 604-608 (1984).

Other modifications of the antibody are contemplated herein. For example, the antibody is linked to one of a variety of nonproteinaceous polymers, e.g., polyethylene glycol, polypropylene glycol, polyoxyalkylenes, or copolymers of polyethylene glycol and polypropylene glycol. The antibody is also entrapped in microcapsules prepared, for example, by coacervation techniques or by interfacial polymerization (for example, hydroxymethylcellulose or gelatin-microcapsules and poly(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The antibodies disclosed herein may also be formulated as immunoliposomes. A "liposome" is a small vesicle composed of various types of lipids, phospholipids and/or surfactant that is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA, 82:3688 (1985); Hwang et al., Proc. Natl. Acad. Sci. USA, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes are generated by the reverse phase evaporation method with a lipid composition including phosphatidylcholine, cholesterol and PEG-derivatized phosphatidylethanolamine (PEG-PE). Liposomes are extruded through filters of defined pore size to yield liposomes with the desired a diameter. Fab' fragments of the antibody of the present invention can be conjugated to the liposomes as described in Martin et al., J. Biol. Chem. 257: 286-288 (1982) via a disulfide interchange reaction. A chemotherapeutic agent is optionally contained within the liposome. See Gabizon et al., J. National Cancer Inst. 81(19)1484 (1989).

Antibodies of the present invention, or fragments thereof, may possess any of a variety of biological or functional characteristics. In certain embodiments, these antibodies are CMV specific antibodies, indicating that they specifically bind to or preferentially bind to CMV or HCMV, respectively, as compared to other viruses.

In particular embodiments, an antibody of the present invention is an antagonist antibody, which partially or fully blocks or inhibits a biological activity of a polypeptide or cell to which it specifically or preferentially binds. In other embodiments, an antibody of the present invention is a growth inhibitory antibody, which partially or fully blocks or inhibits the growth of an infected cell to which it binds. In another embodiment, an antibody of the present invention induces apoptosis. In yet another embodiment, an antibody of the present invention induces or promotes antibody-dependent cell-mediated cytotoxicity or complement dependent cytotoxicity.

Polynucleotides

The present invention, in other aspects, provides polynucleotide compositions. In preferred embodiments, these polynucleotides encode a polypeptide of the present invention, e.g., a region of a variable chain of an antibody that binds to CMV. As will be also recognized by the skilled artisan, polynucleotides of the invention are single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials. Polynucleotides of the present invention are used, e.g., in hybridization assays to detect the presence of a CMV-specific antibody in a biological sample, and in the recombinant production of polypeptides of the present invention.

Therefore, according to another aspect of the present invention, polynucleotide compositions are provided that include some or all of a polynucleotide sequence set forth in Example 1, complements of a polynucleotide sequence set forth in Example 1, and degenerate variants of a polynucleotide sequence set forth in Example 1. In certain preferred embodiments, the polynucleotide sequences set forth herein encode polypeptides capable of preferentially binding an CMV-infected cell as compared to a normal control uninfected cell, including a polypeptide having a sequence set forth in Example 1 or FIG. 1. Furthermore, the present invention contemplates all polynucleotides that encode any polypeptide of the present invention.

In other related embodiments, the present invention provides polynucleotide variants having substantial identity to the sequences set forth in Example 1 (or a portion thereof encoding a variable region or functional domain), for example, those including at least 70% sequence identity, preferably at least 75%, 80%, 85%, 90%, 95%, 96%, 97%, 98%, or 99% or higher, sequence identity compared to a polynucleotide sequence of this invention (or fragment thereof that encodes a variable region or functional domain of a polypeptide of the present invention), as determined using the methods described herein, (e.g., BLAST analysis using standard parameters). One skilled in this art will recognize that these values can be appropriately adjusted to determine corresponding identity of proteins encoded by two nucleotide sequences by taking into account codon degeneracy, amino acid similarity, reading frame positioning, and the like.

Typically, polynucleotide variants contain one or more substitutions, additions, deletions and/or insertions, preferably such that the immunogenic binding properties of the polypeptide encoded by the variant polynucleotide is not substantially diminished relative to a polypeptide encoded by a polynucleotide sequence specifically set forth herein.

In additional embodiments, the present invention provides polynucleotide fragments including various lengths of contiguous stretches of sequence identical to or complementary to one or more of the sequences disclosed herein. For example, polynucleotides are provided by this invention that include at least about 10, 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60-65° C. or 65-70° C.

In preferred embodiments, the polypeptide encoded by the polynucleotide variant or fragment has the same binding specificity (i.e., specifically or preferentially binds to CMV) as the polypeptide encoded by the native polynucleotide. In certain preferred embodiments, the polynucleotides described above, e.g., polynucleotide variants, fragments and hybridizing sequences, encode polypeptides that have a level of binding activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, are combined with other DNA sequences, such as promoters, polyadenylation signals, additional restriction enzyme sites, multiple cloning sites, other coding segments, and the like, such that their overall length varies considerably. A nucleic acid fragment of almost any length is employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are useful in many implementations of this invention.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that encode a polypeptide of the present invention but which vary due to differences in codon usage are specifically contemplated by the present invention. Further, alleles of the genes including the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles are identified using standard techniques (such as hybridization, amplification and/or database sequence comparison).

In certain embodiments of the present invention, the inventors contemplate the mutagenesis of the disclosed polynucleotide sequences to alter one or more properties of the encoded polypeptide, such as its binding specificity or binding strength. Techniques for mutagenesis are well-known in the art, and are widely used to create variants of both polypeptides and polynucleotides. A mutagenesis approach, such as site-specific mutagenesis, is employed for the preparation of variants and/or derivatives of the polypeptides described herein. By this approach, specific modifications in a polypeptide sequence are made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences include the nucleotide sequence of the desired mutation, as well as a sufficient number of adjacent nucleotides, to provide a primer sequence of sufficient size and sequence complexity to form a stable duplex on both sides of the deletion junction being traversed. Mutations are employed in a selected polynucleotide sequence to improve, alter, decrease, modify, or otherwise change the properties of the polynucleotide itself, and/or alter the properties, activity, composition, stability, or primary sequence of the encoded polypeptide.

In other embodiments of the present invention, the polynucleotide sequences provided herein are used as probes or primers for nucleic acid hybridization, e.g., as PCR primers. The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers for use in preparing other genetic constructions. As such, it is contemplated that nucleic acid segments that include a sequence region of at least about 15 nucleotide long contiguous sequence that has the same sequence as, or is complementary to, a 15 nucleotide long contiguous sequence disclosed herein are particularly useful. Longer contiguous identical or complementary sequences, e.g., those of about 20, 30, 40, 50, 100, 200, 500, 1000 (including all intermediate lengths) and even up to full length sequences are also used in certain embodiments.

Polynucleotide molecules having sequence regions including contiguous nucleotide stretches of 10-14, 15-20, 30, 50, or even of 100-200 nucleotides or so (including intermediate lengths as well), identical or complementary to a polynucleotide sequence disclosed herein, are particularly contemplated as hybridization probes for use in, e.g., Southern and Northern blotting, and/or primers for use in, e.g., polymerase chain reaction (PCR). The total size of fragment, as well as the size of the complementary stretch(es), will ultimately depend on the intended use or application of the particular nucleic acid segment. Smaller fragments are used in hybridization embodiments, wherein the length of the contiguous complementary region may be varied, such as between about 15 and about 100 nucleotides, but larger contiguous complementarity stretches may be used, according to the length complementary sequences to be detected.

The use of a hybridization probe of about 15-25 nucleotides in length allows the formation of a duplex molecule that is both stable and selective. Molecules having contiguous complementary sequences over stretches greater than 12 bases in length are generally preferred, though, in order to increase stability and selectivity of the hybrid, and thereby improve the quality and degree of specific hybrid molecules obtained. Nucleic acid molecules having gene-complementary stretches of 15 to 25 contiguous nucleotides, or even longer, are preferred.

Hybridization probes are selected from any portion of any of the sequences disclosed herein. All that is required is to review the sequences set forth herein, or to any continuous portion of the sequences, from about 15-25 nucleotides in length up to and including the full length sequence, that one wishes to utilize as a probe or primer. The choice of probe and primer sequences may be governed by various factors. For example, one may wish to employ primers from towards the termini of the total sequence.

Polynucleotides of the present invention, or fragments or variants thereof, are readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202, by introducing selected sequences into recombinant vectors for recombinant production, and by other recombinant DNA techniques generally known to those of skill in the art of molecular biology.

Vectors, Host Cells and Recombinant Methods

The invention provides vectors and host cells including a nucleic acid of the present invention, as well as recombinant techniques for the production of a polypeptide of the present invention. Vectors of the invention include those capable of replication in any type of cell or organism, including, e.g., plasmids, phage, cosmids, and mini chromosomes. In various embodiments, vectors including a polynucleotide of the present invention are vectors suitable for propagation or replication of the polynucleotide, or vectors suitable for expressing a polypeptide of the present invention. Such vectors are known in the art and commercially available.

Polynucleotides of the present invention are synthesized, whole or in parts that are then combined, and inserted into a vector using routine molecular and cell biology techniques, including, e.g., subcloning the polynucleotide into a linearized vector using appropriate restriction sites and restriction enzymes. Polynucleotides of the present invention may be amplified by polymerase chain reaction using oligonucleotide primers complementary to each strand of the polynucleotide. These primers may also include restriction enzyme cleavage sites to facilitate subcloning into a vector. The replicable vector components generally include, but are not limited to, one or more of the following: a signal sequence, an origin of replication, and one or more marker or selectable genes.

In order to express a polypeptide of the present invention, the nucleotide sequences encoding the polypeptide, or functional equivalents, are inserted into an appropriate expression vector, i.e., a vector that contains the necessary elements for the transcription and translation of the inserted coding sequence. Methods well known to those skilled in the art are used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J., et al. (2001) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems are utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

Within one embodiment, the variable regions of a gene expressing a monoclonal antibody of interest are amplified from a hybridoma cell using nucleotide primers. These primers may be synthesized by one of ordinary skill in the art, or may be purchased from commercially available sources (see, e.g., Stratagene (La Jolla, Calif.), which sells primers for amplifying mouse and human variable regions. The primers are used to amplify heavy or light chain variable regions, which are then inserted into vectors such as ImmunoZAP™ H or ImmunoZAP™ L (Stratagene), respectively. These vectors are then introduced into E. coli, yeast, or mammalian-based systems for expression. Large amounts of a single-chain protein containing a fusion of the $V_H$ and $V_L$ domains may be produced using these methods (see Bird et al., Science 242: 423-426 (1988)).

The "control elements" or "regulatory sequences" present in an expression vector are those non-translated regions of the vector, e.g., enhancers, promoters, 5' and 3' untranslated regions, that interact with host cellular proteins to carry out transcription and translation. These elements may vary in their strength and specificity. Depending on the vector system and host utilized, any number of suitable transcription and translation elements, including constitutive and inducible promoters, are used.

Examples of promoters suitable for use with prokaryotic hosts include the phoa promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also usually contain a Shine-Dalgarno sequence operably linked to the DNA encoding the polypeptide. Inducible promoters such as the hybrid lacZ promoter of the pBLUESCRIPT phagemid (Stratagene, La Jolla, Calif.) or pSPORT1 plasmid (Gibco BRL, Gaithersburg, Md.) and the like may be used.

A variety of promoter sequences are known for eukaryotes and any may be used according to the present invention. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

In mammalian cell systems, promoters from mammalian genes or from mammalian viruses are generally preferred. Polypeptide expression from vectors in mammalian host cells may be controlled, for example, by promoters obtained from the genomes of viruses such as polyoma virus, fowlpox virus, adenovirus (e.g., Adenovirus 2), bovine papilloma virus, avian sarcoma virus, cytomegalovirus (CMV), a retrovirus, hepatitis-B virus and most preferably Simian Virus 40 (SV40), from heterologous mammalian promoters, e.g., the actin promoter or an immunoglobulin promoter, and from heat-shock promoters, provided such promoters are compatible with the host cell systems. If it is necessary to generate a cell line that contains multiple copies of the sequence encoding a polypeptide, vectors based on SV40 or EBV may be advantageously used with an appropriate selectable marker. One example of a suitable expression vector is pcDNA3.1 (Invitrogen, Carlsbad, Calif.), which includes a CMV promoter.

A number of viral-based expression systems are available for mammalian expression of polypeptides. For example, in cases where an adenovirus is used as an expression vector, sequences encoding a polypeptide of interest are ligated into an adenovirus transcription/translation complex consisting of the late promoter and tripartite leader sequence. Insertion in a non-essential E1 or E3 region of the viral genome is used to obtain a viable virus that is capable of expressing the polypeptide in infected host cells (Logan, J. and Shenk, T. (1984) Proc. Natl. Acad. Sci. 81:3655-3659). In addition, transcription enhancers, such as the Rous sarcoma virus (RSV) enhancer, are used to increase expression in mammalian host cells.

In bacterial systems, any of a number of expression vectors are selected depending upon the use intended for the expressed polypeptide. For example, when large quantities are desired, vectors that direct high level expression of fusion proteins that are readily purified are used. Such vectors include, but are not limited to, the multifunctional E. coli cloning and expression vectors such pET (Stratagene), in which the sequence encoding the polypeptide of interest is ligated into the vector in frame with sequences for the amino-terminal Met and the subsequent 7 residues of β-galactosidase, so that a hybrid protein is produced; pIN vectors (Van Heeke, G. and S. M. Schuster (1989) J. Biol. Chem. 264: 5503-5509); and the like. pGEX Vectors (Promega, Madison, Wis.) are also used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin, or factor Xa protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH are used. Examples of other suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. For reviews, see Ausubel et al. (supra) and Grant et al. (1987) Methods Enzymol. 153:516-544. Other yeast promoters that are inducible promoters having the additional advantage of transcription controlled by growth conditions include the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

In cases where plant expression vectors are used, the expression of sequences encoding polypeptides are driven by any of a number of promoters. For example, viral promoters such as the 35S and 19S promoters of CaMV are used alone or in combination with the omega leader sequence from TMV (Takamatsu, N. (1987) EMBO J. 6:307-311. Alternatively, plant promoters such as the small subunit of RUBISCO or heat shock promoters may be used (Coruzzi, G. et al. (1984) EMBO J. 3:1671-1680; Broglie, R. et al. (1984) Science 224:838-843; and Winter, J., et al. (1991) Results Probl. Cell Differ. 17:85-105). These constructs are introduced into plant cells by direct DNA transformation or pathogen-mediated transfection. Such techniques are described in a number of generally available reviews (see, e.g., Hobbs, S. or Murry, L. E. in McGraw Hill Yearbook of Science and Technology (1992) McGraw Hill, New York, N.Y.; pp. 191-196).

An insect system is also used to express a polypeptide of interest. For example, in one such system, Autographa californica nuclear polyhedrosis virus (AcNPV) is used as a vector to express foreign genes in Spodoptera frugiperda cells or in Trichoplusia larvae. The sequences encoding the polypeptide may be cloned into a non-essential region of the virus, such as the polyhedrin gene, and placed under control of the polyhedrin promoter. Successful insertion of the polypeptide-encoding sequence renders the polyhedrin gene inactive and produce recombinant virus lacking coat protein. The recombinant viruses may then be used to infect, for example, S. frugiperda cells or Trichoplusia larvae in which the polypeptide of interest may be expressed (Engelhard, E. K. et al. (1994) Proc. Natl. Acad. Sci. 91:3224-3227).

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed.

However, in cases where only coding sequence, or a portion thereof, is inserted, exogenous translational control signals including the ATG initiation codon are provided. Furthermore, the initiation codon is in the correct reading frame to ensure correct translation of the inserted polynucleotide. Exogenous translational elements and initiation codons may be of various origins, both natural and synthetic.

Transcription of a DNA encoding a polypeptide of the invention is often increased by inserting an enhancer sequence into the vector. Many enhancer sequences are known, including, e.g., those identified in genes encoding globin, elastase, albumin, α-fetoprotein, and insulin. Typically, however, an enhancer from a eukaryotic cell virus is used. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the polypeptide-encoding sequence, but is preferably located at a site 5' from the promoter.

Expression vectors used in eukaryotic host cells (yeast, fungi, insect, plant, animal, human, or nucleated cells from other multicellular organisms) typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-PSCA antibody. One useful transcription termination component is the bovine growth hormone polyadenylation region. See WO94/11026 and the expression vector disclosed therein.

Suitable host cells for cloning or expressing the DNA in the vectors herein are the prokaryote, yeast, plant or higher eukaryote cells described above. Examples of suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

*Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Pichia methanolica, Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

In certain embodiments, a host cell strain is chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing that cleaves a "prepro" form of the protein may also be used to facilitate correct insertion, folding and/or function. Different host cells such as CHO, COS, HeLa, MDCK, HEK293, and WI38, which have specific cellular machinery and characteristic mechanisms for such post-translational activities, may be chosen to ensure the correct modification and processing of the foreign protein.

Methods and reagents specifically adapted for the expression of antibodies or fragments thereof are also known and available in the art, including those described, e.g., in U.S. Pat. Nos. 4,816,567 and 6,331,415. In various embodiments, antibody heavy and light chains, or fragments thereof, are expressed from the same or separate expression vectors. In one embodiment, both chains are expressed in the same cell, thereby facilitating the formation of a functional antibody or fragment thereof.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in infected cell destruction. For expression of antibody fragments and polypeptides in bacteria, see, e.g., U.S. Pat. Nos. 5,648,237, 5,789,199, and 5,840,523, which describes translation initiation region (TIR) and signal sequences for optimizing expression and secretion. After expression, the antibody is isolated from the *E. coli* cell paste in a soluble fraction and is purified through, e.g., a protein A or G column depending on the isotype. Final purification is carried out using a process similar to that used for purifying antibody expressed e.g., in CHO cells.

Suitable host cells for the expression of glycosylated polypeptides and antibodies are derived from multicellular organisms. Examples of invertebrate cells include plant such as for example lemna and insect cells. Numerous baculoviral strains and variants and corresponding permissive insect host cells from hosts such as *Spodoptera frugiperda* (caterpillar), *Aedes aegypti* (mosquito), *Aedes albopicius* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco are also used as hosts.

Propagation of antibody polypeptides and fragments thereof in vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/–DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for polypeptide production and cultured in conventional nutrient media modified as appropriate for inducing promoters, selecting transformants, or amplifying the genes encoding the desired sequences.

For long-term, high-yield production of recombinant proteins, stable expression is generally preferred. For example, cell lines that stably express a polynucleotide of interest may be transformed using expression vectors that may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223-32) and adenine phosphoribosyltransferase (Lowy, I. et al. (1990) *Cell* 22:817-23) genes that are employed in tk⁻ or aprt⁻ cells, respectively. Also, antimetabolite, antibiotic or herbicide resistance are used as the basis for selection; for example, dhfr which confers resistance to methotrexate (Wigler, M. et al. (1980) *Proc. Natl. Acad. Sci.* 77:3567-70); npt, which confers resistance to the aminoglycosides, neomycin and G-418 (Colbere-Garapin, F. et al. (1981) *J. Mol. Biol.* 150:1-14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) *Proc. Natl. Acad. Sci.* 85:8047-51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121-131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence are identified by a variety of procedures known to those of skill in the art. These procedures include, but are not limited to, DNA-DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; J. Exp. Med. 158:1211-1216).

Various labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which are used include radionuclides, enzymes, fluorescent, chemiluminescent, or chromogenic agents as well as substrates, cofactors, inhibitors, magnetic particles, and the like.

The polypeptide produced by a recombinant cell is secreted or contained intracellularly depending on the sequence and/or the vector used. As will be understood by those of skill in the art, expression vectors containing polynucleotides of the invention may be designed to contain signal sequences that direct secretion of the encoded polypeptide through a prokaryotic or eukaryotic cell membrane.

In certain embodiments, a polypeptide of the present invention is produce as a fusion polypeptide further including a polypeptide domain that will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Amgen, Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 or more histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3:263-281) while the enterokinase cleavage site provides a means for purifying the desired polypeptide from the fusion protein. A discussion of vectors useful for producing fusion proteins is provided in Kroll, D. J. et al. (1993; *DNA Cell Biol.* 12:441-453).

In certain embodiments, a polypeptide of the present invention is fused with a heterologous polypeptide, which may be a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells, the signal sequence may be selected, for example, from the group of the alkaline phosphatase, penicillinase, 1 pp, or heat-stable enterotoxin II leaders. For yeast secretion, the signal sequence may be selected from, e.g., the yeast invertase leader, α factor leader (including Saccharomyces and Kluyveromyces α factor leaders), or acid phosphatase leader, the C. albicans glucoamylase leader, or the signal described in WO 90/13646. In mammalian cell expression, mammalian signal sequences as well as viral secretory leaders, for example, the herpes simplex gD signal, are available.

When using recombinant techniques, the polypeptide or antibody can be produced intracellularly, in the periplasmic space, or directly secreted into the medium. If the polypeptide or antibody is produced intracellularly, as a first step, the particulate debris, either host cells or lysed fragments, are removed, for example, by centrifugation or ultrafiltration. Carter et al., Bio/Technology 10:163-167 (1992) describe a procedure for isolating antibodies that are secreted to the periplasiic space of E. coli. Briefly, cell paste is thawed in the presence of sodium acetate (pH 3.5), EDTA, and phenylmethylsulfonylfluoride (PMSF) over about 30 min. Cell debris can be removed by centrifugation. Where the polypeptide or antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The polypeptide or antibody composition prepared from the cells can be purified using, for example, hydroxyapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the polypeptide or antibody. Protein A can be used to purify antibodies or fragments thereof that are based on human $\gamma_1$, $\gamma_2$, or $\gamma_4$ heavy chains (Lindmark et al., J. Immunol. Meth. 62:1-13 (1983)). Protein G is recommended for all mouse isotypes and for human $\gamma_3$ (Guss et al., EMBO J. 5:15671575 (1986)). The matrix to which the affinity ligand is attached is most often agarose, but other matrices are available. Mechanically stable matrices such as controlled pore glass or poly(styrenedivinyl) benzene allow for faster flow rates and shorter processing times than can be achieved with agarose. Where the polypeptide or antibody includes a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the polypeptide or antibody to be recovered.

Following any preliminary purification step(s), the mixture including the polypeptide or antibody of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Compositions

The present invention further includes pharmaceutical formulations including a polypeptide, antibody, or modulator of the present invention, at a desired degree of purity, and a pharmaceutically acceptable carrier, excipient, or stabilizer (Remingion's Pharmaceutical Sciences 16th edition, Osol, A. Ed. (1980)). In certain embodiments, pharmaceutical formulations are prepared to enhance the stability of the polypeptide or antibody during storage, e.g., in the form of lyophilized formulations or aqueous solutions.

Acceptable carriers, excipients, or stabilizers are nontoxic to recipients at the dosages and concentrations employed, and include, e.g., buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g. Zn-protein complexes); and/or non-ionic surfactants such as TWEEN™, PLURONICS™ or polyethylene glycol (PEG). In certain embodiments, the therapeutic formulation preferably includes the polypeptide or antibody at a concentration of between 5-200 mg/ml, preferably between 10-100 mg/ml.

The formulations herein may also contain one or more additional therapeutic agents suitable for the treatment of the particular indication, e.g., infection being treated, or to prevent undesired side-effects. Preferably, the additional therapeutic agent has an activity complementary to the polypeptide or antibody of the resent invention, and the two do not adversely affect each other. For example, in addition to the polypeptide or antibody of the present invention, it may be desirable to include in the one formulation, e.g., an additional antibody, anti-viral agent, anti-infective agent and/or cardioprotectant. Such molecules are suitably present in the pharmaceutical formulation in amounts that are effective for the purpose intended.

The active ingredients, e.g., polypeptides and antibodies of the present invention and other therapeutic agents, may also be entrapped in microcapsules prepared, for example, by coacervation techniques or by interfacial polymerization, for example, hydroxymethylcellulose or gelatin-microcapsules and polymethylmethacylate) microcapsules, respectively, in colloidal drug delivery systems (for example, liposomes, albumin microspheres, microemulsions, nano-particles and nanocapsules) or in macroemulsions. Such techniques are disclosed in Remingion's Pharmaceutical Sciences 16th edition, Osol, A. Ed. (1980).

Sustained-release preparations may be prepared. Suitable examples of sustained-release preparations include semi-permeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxyburyric acid.

Formulations to be used for in vivo administration are preferably sterile. This is readily accomplished by filtration through sterile filtration membranes.

Diagnostic Uses

The antibodies and fragments thereof of the present invention specifically bind or preferentially bind to CMV-infected cells or tissue, as compared to normal control cells and tissue. Thus, the antibodies of the present invention may be used to detect infected cells or tissues in a patient, biological sample, or cell population, using any of a variety of diagnostic and prognostic methods, including those described herein. The ability of an anti-CMV antibody to detect infected cells will depend, of course, upon its binding specificity, which may be readily determined by testing its ability to bind to infected cells or tissues obtained from different patients, and/or from patients infected with different strains of CMV.

Diagnostic methods generally involve contacting a biological sample obtained from a patient, such as, e.g., blood, serum, saliva, urine, sputum, a cell swab sample, or a tissue biopsy, with a CMV-specific antibody and determining whether the antibody preferentially binds to the sample as compared to a control sample or predetermined cut-off value, thereby indicating the presence of infected cells. In particular embodiments, at least two-fold, three-fold, or five-fold more CMV-specific antibody binds to an infected cell as compared to an appropriate control normal cell or tissue sample. A pre-determined cut-off value may be determined, e.g., by averaging the amount of CMV-specific antibody that binds to several different appropriate control samples under the same conditions used to perform the diagnostic assay of the biological sample being tested.

Bound antibody may be detected using procedures described herein and known in the art. In certain embodiments, diagnostic methods of the present invention are practiced using CMV-specific antibodies that are conjugated to a detectable label, e.g., a fluorophore, to facilitate detection of bound antibody. However, they may also be practiced using methods of secondary detection of the CMV-specific antibody. These include, for example, RIA, ELISA, precipitation, agglutination, complement fixation and immuno-fluorescence.

In certain procedures, the CMV-specific antibodies are labeled. The label may be detected directly, such as radiolabels and fluorochromes, or they may be moieties, such as enzymes, that must be reacted or derivatized to be detected. Examples of isotope labels are $^{99}$Tc, $^{14}$C, $^{131}$I, $^{125}$I, $^{3}$H, $^{32}$P and $^{35}$S. Fluorescent materials that may be used include, for example, fluorescein and its derivatives, rhodamine and its derivatives, auramine, dansyl, umbelliferone, luciferia, 2,3-dihydrophthalazinediones, horseradish peroxidase, alkaline phosphatase, lysozyme, and glucose-6-phosphate dehydrogenase.

An enzyme label can be detected by any of the currently utilized colorimetric, spectrophotometric, fluorospectrophotometric or gasometric techniques. Many enzymes which can be used in these procedures are known and can be utilized. Examples are peroxidase, alkaline phosphatase, β-glucuronidase, β-D-glucosidase, β-D-galactosidase, urease, glucose oxidase plus peroxidase, galactose oxidase plus peroxidase and acid phosphatase.

The antibodies may be tagged with such labels by known methods. For instance, coupling agents such as aldehydes, carbodiimides, dimaleimide, imidates, succinimides, biddiazotized benzadine and the like may be used to tag the antibodies with the above-described fluorescent, chemiluminescent, and enzyme labels. An enzyme is typically combined with an antibody using bridging molecules such as carbodiimides, periodate, diisocyanates, glutaraldehyde and the like. Various labeling techniques are described in Morrison, Methods in Enzymology 32b, 103 (1974), Syvanen et al., J. Biol. Chem. 284, 3762 (1973) and Bolton and Hunter, Biochem J. 133, 529 (1973).

CMV-specific antibodies of the present invention are capable of differentiating between patients with and without a CMV infection, and determining whether a patient has an infection, using the representative assays provided herein. According to one method, a biological sample is obtained from a patient suspected of having or known to have CMV infection. In preferred embodiments, the biological sample includes cells from the patient. The sample is contacted with a CMV-specific antibody, e.g., for a time and under conditions sufficient to allow the CMV-specific antibody to bind to infected cells present in the sample. The amount of bound CMV-specific antibody is determined and compared to a control value, which may be, e.g., a pre-determined value or a value determined from normal tissue sample. An increased amount of antibody bound to the patient sample as compared to the control sample is indicative of the presence of infected cells in the patient sample.

In a related method, a biological sample obtained from a patient is contacted with a CMV-specific antibody for a time and under conditions sufficient to allow the antibody to bind to infected cells. Bound antibody is then detected, and the presence of bound antibody indicates that the sample contains infected cells. This embodiment is particularly useful when the CMV-specific antibody does not bind normal cells at a detectable level.

In certain embodiments, antibodies that bind to an infected cell will preferably generate a signal indicating the presence of an infection in at least about 20% of patients with the infection being detected, more preferably at least about 30% of patients. Alternatively, or in addition, the antibody will generate a negative signal indicating the absence of the infection in at least about 90% of individuals without the infection being detected. Each antibody should satisfy the above criteria; however, those of ordinary skill in the art will recognize that antibodies of the present invention may be used in combination to improve sensitivity.

The present invention also includes kits useful in performing diagnostic and prognostic assays using the antibodies of the present invention. These kits will include a suitable container including one or more CMV-specific antibody of the present invention in labeled or unlabeled form. In addition, if the antibody is supplied in a labeled form suitable for an indirect binding assay, the kit may further include reagents useful in performing the appropriate indirect assay. For example, the kit may include one or more suitable containers including enzyme substrates or derivatizing agents, depending on the nature of the label. Control samples and/or instructions may also be included.

Therapeutic Uses

CMV-specific antibodies and fragments thereof of the present invention specifically bind or preferentially bind to infected cells, as compared to normal control uninfected cells and tissue. Thus, these CMV-specific antibodies may be used to selectively target infected cells or tissues in a patient, biological sample, or cell population. In light of the infection-specific binding properties of these antibodies, the present invention provides methods of regulating (e.g., inhibiting) the growth of infected cells, methods of killing infected cells, and methods of inducing apoptosis of infected cells. These methods all include contacting an infected cell with a CMV-specific antibody of the present invention. These methods may be practiced in vitro, ex vivo, and in vivo.

Pharmaceutical compositions of the invention are administered to targeted patient populations, including, but not limited to, the very old and the very young, immunocompromised subjects (e.g., subjects with HIV/AIDS, another immunosuppressive disease, or a genetic disorder that leads to an insufficient or compromised immune system), transplant recipients (including whole organ, tissue, and, particularly, those patients receiving a transplant or replacement of a hematopoietic stem cell population or bone marrow), subjects receiving immunosuppressive therapy (for example, subjects who are medicated for conditions such as arthritis, transplant rejection, and cancer), and CMV-negative pregnant women who are at risk of exposure to or infection with CMV (CMV is passed to the fetus of these subjects causing deafness and cognitive deficiency in nearly 1% of all births).

In various embodiments, the antibodies are therapeutically active themselves intrinsically, and/or they are conjugated to a cytotoxic agent or growth inhibitory agent, e.g., a radioisotope or toxin, that is useful in treating infected cells bound by the antibody.

In one embodiment, the present invention provides methods of treating or preventing infection in a patient, which include providing a CMV-specific antibody of the present invention to a patient diagnosed with, at risk of developing, or suspected of having a CMV infection. The methods of the present invention may be used in the first-line treatment of the infection, follow-on treatment, or in the treatment of a relapsed or refractory infection. Treatment with an antibody of the invention may be a stand-alone treatment, or it may be one component or phase of a combination therapy regime, in which one or more additional therapeutic agents are also used to treat the patient.

For in vivo treatment of human and non-human patients, the patient is usually administered a pharmaceutical formulation including a CMV-specific antibody of the present invention. When used for in vivo therapy, the antibodies of the subject invention are administered to the patient in therapeutically effective amounts (i.e., amounts that eliminate or reduce the patient's viral burden). The antibodies are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. The antibodies may be administered parenterally, when possible, at the target cell site, or intravenously. Intravenous or subcutaneous administration of the antibody is preferred in certain embodiments.

For parenteral administration, the antibodies may be formulated in a unit dosage injectable form (solution, suspension, emulsion) in association with a pharmaceutically acceptable, parenteral vehicle. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The antibodies will typically be formulated in such vehicles at concentrations of about 1 mg/ml to 10 mg/ml.

The dose and dosage regimen will depend upon a variety of factors readily determined by a physician, such as the nature of the infection and the characteristics of the particular cytotoxic agent or growth inhibitory agent conjugated to the antibody (when used), e.g., its therapeutic index, the patient, and the patient's history. Generally, a therapeutically effective amount of an antibody is administered to a patient. In particular embodiments, the amount of antibody administered will typically be in the range of about 0.1 to about 50 mg/kg of patient body weight. Depending on the type and severity of the infection, about 0.1 mg/kg to about 50 mg/kg body weight (e.g., about 0.1-15 mg/kg/dose) of antibody can be an initial candidate dosage for administration to the patient, whether, for example, by one or more separate administrations, or by continuous infusion. The progress of this therapy can be readily monitored by conventional methods and assays and based on criteria known to the physician or other persons of skill in the art.

In one particular embodiment, an immunoconjugate including the antibody conjugated with a cytotoxic agent is administered to the patient. Preferably, the immunoconjugate is internalized by the cell, resulting in increased therapeutic efficacy of the immunoconjugate in killing the cell to which it binds. In one embodiment, the cytotoxic agent targets or interferes with the nucleic acid in the infected cell. Examples of such cytotoxic agents are described above and include maytansinoids, calicheamicins, ribonucleases and DNA endonucleases.

Other therapeutic regimens may be combined with the administration of a CMV-specific antibody of the present invention. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

In certain embodiments, it is desirable to combine administration of an antibody of the present invention with another antibody directed against another antigen associated with the infectious agent.

Aside from administration of the antibody protein to the patient, the present application contemplates administration of the antibody by gene therapy. Such administration of nucleic acid encoding the antibody is encompassed by the expression "administering a therapeutically effective amount of an antibody". See, for example, PCT Patent Application Publication WO96/07321 concerning the use of gene therapy to generate intracellular antibodies.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

Example 1

Production of Anti-CMV Antibodies

Human monoclonal antibodies specific for CMV were recombinantly produced as described below.

89 human plasma samples were screened for the presence of CMV antibodies by ELISA using a polypeptide corresponding to the CMV gp116 epitope AD2 site having the amino acid sequence, SHRANETIYNTTLKYGDTTGT-NTTK (SEQ ID NO: 31). Two plasma samples tested positive, indicating the presence of anti-CMV gp116 antibodies.

PBMC were obtained from a donor blood sample with a high IgG titer to the CMV gp 116 epitope AD2. CD 19+ cells were enriched and mixed with a biotinylated form of the CMV gp116 AD2 peptide, and antigen-specific B cells were enriched using streptavidin coated microbeads. These antigen-selected B cells were plated in microtiter dishes at a density of greater than 1 cell per well and cultured under conditions favorable for B cell proliferation and activation to generate antibody-producing B cells, e.g., in the presence of a B cell mitogen, such as lipopolysaccharide (LPS) or CD40 ligand. Cell supernatants obtained from the B cells were then tested for the presence of antibodies that bound the CMV gp116 epitope AD2, thereby identifying 11 wells containing B cells that produce antigen-specific antibodies.

Recombinant antibodies including antigen-binding regions of the antigen-specific antibodies were produced by subcloning the DNA encoding the variable regions of the antibody chains into the pcDNA3.1+ expression vector. Transient transfections were performed in 293 FT cells to reconstitute and recombinantly produce these antibodies. The recombinantly produced antibodies were then tested for their ability to bind CMV gp116 epitope AD2, and 7 recombinant IgGs that bound this antigen were identified. Two additional anti-CMV antibodies were subsequently generated according to these same methods. The binding affinity of the antibodies was determined as shown in Table 1.

TABLE 1

Binding Affinities of Anti-CMV Antibodies Sorted by $K_D$ and $k_{off}$

| CMV Antibody | Sorted by $K_D$ | | $K_D$ ($k_{off}/k_{on}$), nM |
|---|---|---|---|
| | $k_a$ ($M^{-1} s^{-1}$) × $10^5$ | $k_d$ ($s^{-1}$) | |
| mAb G-ITC88 | 7.67 (6) | 0.00116 (3) | 1.51 (5) |
| mAb A-2F10 | 5.62 (7) | 0.001112 (7) | 1.98 (2) |
| mAb E-5P9 | 2.45 (2) | 0.00121 (3) | 4.9 (1) |
| mAb F-9C16 | 5.83 (9) | 0.00286 (8) | 4.9 (2) |
| mAb B-2M16 | 27 (1) | 0.023 (1) | 8.47 (5) |
| mAb D-4P12 | 1.75 (1) | 0.00190 (3) | 10.9 (2) |
| mAb C-2N9 | 26 (1) | 0.030 (2) | 11.59 (7) |

| CMV Antibody | Sorted by $k_{off}$ | | $K_D$ ($k_{off}/k_{on}$), nM |
|---|---|---|---|
| | $k_a$ ($M^{-1} s^{-1}$) × $10^5$ | $k_d$ ($s^{-1}$) | |
| mAb A-2F10 | 5.62 (7) | 0.001112 (7) | 1.98 (2) |
| mAb G-ITC88 | 7.67 (6) | 0.00116 (3) | 1.51 (5) |
| mAb E-5P9 | 2.45 (2) | 0.00121 (3) | 4.9 (1) |
| mAb D-4P12 | 1.75 (1) | 0.00190 (3) | 10.9 (2) |
| mAb F-9C16 | 5.83 (9) | 0.00286 (8) | 4.9 (2) |
| mAb B-2M16 | 27 (1) | 0.023 (1) | 8.47 (5) |
| mAb C-2N9 | 26 (1) | 0.030 (2) | 11.59 (7) |

Numbers in parentheses represents the standard error in the last reported digit.

The sequences of the antibodies were determined, including the sequences of the variable regions of the Gamma heavy and Kappa light chains of the antibodies designated 2F10, 2M16, 2N9, 3C21, 4P12, 5P9, 9C16. In addition, the sequence of each of the polynucleotides encoding the antibody sequences was determined. Shown below are the polypeptide and polynucleotide sequences of the gamma heavy chains and kappa light chains, with the signal peptides in bold at the N-terminus (or 5' end) and the constant regions in bold at the C-terminus (or 3' end) of the variable regions, which are shown in plain text.

2F10 gamma:
(SEQ ID NO: 1)

```
ATGGAGTTTGGGCTGAGCTGGGTTTTCCTCGTTGCTCTTTTAAGAGGTGTCCAGTGTCAGG

TACATCTGGTGGAGTCGGGGGGAGGCGTCGTCCAGCCTGGTAGGGCCCTGAGACTCTCCTG

TGCAGCCACTGGATTCACATTTAGTAATCACGGCATACATTGGGTCCGCCAGGCTCCAGGC

AAGGGGCTGGAGTGGCTGGCAGTTATTTCAAGCGATGGAGATGATGACCGTTACGCAGACT

CCGTGAAGGGTCGATTCAGCGTCTCCAGAGACAATTCCAAGAACACCGTGCATCTGCAGAT

GAATGGCCTGAGACCTGACGACACGGCTATTTATTTCTGTGCGCGAGATGGGAGGTGTGGT

GAACCTAAGTGCTACTCAGGGTTGCCTGATTACTGGGGCCGGGGGACCCTGGTCACCGTCT

CGAGCGCCTCCACCAAGGGCCCATCGGTCTTCCCCCTGGCACCCTCCTCCAAGAGCACCTC

TGGGGGCACAGCGGCCCTGGGCTGCCTGGTCAAGGACTACTTCCCCGAACCGGTGACGGTG

TCGTGGAACTCAGGCGCCCTGACCAGCGGCGTGCACACCTTCCCGGCTGTCCTACAGTCCT

CAGGACTCTACTCCCTCAGCAGCGTGGTGACCGTGCCCTCAGCAGCTTGGGCACCCAGAC

CTACATCTGCAACGTGAATCACAAGCCCAGCAACACCAAGGTGGACAAGAGAGTTGAGCCC

AAATCTTGTGACAAAACTCACACATGCCCACCGTGCCCAGCACCTGAACTCCTGGGGGGAC

CGTCAGTCTTCCTCTTCCCCCCAAAACCCAAGGACACCCTCATGATCTCCCGGACCCCTGA

GGTCACATGCGTGGTGGTGGACGTGAGCCACGAAGACCCTGAGGTCAAGTTCAACTGGTAC

GTGGACGGCGTGGAGGTGCATAATGCCAAGACAAAGCCGCGGGAGGAGCAGTACAACAGCA

CGTACCGTGTGGTCAGCGTCCTCACCGTCCTGCACCAGGACTGGCTGAATGGCAAGGAGTA

CAAGTGCAAGGTCTCCAACAAAGCCCTCCCAGCCCCCATCGAGAAAACCATCTCCAAAGCC

AAAGGGCAGCCCCGAGAACCACAGGTGTACACCCTGCCCCCATCCCGGGAGGAGATGACCA

AGAACCAGGTCAGCCTGACCTGCCTGGTCAAAGGCTTCTATCCCAGCGACATCGCCGTGGA
```

```
GTGGGAGAGCAATGGGCAGCCGGAGAACAACTACAAGACCACGCCTCCCGTGCTGGACTCC

GACGGCTCCTTCTTCCTCTATAGCAAGCTCACCGTGGACAAGAGCAGGTGGCAGCAGGGGA

ACGTCTTCTCATGCTCCGTGATGCATGAGGCTCTGCACAACCACTACACGCAGAAGAGCCT

CTCCCTGTCTCCGGGTAAA
```

2F10 gamma variable region:
(SEQ ID NO: 34)

```
CAGGTACATCTGGTGGAGTCGGGGGGAGGCGTCGTCCAGCCTGGTAGGGCCCTGAGACTCT

CCTGTGCAGCCACTGGATTCACATTTAGTAATCACGGCATACATTGGGTCCGCCAGGCTCC

AGGCAAGGGGCTGGAGTGGCTGGCAGTTATTTCAAGCGATGGAGATGATGACCGTTACGCA

GACTCCGTGAAGGGTCGATTCAGCGTCTCCAGAGACAATTCCAAGAACACCGTGCATCTGC

AGATGAATGGCCTGAGACCTGACGACACGGCTATTTATTTCTGTGCGCGAGATGGGAGGTG

TGGTGAACCTAAGTGCTACTCAGGGTTGCCTGATTACTGGGGCCGGGGGACCCTGGTCACC

GTCTCG
```

2F10 gamma:
(SEQ ID NO: 2)

MEFGLSWVFLVALLRGVQCQVHLVESGGGVVQPGRALRLSCAATGFTFSNHGIHWVRQAPG

KGLEWLAVISSDGDDDRYADSVKGRFSVSRDNSKNTVHLQMNGLRPDDTAIYFCARDGRCG

EPKCYSGLPDYWGRGTLVTVS**SASTKGPSVFPLAPSSKSTSGGTAALGCLVKDYFPEPVTV

SWNSGALTSGVHTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIEKTISKA

KGQPREPQVYTLPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGK**

2F10 gamma variable region: (Kabat CDRs underlined,
Chothia CDRs in bold italics):
(SEQ ID NO: 35)

QVHLVESGGGVVQPGRALRLSCAAT*GFTFSN*HGIHWVRQAPGKGLEWLA*VISSDGDDDR*YA

DSVKGRFSVSRDNSKNTVHLQMNGLRPDDTAIYFCAR*DGRCGEPKCYSGLPDY*WGRGTLVT

VS

2F10 gamma heavy chain Kabat CDRs:
CDR 1:
(SEQ ID NO: 36)
SNHGIH

CDR 2:
(SEQ ID NO: 37)
VISSDGDDDRYADSVKG

CDR 3:
(SEQ ID NO: 38)
DGRCGEPKCYSGLPDY

2F10 gamma heavy chain Chothia CDRs:
CDR 1:
(SEQ ID NO: 39)
GFTFSN

CDR 2:
(SEQ ID NO: 40)
VISSDGDDDR

CDR 3:
(SEQ ID NO: 38)
DGRCGEPKCYSGLPDY

2F10 kappa:
(SEQ ID NO: 3)
ATGGAAGCCCCAGCGCAGCTTCTCTTCCTCCTGCTACTCTGGCTCCCAGCTACCACCGGAG

-continued

```
AGATTGTTTTGACACAGTCTCCAGCCACCCTGTCTTTGTCTCCAGGGGACAGAGCCACCCT

CTCCTGCAGGGCCAGTCAGAGTGTTGGCGGGTACTTAGCCTGGTATCAACAAAAGCCTGGC

CAGGCTCCCAGGCTCCTCCTCTATGATGCATCCAACAGGGCCACTGGCATCCCAGCCAGGT

TCAGTGGCAGTGGGTCTGGGACAGACTTCACTCTCACCATCAGCAGCCTAGAGCCTGAAGA

TTTTGCACTTTATTACTGTCTTCAGCGTAACACGTGGCCTCCGCTCACTTTCGGGGGAGGG

ACCAAGGTGGAGATCAAACGTACGGTGGCTGCACCATCTGTCTTCATCTTCCCGCCATCTG

ATGAGCAGTTGAAATCTGGAACTGCCTCTGTTGTGTGCCTGCTGAATAACTTCTATCCCAG

AGAGGCCAAAGTACAGTGGAAGGTGGATAACGCCCTCCAATCGGGTAACTCCCAGGAGAGT

GTCACAGAGCAGGACAGCAAGGACAGCACCTACAGCCTCAGCAGCACCCTGACGCTGAGCA

AAGCAGACTACGAGAAACACAAAGTCTACGCCTGCGAAGTCACCCATCAGGGCCTGAGCTC

GCCCGTCACAAAGAGCTTCAACAGGGGAGAGTGT
```

2F10 kappa variable region:
(SEQ ID NO: 41)
```
GAGATTGTTTTGACACAGTCTCCAGCCACCCTGTCTTTGTCTCCAGGGGACAGAGCCACCC

TCTCCTGCAGGGCCAGTCAGAGTGTTGGCGGGTACTTAGCCTGGTATCAACAAAAGCCTGG

CCAGGCTCCCAGGCTCCTCCTCTATGATGCATCCAACAGGGCCACTGGCATCCCAGCCAGG

TTCAGTGGCAGTGGGTCTGGGACAGACTTCACTCTCACCATCAGCAGCCTAGAGCCTGAAG

ATTTTGCACTTTATTACTGTCTTCAGCGTAACACGTGGCCTCCGCTCACTTTCGGGGGAGG

GACCAAGGTGGAGATCAAACGTACG
```

2F10 Kappa:
(SEQ ID NO: 4)
MEAPAQLLFLLLLWLPATTGEIVLTQSPATLSLSPGDRATLSCRASQSVGGYLAWYQQKPG

QAPRLLLYDASNRATGIPARFSGSGSGTDFTLTISSLEPEDFALYYCLQRNTWPPLTFGGG

TKVEIKRTVAAPSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRGEC

2F10 Kappa variable region (Kabat CDRs underlined,
Chothia CDRs in bold italics):
(SEQ ID NO: 42)
EIVLTQSPATLSLSPGDRATLSC*RASQSVGGYLA*WYQQKPGQAPRLLLY*DASNRAT*GIPAR

FSGSGSGTDFTLTISSLEPEDFALYYC*LQRNTWPPLT*FGGGTKVEIKRT

2F10 kappa light chain Kabat CDRs:
CDR 1:
(SEQ ID NO: 43)
RASQSVGGYLA

CDR 2:
(SEQ ID NO: 44)
DASNRAT

CDR 3:
(SEQ ID NO: 45)
LQRNTWPPLT

2F10 kappa light chain Chothia CDRs:
CDR 1:
(SEQ ID NO: 43)
RASQSVGGYLA

CDR 2:
(SEQ ID NO: 44)
DASNRAT

CDR 3:
(SEQ ID NO: 45)
LQRNTWPPLT

2M16 gamma:
(SEQ ID NO: 5)
ATGGAGTTGGGGCTGTGCTGGGTTTTCCTCGTTGCTCTTTTAAGAGGTGTCCAGTGCCAGG

TGCAGCTGGTGGACTCTGGGGGAGGCATGGTCCAGCCTGGGAGGTCCCTGAGACTCTCCTG

TTCAGCCTCTGGACTCACCTTCAGCAATTATGGCATGCACTGGGTCCGCCAGGCTCCAGGC

AAGGGGCTGGAGTGGGTGGCAGTTATATCAAGTGATGGAAGTAATGAGCACTACGCAGACT

CCGTGAAGGGCCGATTCACTATCTCCAGAGACAATTTCAACAACATGCTGTATCTGCAAAT

GAACAGCCTGAGAGCTGAGGACACGGCTGTCTATTACAGTGCGAGAGATGGGAGGTGTCCT

GATGTTAACTGCTACTCAGGGTTGATTGACTATTGGGGCCAGGGGACCCTGGTCACCGTCT

CGAGCGCCTCCACCAAGGGCCCATCGGTCTTCCCCCTGGCACCCTCCTCCAAGAGCACCTC

TGGGGGCACAGCGGCCCTGGGCTGCCTGGTCAAGGACTACTTCCCCGAACCGGTGACGGTG

TCGTGGAACTCAGGCGCCCTGACCAGCGGCGTGCACACCTTCCCGGCTGTCCTACAGTCCT

CAGGACTCTACTCCCTCAGCAGCGTGGTGACCGTGCCCTCCAGCAGCTTGGGCACCCAGAC

CTACATCTGCAACGTGAATCACAAGCCCAGCAACACCAAGGTGGACAAGAGAGTTGAGCCC

AAATCTTGTGACAAAACTCACACATGCCCACCGTGCCCAGCACCTGAACTCCTGGGGGGAC

CGTCAGTCTTCCTCTTCCCCCCAAAACCCAAGGACACCCTCATGATCTCCCGGACCCCTGA

GGTCACATGCGTGGTGGTGGACGTGAGCCACGAAGACCCTGAGGTCAAGTTCAACTGGTAC

GTGGACGGCGTGGAGGTGCATAATGCCAAGACAAAGCCGCGGGAGGAGCAGTACAACAGCA

CGTACCGTGTGGTCAGCGTCCTCACCGTCCTGCACCAGGACTGGCTGAATGGCAAGGAGTA

CAAGTGCAAGGTCTCCAACAAAGCCCTCCCAGCCCCCATCGAGAAAACCATCTCCAAAGCC

AAAGGGCAGCCCCGAGAACCACAGGTGTACACCCTGCCCCCATCCCGGGAGGAGATGACCA

AGAACCAGGTCAGCCTGACCTGCCTGGTCAAAGGCTTCTATCCCAGCGACATCGCCGTGGA

GTGGGAGAGCAATGGGCAGCCGGAGAACAACTACAAGACCACGCCTCCCGTGCTGGACTCC

GACGGCTCCTTCTTCCTCTATAGCAAGCTCACCGTGGACAAGAGCAGGTGGCAGCAGGGGA

ACGTCTTCTCATGCTCCGTGATGCATGAGGCTCTGCACAACCACTACACGCAGAAGAGCCT

CTCCCTGTCTCCGGGTAAA

2M16 gamma variable region:
(SEQ ID NO: 46)
CAGGTGCAGCTGGTGGACTCTGGGGGAGGCATGGTCCAGCCTGGGAGGTCCCTGAGACTCT

CCTGTTCAGCCTCTGGACTCACCTTCAGCAATTATGGCATGCACTGGGTCCGCCAGGCTCC

AGGCAAGGGGCTGGAGTGGGTGGCAGTTATATCAAGTGATGGAAGTAATGAGCACTACGCA

GACTCCGTGAAGGGCCGATTCACTATCTCCAGAGACAATTTCAACAACATGCTGTATCTGC

AAATGAACAGCCTGAGAGCTGAGGACACGGCTGTCTATTACAGTGCGAGAGATGGGAGGTG

TCCTGATGTTAACTGCTACTCAGGGTTGATTGACTATTGGGGCCAGGGGACCCTGGTCACC

GTCTCG

2M16 gamma:
(SEQ ID NO: 6)
MELGLCWVFLVALLRGVQCQVQLVDSGGGMVQPGRSLRLSCSASGLTFSNYGMHWVRQAPG

KGLEWVAVISSDGSNEHYADSVKGRFTISRDNFNNMLYLQMNSLRAEDTAVYYSARDGRCP

DVNCYSGLIDYWGQGTLVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIEKTISKA

KGQPREPQVYTLPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGK

2M16 gamma variable region (Kabat CDRs underlined,
Chothia CDRs in bold italics):
(SEQ ID NO: 47)
QVQLVDSGGGMVQPGRSLRLSCSAS*GLTFSN*YGMHWVRQAPGKGLEWVA*VISSDGSNEH*YA

DSVKGRFTISRDNFNNMLYLQMNSLRAEDTAVYYSAR*DGRCPDVNCYSGLIDY*WGQGTLVT

VS

2M16 gamma heavy chain Kabat CDRs:
CDR 1:
(SEQ ID NO: 48)
SNYGMH

CDR 2:
(SEQ ID NO: 49)
VISSDGSNEHYADSVKG

CDR 3:
(SEQ ID NO: 50)
DGRCPDVNCYSGLIDY

2M16 gamma heavy chain Chothia CDRs:
CDR 1:
(SEQ ID NO: 118)
GLTFSN

CDR 2:
(SEQ ID NO: 51)
VISSDGSNEH

CDR 3:
(SEQ ID NO: 50)
DGRCPDVNCYSGLIDY

2M16 kappa:
(SEQ ID NO: 7)
ATGGAAGCCCCAGCGCAGCTTCTCTTCCTCCTGCTACTCTGGCTCCCAGATACCACCGGAG

AAATTGTCTTGACACAGTCTCCAGCCACCCTGTCTTTGTCTCCAGGGGAAAGAGCCACCCT

CTCCTGCAGGGCCAGTCAGAGTGTTGGCAGATACTTAGCCTGGTACCAACAGAAAGGTGGC

CAGGCTCCCAGGCTCCTCATCTATGATGCATCCAACAGGGCCACTGGCATCCCAGCCAGGT

TCAGTGGCAGTGGGTCTGGGACAGACTTCACTCTCACCATCGACAGCCTAGAGCCTGAAGA

TTTTGCAGTTTATTACTGTCAGCAGCGTAGCAACTGGCCTCCGCTCACTTTCGGCGGAGGG

ACCAAGGTGGAGATCAAACGTACGGTGGCTGCACCATCTGTCTTCATCTTCCCGCCATCTG

ATGAGCAGTTGAAATCTGGAACTGCCTCTGTTGTGTGCCTGCTGAATAACTTCTATCCCAG

AGAGGCCAAAGTACAGTGGAAGGTGGATAACGCCCTCCAATCGGGTAACTCCCAGGAGAGT

GTCACAGAGCAGGACAGCAAGGACAGCACCTACAGCCTCAGCAGCACCCTGACGCTGAGCA

AAGCAGACTACGAGAAACACAAAGTCTACGCCTGCGAAGTCACCCATCAGGGCCTGAGCTC

GCCCGTCACAAAGAGCTTCAACAGGGGAGAGTGT

2M16 Kappa variable region:
(SEQ ID NO: 94)
GAAATTGTCTTGACACAGTCTCCAGCCACCCTGTCTTTGTCTCCAGGGGAAAGAGCCACCC

TCTCCTGCAGGGCCAGTCAGAGTGTTGGCAGATACTTAGCCTGGTACCAACAGAAAGGTGG

CCAGGCTCCCAGGCTCCTCATCTATGATGCATCCAACAGGGCCACTGGCATCCCAGCCAGG

TTCAGTGGCAGTGGGTCTGGGACAGACTTCACTCTCACCATCGACAGCCTAGAGCCTGAAG

ATTTTGCAGTTTATTACTGTCAGCAGCGTAGCAACTGGCCTCCGCTCACTTTCGGCGGAGG

GTCCAAGGTGGAGATCAAACGTACG

-continued

2M16 Kappa
(SEQ ID NO: 8)
MEAPAQLLFLLLLWLPDTTGEIVLTQSPATLSLSPGERATLSCRASQSVGRYLAWYQQKGG

QAPRLLIYDASNRATGIPARFSGSGSGTDFTLTIDSLEPEDFAVYYCQQRSNWPPLTFGGG

SKVEIKRTVAAPSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRGEC

2M16 Kappa variable region (Kabat CDRs underlined,
Chothia CDRs in bold italics):
(SEQ ID NO: 52)
EIVLTQSPATLSLSPGERATLSC<u>*RASQSVGRYLA*</u>WYQQKGGQAPRLLIY<u>*DASNRAT*</u>GIPAR FSGSGSGTDFTLTIDSLEPEDFAVYYC<u>*QQRSNWPPLT*</u>FGGGSKVEIKRT 2M16 kappa light chain Kabat CDRs:
CDR 1:
(SEQ ID NO: 53)
RASQSVGRYLA

CDR 2:
(SEQ ID NO: 44)
DASNRAT

CDR 3:
(SEQ ID NO: 54)
QQRSNWPPLT

2M16 kappa light chain Chothia CDRs:
CDR 1:
(SEQ ID NO: 53)
RASQSVGRYLA

CDR 2:
(SEQ ID NO: 44)
DASNRAT

CDR 3:
(SEQ ID NO: 54)
QQRSNWPPLT

2N9 gamma:
(SEQ ID NO: 9)
ATGGAGTTGGGGCTGCGCTGGGTTTTCCTCGTTGCTCTTTTAAGAGGTGTCCAGTGTCAGG

TGCAGCTGGTGGAGTCTGGGGGAGGCGTGGTCCAGCCTGGGAGGTCCCTGAGACTCTCCTG

TGCAGCCTCTGGATTCACCTTCAGTAGTAATGGCATACACTGGGTCCGCCAGGCTCCAGGC

AAGGGGCTGGAGTGGGTGGCAGTTATATCATCTGATGCAAATGATAAACAATACGCAGACT

CCGTGAAGGGCCGATTCACCATCTCCAGAGACAATTCCAAGAACATGGTGTATCTGCAAAT

GAACAGCCTGAGAGTTGAAGACACGGCTGTCTATTTCTGTGCGAGAGATGGGACGTGCAGT

GGTGGTAACTGCTACTCAGGGTTGATTGACTATTGGGGCCGGGGAATTCTGGTCACCGTCT

CGAGCGCCTCCACCAAGGGCCCATCGGTCTTCCCCCTGGCACCCTCCTCCAAGAGCACCTC

TGGGGGCACAGCGGCCCTGGGCTGCCTGGTCAAGGACTACTTCCCCGAACCGGTGACGGTG

TCGTGGAACTCAGGCGCCCTGACCAGCGGCGTGCACACCTTCCCGGCTGTCCTACAGTCCT

CAGGACTCTACTCCCTCAGCAGCGTGGTGACCGTGCCCTCCAGCAGCTTGGGCACCCAGAC

CTACATCTGCAACGTGAATCACAAGCCCAGCAACACCAAGGTGGACAAGAGAGTTGAGCCC

AAATCTTGTGACAAAACTCACACATGCCCACCGTGCCCAGCACCTGAACTCCTGGGGGGAC

CGTCAGTCTTCCTCTTCCCCCCAAAACCCAAGGACACCCTCATGATCTCCCGGACCCCTGA

GGTCACATGCGTGGTGGTGGACGTGAGCCACGAAGACCCTGAGGTCAAGTTCAACTGGTAC

GTGGACGGCGTGGAGGTGCATAATGCCAAGACAAAGCCGCGGGAGGAGCAGTACAACAGCA

CGTACCGTGTGGTCAGCGTCCTCACCGTCCTGCACCAGGACTGGCTGAATGGCAAGGAGTA

CAAGTGCAAGGTCTCCAACAAAGCCCTCCCAGCCCCCATCGAGAAAACCATCTCCAAAGCC

-continued

AAAGGGCAGCCCCGAGAACCACAGGTGTACACCCTGCCCCCATCCCGGGAGGAGATGACCA

AGAACCAGGTCAGCCTGACCTGCCTGGTCAAAGGCTTCTATCCCAGCGACATCGCCGTGGA

GTGGGAGAGCAATGGGCAGCCGGAGAACAACTACAAGACCACGCCTCCCGTGCTGGACTCC

GACGGCTCCTTCTTCCTCTATAGCAAGCTCACCGTGGACAAGAGCAGGTGGCAGCAGGGGA

ACGTCTTCTCATGCTCCGTGATGCATGAGGCTCTGCACAACCACTACACGCAGAAGAGCCT

CTCCCTGTCTCCGGGTAAA

2N9 gamma variable region:

(SEQ ID NO: 55)
CAGGTGCAGCTGGTGGAGTCTGGGGGAGGCGTGGTCCAGCCTGGGAGGTCCCTGAGACTCT

CCTGTGCAGCCTCTGGATTCACCTTCAGTAGTAATGGCATACACTGGGTCCGCCAGGCTCC

AGGCAAGGGGCTGGACTGGGTGGCAGTTATATCATCTGATGCAAATGATAAACAATACGCA

GACTCCGTGAAGGGCCGATTCACCATCTCCAGAGACAATTCCAAGAACATGGTGTATCTGC

AAATGAACAGCCTGAGAGTTGAAGACACGGCTGTCTATTTCTGTGCGAGAGATGGGACGTG

CAGTGGTGGTAACTGCTACTCAGGGTTGATTGACTATTGGGGCCGGGGAATTCTGGTCACC

GTCTCG

2N9 gamma (SEQ ID NO: 10)
MELGLRWVFLVALLRGVQCQVQLVESGGGVVQPGRSLRLSCAASGFTFSSNGIHWVRQAPG

KGLDWVAVISSDANDKQYADSVKGRFTISRDNSKNMVYLQMNSLRVEDTAVYFCARDGTCS

GGNCYSGLIDYWGRGILVTVS**SASTKGPSVFPLAPSSKSTSGGTAALGCLVKDYFPEPVTV

SWNSGALTSGVHTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIEKTISKA

KGQPREPQVYTLPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGK**

2N9 gamma variable region (Kabat CDRs underlined,
Chothia CDRs in bold italics):

(SEQ ID NO: 56)
QVQLVESGGGVVQPGRSLRLSCAAS*GFTFSS*NGIHWVRQAPGKGLDWVA*VISSDANDKQ*YA

DSVKGRFTISRDNSKNMVYLQMNSLRVEDTAVYFCAR*DGTCSGGNCYSGLIDY*WGRGILVT

VS

2N9 gamma heavy chain Kabat CDRs:
CDR 1:

(SEQ ID NO: 57)
SSNGIH

CDR 2:

(SEQ ID NO: 58)
VISSDANDKQYADSVKG

CDR 3:

(SEQ ID NO: 59)
DGTCSGGNCYSGLIDY

2N9 gamma heavy chain Chothia CDRs:
CDR 1:

(SEQ ID NO: 60)
GFTFSS

CDR 2:

(SEQ ID NO: 61)
VISSDANDKQ

-continued

CDR 3:
(SEQ ID NO: 59)
DGTCSGGNCYSGLIDY

2N9 kappa:
(SEQ ID NO: 11)
ATGGACATGAGGGTCCCAGCTCAGCTTCTCTTCCTCCTGCTACTCTGGCTCCCAGATACCA

CCGGAGAAATTGTGTTGACACAGTCTCCAGCCACCTTGTCTTTGTCTCCAGGTGAAAGAGC

CACCCTCTCCTGCAGGGCCAGTCAGAGTGTTGGCGGCTACTTAGCCTGGTACCAACAGAAA

CCTGGCCAGGCTCCCAGGCTCCTCATCTACGATGCCTCCATCAGGGCCACTGGCATCCCAG

CCAGGTTCAGTGGCAGTGGGTCTGGGACAGACTTCACTCTCACCATCAGCAGCCTAGAGCC

TGAAGATTTTGCAGTTTATTACTGTCACCAGCGTAGCAACTGGCCTCCGCTCACTTTCGGC

GGAGGGACCAAGGTGGATATCAAACGTACGGTGGCTGCACCATCTGTCTTCATCTTCCCGC

CATCTGATGAGCAGTTGAAATCTGGAACTGCCTCTGTTGTGTGCCTGCTGAATAACTTCTA

TCCCAGAGAGGCCAAAGTACAGTGGAAGGTGGATAACGCCCTCCAATCGGGTAACTCCCAG

GAGAGTGTCACAGAGCAGGACAGCAAGGACAGCACCTACAGCCTCAGCAGCACCCTGACGC

TGAGCAAAGCAGACTACGAGAAACACAAAGTCTACGCCTGCGAAGTCACCCATCAGGGCCT

GAGCTCGCCCGTCACAAAGAGCTTCAACAGGGGAGAGTGT

2N9 kappa variable region:
(SEQ ID NO: 62)
GAAATTGTGTTGACACAGTCTCCAGCCACCTTGTCTTTGTCTCCAGGTGAAAGAGCCACCC

TCTCCTGCAGGGCCAGTCAGAGTGTTGGCGGCTACTTAGCCTGGTACCAACAGAAACCTGG

CCAGGCTCCCAGGCTCCTCATCTACGATGCCTCCATCAGGGCCACTGGCATCCCAGCCAGG

TTCAGTGGCAGTGGGTCTGGGACAGACTTCACTCTCACCATCAGCAGCCTAGAGCCTGAAG

ATTTTGCAGTTTATTACTGTCACCAGCGTAGCAACTGGCCTCCGCTCACTTTCGGCGGAGG

GACCAAGGTGGATATCAAACGTACG

2N9 kappa:
(SEQ ID NO: 12)
MRVPAQLLFLLLLWLPDTTGEIVLTQSPATLSLSPGERATLSCRASQSVGGYLAWYQQKPG

QAPRLLIYDASIRATGIPARFSGSGSGTDFTLTISSLEPEDFAVYYCHQRSNWPPLTFGGG

TKVDIKRTVAAPSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRGEC

2N9 kappa variable region (Kabat CDRs underlined,
Chothia CDRs in bold italics):
(SEQ ID NO: 63)
EIVLTQSPAILSLSPGERATLSC*RASQSVGGYLA*WYQQKPGQAPRLLIYD*ASIRAT*GIPAR

FSGSGSGTDFTLTISSLEPEDFAVYYC*HQRSNWPPLT*FGGGTKVDIKRT

2N9 kappa light chain Kabat CDRs:
CDR 1:
(SEQ ID NO: 43)
RASQSVGGYLA

CDR 2:
(SEQ ID NO: 64)
ASIRAT

CDR 3:
(SEQ ID NO: 65)
HQRSNWPPLT

2N9 kappa light chain Chothia CDRs:
CDR 1:
(SEQ ID NO: 43)
RASQSVGGYLA

CDR 2:

(SEQ ID NO: 64)
ASIRAT

CDR 3:

(SEQ ID NO: 65)
HQRSNWPPLT

4P12 gamma:

(SEQ ID NO: 13)
ATGGAGTTGGGGCTGAGCTGGGTTTTCCTCGTTGCTCTTTTAAGAGGTGTCCAGTGTCAGG

TGCAGCTGGTGGAGTCGGGGGGAGGCGTGATCCAGCCTGGGAGGTCCCTGAGACTCTCCTG

TGTTGCCTCTAAATTCATCTTCAGTAACCATGGCATACACTGGGTCCGCCAGGCTCCAGGC

AAGGGGCTGGAGTGGGTGGCGGTTATATCAAAAGATGGGACTAATGCACACTACGCAGACT

CCGTGAGGGGCCGATTTAGCATCTCCAGAGACAACTCCAAGGACACTGTCTTTCTGGAAAT

GCGCAGCCTGCGACCTGAAGACACGGCTGTGTATTACTGTGCGAGAGAGGGCCGGTGTATT

GAAGAAAACTGCTACTCCGGACAGATTGACTATTGGGGCCAGGGATCCCTGGTCACCGTCT

CGAGCGCCTCCACCAAGGGCCCATCGGTCTTCCCCCTGGCACCCTCCTCCAAGAGCACCTC

TGGGGGCACAGCGGCCCTGGGCTGCCTGGTCAAGGACTACTTCCCCGAACCGGTGACGGTG

TCGTGGAACTCAGGCGCCCTGACCAGCGGCGTGCACACCTTCCCGGCTGTCCTACAGTCCT

CAGGACTCTACTCCCTCAGCAGCGTGGTGACCGTGCCCTCCAGCAGCTTGGGCACCCAGAC

CTACATCTGCAACGTGAATCACAAGCCCAGCAACACCAAGGTGGACAAGAGAGTTGAGCCC

AAATCTTGTGACAAAACTCACACATGCCCACCGTGCCCAGCACCTGAACTCCTGGGGGGAC

CGTCAGTCTTCCTCTTCCCCCCAAAACCCAAGGACACCCTCATGATCTCCCGGACCCCTGA

GGTCACATGCGTGGTGGTGGACGTGAGCCACGAAGACCCTGAGGTCAAGTTCAACTGGTAC

GTGGACGGCGTGGAGGTGCATAATGCCAAGACAAAGCCGCGGGAGGAGCAGTACAACAGCA

CGTACCGTGTGGTCAGCGTCCTCACCGTCCTGCACCAGGACTGGCTGAATGGCAAGGAGTA

CAAGTGCAAGGTCTCCAACAAAGCCCTCCCAGCCCCCATCGAGAAAACCATCTCCAAAGCC

AAAGGGCAGCCCCGAGAACCACAGGTGTACACCCTGCCCCCATCCCGGGAGGAGATGACCA

AGAACCAGGTCAGCCTGACCTGCCTGGTCAAAGGCTTCTATCCCAGCGACATCGCCGTGGA

GTGGGAGAGCAATGGGCAGCCGGAGAACAACTACAAGACCACGCCTCCCGTGCTGGACTCC

GACGGCTCCTTCTTCCTCTATAGCAAGCTCACCGTGGACAAGAGCAGGTGGCAGCAGGGGA

ACGTCTTCTCATGCTCCGTGATGCATGAGGCTCTGCACAACCACTACACGCAGAAGAGCCT

CTCCCTGTCTCCGGGTAAA

4P12 gamma variable region:

(SEQ ID NO: 66)
CAGGTGCAGCTGGTGGAGTCGGGGGGAGGCGTGATCCAGCCTGGGAGGTCCCTGAGACTCT

CCTGTGTTGCCTCTAAATTCATCTTCAGTAACCATGGCATACACTGGGTCCGCCAGGCTCC

AGGCAAGGGGCTGGAGTGGGTGGCGGTTATATCAAAAGATGGGACTAATGCACACTACGCA

GACTCCGTGAGGGGCCGATTTAGCATCTCCAGAGACAACTCCAAGGACACTGTCTTTCTGG

AAATGCGCAGCCTGCGACCTGAAGACACGGCTGTGTATTACTGTGCGAGAGAGGGCCGGTG

TATTGAAGAAAACTGCTACTCCGGACAGATTGACTATTGGGGCCAGGGATCCCTGGTCACC

GTCTCG

4P12gamma:

(SEQ ID NO: 14)
MELGLSWVFLVALLRGVQCQVQLVESGGGVIQPGRSLRLSCVASKFIFSNHGIHWVRQAPG

KGLEWVAVISKDGTNAHYADSVRGRFSISRDNSKDTVFLEMRSLRPEDTAVYYCAREGRCI

EENCYSGQIDYWGQGSLVIVSSASTKGPSVFPLAPSSKSTSGGTAALGCLVKDYFPEPVTV

SWNSGALTSGVHTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIEKTISKA

KGQPREPQVYTLPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGK

4P12 gamma variable region (Kabat CDRs underlined,
Chothia CDRs in bold italics):
(SEQ ID NO: 67)
QVQLVESGGGVIQPGRSLRLSCVAS*KFIFSN*HGIHWVRQAPGKGLEWVA*VISKDGTNAH*YA

DSVRGRFSISRDNSKDTVFLEMRSLRPEDTAVYYCAR*EGRCIEENCYSGQIDY*WGQGSLVT

VS

4P12 gamma heavy chain Kabat CDRs:
CDR 1:
(SEQ ID NO: 36)
SNHGIH

CDR 2:
(SEQ ID NO: 68)
VISKDGTNAHYADSVRG

CDR 3:
(SEQ ID NO: 69)
EGRCIEENCYSGQIDY

4P12 gamma heavy chain Chothia CDRs:
CDR 1:
(SEQ ID NO: 70)
KFIFSN

CDR 2:
(SEQ ID NO: 71)
VISKDGTNAH

CDR 3:
(SEQ ID NO: 69)
EGRCIEENCYSGQIDY

4P12 kappa:
(SEQ ID NO: 15)
ATGGAAGCCCCAGCGCAGCTTCTCTTCCTCCTGCTACTCTGGCTCCCAGATACCACCGGAG

AAATTCTATTGACACAGTCTCCAGCCACCCTGTCTTTGTCTCCAGGGGAAAGAGCCACCCT

CTCCTGCAGGGCCAGTCAGAGTGTTGGCAGGTACATGGCCTGGTATCAACAGAGACCTGGC

CAGGCTCCCAGGCTCCTCATCTATGATGCATCCATCAGGGCCACTGGCATCCCAGCCAGGT

TCAGTGGCAGTGGGTCTGGGACAGACTTCACTCTCACCATCAGCAGCCTACAGCCTGAAGA

TTTTGCAATTTATTACTGTCAGCAGCGTAGCAGCTGGCCCCCGCTCACTTTCGGCGGAGGG

ACCAAGGTGAGATCAAACGTACGGTGGCTGCACCATCTGTCTTCATCTTCCCGCCATCTG

ATGAGCAGTTGAAATCTGGAACTGCCTCTGTTGTGTGCCTGCTGAATAACTTCTATCCCAG

AGAGGCCAAAGTACAGTGGAAGGTGGATAACGCCCTCCAATCGGGTAACTCCCAGGAGAGT

GTCACAGAGCAGGACAGCAAGGACAGCACCTACAGCCTCAGCAGCACCCTGACGCTGAGCA

AAGCAGACTACGAGAAACACAAAGTCTACGCCTGCGAAGTCACCCATCAGGGCCTGAGCTC

GCCCGTCACAAAGAGCTTCAACAGGGGAGAGTGT

4P12 kappa variable region:
(SEQ ID NO: 72)
GAAATTCTATTGACACAGTCTCCAGCCACCCTGTCTTTGTCTCCAGGGGAAAGAGCCACCC

TCTCCTGCAGGGCCAGTCAGAGTGTTGGCAGGTACATGGCCTGGTATCAACAGAGACCTGG

CCAGGCTCCCAGGCTCCTCATCTATGATGCATCCATCAGGGCCACTGGCATCCCAGCCAGG

-continued

```
TTCAGTGGCAGTGGGTCTGGGACAGACTTCACTCTCACCATCAGCAGCCTACAGCCTGAAG

ATTTTGCAATTTATTACTGTCAGCAGCGTAGCAGCTGGCCCCCGCTCACTTTCGGCGGAGG

GACCAAGGTTGAGATCAAACGTACG
```

4P12 kappa:
(SEQ ID NO: 16)
MEAPAQLLFLLLLWLPDTTGEILLTQSPATLSLSPGERATLSCRASQSVGRYMAWYQQRPG

QAPRLLIYDASIRATGIPARFSGSGSGTDFTLTISSLQPEDFAIYYCQQRSSWPPLTFGGG

TKVEIKRTVAAPSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRGEC

4P12 kappa variable region (Kabat CDRs underlined,
Chothia CDRs in bold italics):
(SEQ ID NO: 73)
EILLTQSPATLSLSPGERATLSC*RASQSVGRYMA*WYQQRPGQAPRLLIY*DASIRAT*GIPAR
FSGSGSGTDFTLTISSLQPEDFAIYYC*QQRSSWPPLT*FGGGTKVEIKRT 4P12 kappa light chain Kabat CDRs:
CDR 1:
(SEQ ID NO: 74)
RASQSVGRYMA

CDR 2:
(SEQ ID NO: 75)
DASIRAT

CDR 3:
(SEQ ID NO: 76)
QQRSSWPPLT

4P12 kappa light chain Chothia CDRs:
CDR 1:
(SEQ ID NO: 74)
RASQSVGRYMA

CDR 2:
(SEQ ID NO: 75)
DASIRAT

CDR 3:
(SEQ ID NO: 76)
QQRSSWPPLT

5P9 gamma:
(SEQ ID NO: 17)
ATGGAGTTGGGGCTGCGCTGGGTTTTCCTCGTTGCTCTTTTAAGAGGTGTCCAGTGTCAGG

```
TGCAGCTGGTGGAGTCGGGGGGAGGCGTGATCCAGCCTGGGAGGTCCCTGAGACTCTCCTG

TGTTGCCTCTAAATTCATCTTCAGTAACCATGGCATACACTGGGTCCGCCAGGCTCCAGGC

AAGGGGCTGGAGTGGGTGGCGGTTATATCAAAGGATGGGACTAATGCACACTACGCAGACT

CCGTGAGGGGCCGATTTAGCATCTCCAGAGACAACTCCAAGGACACTGTCTTTCTGGAAAT

GCGCAGCCTGCGACCTGAAGACACGGCTGTCTATTACTGTGCGAGAGAGGGCCGGTGTATT

GAAGAAAAGTGCTACTCCGGACAGATTGACTATTGGGGCAGGGATCCCTGGTCACCGTCT
```

CGAGCGCCTCCACCAAGGGCCCATCGGTCTTCCCCCTGGCACCCTCCTCCAAGAGCACCTC

TGGGGGCACAGCGGCCCTGGGCTGCCTGGTCAAGGACTACTTCCCCGAACCGGTGACGGTG

TCGTGGAACTCAGGCGCCCTGACCAGCGGCGTGCACACCTTCCCGGCTGTCCTACAGTCCT

CAGGACTCTACTCCCTCAGCAGCGTGGTGACCGTGCCCTCCAGCAGCTTGGGCACCCAGAC

CTACATCTGCAACGTGAATCACAAGCCCAGCAACACCAAGGTGGACAAGAGAGTTGAGCCC

AAATCTTGTGACAAAACTCACACATGCCCACCGTGCCCAGCACCTGAACTCCTGGGGGGAC

CGTCAGTCTTCCTCTTCCCCCCAAAACCCAAGGACACCCTCATGATCTCCCGGACCCCTGA

GGTCACATGCGTGGTGGTGGACGTGAGCCACGAAGACCCTGAGGTCAAGTTCAACTGGTAC

GTGGACGGCGTGGAGGTGCATAATGCCAAGACAAAGCCGCGGGAGGAGCAGTACAACAGCA

```
CGTACCGTGTGGTCAGCGTCCTCACCGTCCTGCACCAGGACTGGCTGAATGGCAAGGAGTA

CAAGTGCAAGGTCTCCAACAAAGCCCTCCCAGCCCCCATCGAGAAAACCATCTCCAAAGCC

AAAGGGCAGCCCCGAGAACCACAGGTGTACACCCTGCCCCCATCCCGGGAGGAGATGACCA

AGAACCAGGTCAGCCTGACCTGCCTGGTCAAAGGCTTCTATCCCAGCGACATCGCCGTGGA

GTGGGAGAGCAATGGGCAGCCGGAGAACAACTACAAGACCACGCCTCCCGTGCTGGACTCC

GACGGCTCCTTCTTCCTCTATAGCAAGCTCACCGTGGACAAGAGCAGGTGGCAGCAGGGGA

ACGTCTTCTCATGCTCCGTGATGCATGAGGCTCTGCACAACCACTACACGCAGAAGAGCCT

CTCCCTGTCTCCGGGTAAA
```

5P9 gamma variable region:
(SEQ ID NO: 77)
```
CAGGTGCAGCTGGTGGAGTCGGGGGGAGGCGTGATCCAGCCTGGGAGGTCCCTGAGACTCT

CCTGTGTTGCCTCTAAATTCATCTTCAGTAACCATGGCATACACTGGGTCCGCCAGGCTCC

AGGCAAGGGGCTGGAGTGGGTGGCGGTTATATCAAAGGATGGGACTAATGCACACTACGCA

GACTCCGTGAGGGGCCGATTTAGCATCTCCAGAGACAACTCCAAGGACACTGTCTTTCTGG

AAATGCGCAGCCTGCGACCTGAAGACACGGCTGTCTATTACTGTGCGAGAGAGGGCCGGTG

TATTGAAGAAAAGTGCTACTCCGGACAGATTGACTATTGGGGCAGGGATCCCTGGTCACC

GTCTCG
```

5P9 gamma:
(SEQ ID NO: 18)
MELGLRWVFLVALLRGVQCQVQLVESGGGVIQPGRSLRLSCVASKFIFSNHGIHWVRQAPG
KGLEWVAVISKDGTNAHYADSVRGRFSISRDNSKDTVFLEMRSLRPEDTAVYYCAREGRCI
EEKCYSGQIDYWGQGSLVTVS**SASTKGPSVFPLAPSSKSTSGGTAALGCLVKDYFPEPVTV
SWNSGALTSGVHTFPAVLQSSGLYSLSSVVTVPSSSLGTQTYICNVNHKPSNTKVDKRVEP
KSCDKTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTISKA
KGQPREPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK**

5P9 gamma variable region (Kabat CDRs underlined,
Chothia CDRs in bold italics):
(SEQ ID NO: 78)
QVQLVESGGGVIQPGRSLRLSCVAS*KFIFSN*<u>HGIH</u>WVRQAPGKGLEWVA*VISKDGTNAH*<u>YA
DSVRGR</u>FSISRDNSKDTVFLEMRSLRPEDTAVYYCAR<u>*EGRCIEEKCYSGQIDY*</u>WGQGSLVT
VS 5P9 gamma heavy chain Kabat CDRs:
CDR 1:
(SEQ ID NO: 36)
SNHGIH

CDR 2:
(SEQ ID NO: 79)
VISKDGTNAHYADSVRGR

CDR 3:
(SEQ ID NO: 80)
EGRCIEEKCYSGQIDY

5P9 gamma heavy chain Chothia CDRs:
CDR 1:
(SEQ ID NO: 70)
KFIFSN

CDR 2:
(SEQ ID NO: 71)
VISKDGTNAH

-continued

CDR 3:
(SEQ ID NO: 80)
EGRCIEEKCYSGQIDY

5P9 kappa:
(SEQ ID NO: 19)
ATGGAAGCCCCAGCGCAGCTTCTCTTCCTCCTGCTACTCTGGCTCCCAGATACCACCGGAG
AAATTCTATTGACACAGTCTCCAGCCACCCTGTCTTTGTCTCCAGGGGAAAGAGCCACCCT
CTCCTGCAGGGCCAGTCAGAGTGTTGGCAGGTACATGGCCTGGTATCAACAGAGACCTGGC
CAGGCTCCCAGGCTCCTCATCTATGATGCATCCATCAGGGCCACTGGCATCCCAGCCAGGT
TCAGTGGCAGTGGGTCTGGGACAGACTTCACTCTCACCATCAGCAGCCTACAGACTGAAGA
TTTTGCAATTTATTACTGTCAGCAGCGTAGCAGCTGGCCCCCGCTCACTTTCGGCGGAGGG
ACCAAGGTTGAGATCAAACGTACGGTGGCTGCACCATCTGTCTTCATCTTCCCGCCATCTG
ATGAGCAGTTGAAATCTGGAACTGCCTCTGTTGTGTGCCTGCTGAATAACTTCTATCCCAG
AGAGGCCAAAGTACAGTGGAAGGTGGATAACGCCCTCCAATCGGGTAACTCCCAGGAGAGT
GTCACAGAGCAGGACAGCAAGGACAGCACCTACAGCCTCAGCAGCACCCTGACGCTGAGCA
AAGCAGACTACGAGAAACACAAAGTCTACGCCTGCGAAGTCACCCATCAGGGCCTGAGCTC
GCCCGTCACAAAGAGCTTCAACAGGGGAGAGTGT

5P9 kappa variable region:
(SEQ ID NO: 81)
GAAATTCTATTGACACAGTCTCCAGCCACCCTGTCTTTGTCTCCAGGGGAAAGAGCCACCC
TCTCCTGCAGGGCCAGTCAGAGTGTTGGCAGGTACATGGCCTGGTATCAACAGAGACCTGG
CCAGGCTCCCAGGCTCCTCATCTATGATGCATCCATCAGGGCCACTGGCATCCCAGCCAGG
TTCAGTGGCAGTGGGTCTGGGACAGACTTCACTCTCACCATCAGCAGCCTACAGACTGAAG
ATTTTGCAATTTATTACTGTCAGCAGCGTAGCAGCTGGCCCCCGCTCACTTTCGGCGGAGG
GACCAAGGTTGAGATCAAACGTACG 5P9 kappa
(SEQ ID NO: 20)
MEAPAQLLFLLLLWLPDTTGEILLTQSPATLSLSPGERATLSCRASQSVGRYMAWYQQRPG
QAPRLLIYDASIRATGIPARFSGSGSGTDFTLTISSLQTEDFAIYYCQQRSSWPPLTFGGG
TKVEIKRTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC

5P9 kappa variable region (Kabat CDRs underlined,
Chothia CDRs in bold italics):
(SEQ ID NO: 82)
EILLTQSPATLSLSPGERATLSC*RASQSVGRYMA*WYQQRPGQAPRLLIY*DASIRAT*GIPAR
FSGSGSGTDFTLTISSLQTEDFAIYYC*QQRSSWPPLT*FGGGTKVEIKRT 5P9 kappa light chain Kabat CDRs:
CDR 1:
(SEQ ID NO: 74)
RASQSVGRYMA

CDR 2:
(SEQ ID NO: 75)
DASIRAT

CDR 3:
(SEQ ID NO: 76)
QQRSSWPPLT

5P9 kappa light chain Chothia CDRs:
CDR 1:
(SEQ ID NO: 74)
RASQSVGRYMA

```
CDR 2:
                                                           (SEQ ID NO: 75)
DASIRAT

CDR 3:
                                                           (SEQ ID NO: 76)
QQRSSWPPLT

9C16 gamma:
                                                           (SEQ ID NO: 21)
ATGGAGTTGGGGCTGTGCTGGGTTTTCCTCGTTGCTCTTTTAAGAGGTGTCCAGTGTCAGG

TGCAGCTGGTGGACTCTGGGGGAGGCGTGGTCCAGCCTGGGAGGTCCCTGAGACTCTCCTG

TGCAGCCTCTGGACTCACCTTCAGTGATTATGGTATGCACTGGGTCCGCCAGGCTCCAGGC

AAGGGGCTGGAGTGGGTGGCAGTCATCTCAAAGGATGGAACTAACACACACTATGCAGACT

CCGTGAGGGGCCGATTCACCATCTCCAGAGACAACTCCAAGAACATTTTCTATCTGCAAAT

GAACGGCCTGAGAGCTGAGGACACGGCTGTCTATTACAGTGGGAGAGATGGGAAGTGTCCT

GATCTTAAGTGCTACTCAGGGTTGATTGACTACTGGGGCCAGGGGACCCTGGTCACCGTCT

CGAGCGCCTCCACCAAGGGCCCATCGGTCTTCCCCCTGGCACCCTCCTCCAAGAGCACCTC

TGGGGGCACAGCGGCCCTGGGCTGCCTGGTCAAGGACTACTTCCCCGAACCGGTGACGGTG

TCGTGGAACTCAGGCGCCCTGACCAGCGGCGTGCACACCTTCCCGGCTGTCCTACAGTCCT

CAGGACTCTACTCCCTCAGCAGCGTGGTGACCGTGCCCTCCAGCAGCTTGGGCACCCAGAC

CTACATCTGCAACGTGAATCACAAGCCCAGCAACACCAAGGTGGACAAGAGAGTTGAGCCC

AAATCTTGTGACAAAACTCACACATGCCCACCGTGCCCAGCACCTGAACTCCTGGGGGGAC

CGTCAGTCTTCCTCTTCCCCCCAAAACCCAAGGACACCCTCATGATCTCCCGGACCCCTGA

GGTCACATGCGTGGTGGTGGACGTGAGCCACGAAGACCCTGAGGTCAAGTTCAACTGGTAC

GTGGACGGCGTGGAGGTGCATAATGCCAAGACAAAGCCGCGGGAGGAGCAGTACAACAGCA

CGTACCGTGTGGTCAGCGTCCTCACCGTCCTGCACCAGGACTGGCTGAATGGCAAGGAGTA

CAAGTGCAAGGTCTCCAACAAAGCCCTCCCAGCCCCCATCGAGAAAACCATCTCCAAAGCC

AAAGGGCAGCCCCGAGAACCACAGGTGTACACCCTGCCCCCATCCCGGGAGGAGATGACCA

AGAACCAGGTCAGCCTGACCTGCCTGGTCAAAGGCTTCTATCCCAGCGACATCGCCGTGGA

GTGGGAGAGCAATGGGCAGCCGGAGAACAACTACAAGACCACGCCTCCCGTGCTGGACTCC

GACGGCTCCTTCTTCCTCTATAGCAAGCTCACCGTGGACAAGAGCAGGTGGCAGCAGGGGA

ACGTCTTCTCATGCTCCGTGATGCATGAGGCTCTGCACAACCACTACACGCAGAAGAGCCT

CTCCCTGTCTCCGGGTAAA

9C16 gamma variable region:
                                                           (SEQ ID NO: 83)
CAGGTGCAGCTGGTGGACTCTGGGGGAGGCGTGGTCCAGCCTGGGAGGTCCCTGAGACTCT

CCTGTGCAGCCTCTGGACTCACCTTCAGTGATTATGGTATGCACTGGGTCCGCCAGGCTCC

AGGCAAGGGGCTGGAGTGGGTGGCAGTCATCTCAAAGGATGGAACTAACACACACTATGCA

GACTCCGTGAGGGGCCGATTCACCATCTCCAGAGACAACTCCAAGAACATTTTCTATCTGC

AAATGAACGGCCTGAGAGCTGAGGACACGGCTGTCTATTACAGTGGGAGAGATGGGAAGTG

TCCTGATCTTAAGTGCTACTCAGGGTTGATTGACTACTGGGGCCAGGGGACCCTGGTCACC

GTCTCG

9C16 gamma:
                                                           (SEQ ID NO: 22)
MELGLCWVFLVALLRGVQCQVQLVDSGGGVVQPGRSLRLSCAASGLTFSDYGMHWVRQAPG

KGLEWVAVISKDGTNTHYADSVRGRFTISRDNSKNIFYLQMNGLRAEDTAVYYSGRDGKCP
```

DLKCYSGLIDYWGQGTLVIVSSASTKGPSVFPLAPSSKSTSGGTAALGCLVKDYFPEPVTV

SWNSGALTSGVHTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIEKTISKA

KGQPREPQVYTLPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGK

9C16 gamma variable region (Kabat CDRs underlined,
Chothia CDRs in bold italics):
(SEQ ID NO: 84)
QVQLVDSGGGVVQPGRSLRLSCAAS*GLTFSD*<u>YGMH</u>WVRQAPGKGLEWVA*VISKDGTNTH*<u>YA</u>

<u>DSVRG</u>RFTISRDNSKNIFYLQMNGLRAEDTAVYYSGR*DGKCPDLKCYSGLIDY*WGQGTLVT

VS

9C16 gamma heavy chain Kabat CDRs:
CDR 1:
(SEQ ID NO: 85)
SDYGMH

CDR 2:
(SEQ ID NO: 86)
VISKDGTNTHYADSVRG

CDR 3:
(SEQ ID NO: 87)
DGKCPDLKCYSGLIDY

9C16 gamma heavy chain Chothia CDRs:
CDR 1:
(SEQ ID NO: 88)
GLTFSD

CDR 2:
(SEQ ID NO: 89)
VISKDGTNTH

CDR 3:
(SEQ ID NO: 87)
DGKCPDLKCYSGLIDY

9C16 kappa:
(SEQ ID NO: 23)
ATGGAAGCCCCAGCGCAGCTTCTCTTCCTCCTGCTACTCTGGCTCCCAGATACCACCGGAG

AAATTGTGTTGACACAGTCTCCGGCCACCCTGTCTTTGTCTCCAGGGGAAAGAGCCACCCT

CTCCTGCAGGGCCAGTCAGAGTGTTGGCGGCTACTTAGCCTGGTACCAACAGAAGCCTGGC

CAGGGCTCCCAGGCTCCTCATCTATGATGCATCCAAAAGGGCCACTGGCATCCCAGCCAGGT

TCAGTGGCAGTGGGTCTGGGACAGACTTCACTCTCACCATCAGCACCCTAGAGCCTGAAGA

TTTTGCAATTTATTACTGTCACCAGCGTAGCAGCTGGCCTCCGCTCACTTTCGGCGGAGGG

ACCAAGGTGGATATCAAACGTACGGTGGCTGCACCATCTGTCTTCATCTTCCCGCCATCTG

ATGAGCAGTTGAAATCTGGAACTGCCTCTGTTGTGTGCCTGCTGAATAACTTCTATCCCAG

AGAGGCCAAAGTACAGTGGAAGGTGGATAACGCCCTCCAATCGGGTAACTCCCAGGAGAGT

GTCACAGAGCAGGACAGCAAGGACAGCACCTACAGCCTCAGCAGCACCCTGACGCTGAGCA

AAGCAGACTACGAGAAACACAAAGTCTACGCCTGCGAAGTCACCCATCAGGGCCTGAGCTC

GCCCGTCACAAAGAGCTTCAACAGGGGAGAGTGT

9C16 kappa variable region:
(SEQ ID NO: 90)
GAAATTGTGTTGACACAGTCTCCGGCCACCCTGTCTTTGTCTCCAGGGGAAAGAGCCACCC

TCTCCTGCAGGGCCAGTCAGAGTGTTGGCGGCTACTTAGCCTGGTACCAACAGAAGCCTGG

CCAGGCTCCCAGGCTCCTCATCTATGATGCATCCAAAAGGGCCACTGGCATCCCAGCCAGG

-continued

```
TTCAGTGGCAGTGGGTCTGGGACAGACTTCACTCTCACCATCAGCACCCTAGAGCCTGAAG

ATTTTGCAATTTATTACTGTCACCAGCGTAGCAGCTGGCCTCCGCTCACTTTCGGCGGAGG

GACCAAGGTGGATATCAAACGTACG
```

9C16 kappa:

(SEQ ID NO: 24)
MEAPAQLLFLLLLWLPDTTGEIVLTQSPATLSLSPGERATLSCRASQSVGGYLAWYQQKPG

QAPRLLIYDASKRATGIPARFSGSGSGTDFTLTISTLEPEDFAIYYCHQRSSWPPLTFGGG

TKVDIKRTVAAPSVFIFPPSDEQLKSGTASVVCLLNNFYPREAKVQWKVDNALQSGNSQES

VTEQDSKDSTYSLSSTLTLSKADYEKHKVYACEVTHQGLSSPVTKSFNRGEC

9C16 kappa variable region (Kabat CDRs underlined, Chothia CDRs in bold italics):

(SEQ ID NO: 91)
EIVLTQSPATLSLSPGERATLSC*RASQSVGGYLA*WYQQKPGQAPRLLIY*DASKRAT*GIPAR

FSGSGSGTDFTLTISTLEPEDFAIYYC*HQRSSWPPLT*FGGGTKVDIKRT

9C16 kappa light chain Kabat CDRs:
CDR 1:

(SEQ ID NO: 43)
RASQSVGGYLA

CDR 2:

(SEQ ID NO: 92)
DASKRAT

CDR 3:

(SEQ ID NO: 93)
HQRSSWPPLT

9C16 kappa light chain Chothia CDRs:
CDR 1:

(SEQ ID NO: 43)
RASQSVGGYLA

CDR 2:

(SEQ ID NO: 92)
DASKRAT

CDR 3:

(SEQ ID NO: 93)
HQRSSWPPLT

TABLE 2

CDR sequences from anti-CMV antibodies and consensus sequences (as determined using the Kabat and Chothia methods for the heavy chain, the CDRs of which are identical for the light chain).

| | CDRH1 (Kabat) | SEQ ID NO: | CDRH2 (Kabat) | SEQ ID NO: | CDRH3 (Kabat) | SEQ ID NO: |
|---|---|---|---|---|---|---|
| 2F10 | SNHGIH | 36 | VISSDGDDDRYADSVKG | 37 | DGRCGEPKCYSGLPDY | 38 |
| 2M16 | SNYGMH | 48 | VISSDGSNEHYADSVKG | 49 | DGRCPDVNCYSGLIDY | 50 |
| 2N9 | SSNGIH | 57 | VISSDANDKQYADSVKG | 58 | DGTCSGGNCYSGLIDY | 59 |
| 4P12 | SNHGIH | 36 | VISKDGTNAHYADSVRG | 68 | EGRCIEENCYSGQIDY | 69 |
| 5P9 | SNHGIH | 36 | VISKDGTNAHYADSVRGR | 79 | EGRCIEEKCYSGQIDY | 80 |
| 9C16 | SDYGMH | 85 | VISKDGTNTHYADSVRG | 86 | DGKCPDLKCYSGLIDY | 87 |
| Consensus A | SXXGXH | 95 | VISXDXXXXXYADSVRG | 96 | XCXCXXXCYSGXXDY | 97 |
| Consensus B | SXXGIH | 98 | VISXDGXNXHYADSVXG | 99 | DGXCSXXXCYSGLXDY | 100 |
| Consensus C | SXYGMH | 101 | | | EGRCIEEXCYSGQIDY | 102 |

TABLE 2-continued

CDR sequences from anti-CMV antibodies and consensus sequences (as
determined using the Kabat and Chothia methods for the heavy chain,
the CDRs of which are identical for the light chain).

| | | | | | | |
|---|---|---|---|---|---|---|
| Consensus D | | | | | DGXCPDXXCYSGLIDY | 103 |

| | CDRH1 (Chothia) | | CDRH2 (Chothia) | | CDRH3 (Chothia) | |
|---|---|---|---|---|---|---|
| 2F10 | GFTFSN | 39 | VISSDGDDDR | 40 | DGRCGEPKCYSGLPDY | 38 |
| 2M16 | GLTFSN | 118 | VISSDGSNEH | 51 | DGRCPDVNCYSGLIDY | 50 |
| 2N9 | GFTFSS | 60 | VISSDANDKQ | 61 | DGTCSGGNCYSGLIDY | 59 |
| 4P12 | KFIFSN | 70 | VISKDGTNAH | 71 | EGRCIEENCYSGQIDY | 69 |
| 5P9 | KFIFSN | 70 | VISKDGTNAH | 71 | EGRCIEEKCYSGQIDY | 80 |
| 9C16 | GLTFSD | 88 | VISKDGTNTH | 89 | DGKCPDLKCYSGLIDY | 87 |
| Consensus A | XXXFSX | 104 | VISXDXXXXX | 105 | XGXCXXXXCYSGXXDY | 106 |
| Consensus B | GXTFSX | 107 | VISKDGTNXH | 108 | DGXCXXXXCYSGLXDY | 109 |
| Consensus C | | | | | EGRCIEEXCYSGQIDY | 110 |

| | CDRL1 | | CDRL2 | | CDRL3 | |
|---|---|---|---|---|---|---|
| 2F10 | RASQSVGGYLA | 43 | DASNRAT | 44 | LQRNTWPPLT | 45 |
| 2M16 | RASQSVGRYLA | 53 | DASNRAT | 44 | QQRSNWPPLT | 54 |
| 2N9 | RASQSVGGYLA | 43 | ASIRAT | 64 | HQRSNWPPLT | 65 |
| 4P12 | RASQSVGRYMA | 74 | DASIRAT | 75 | QQRSSWPPLT | 76 |
| 5P9 | RASQSVGRYMA | 74 | DASIRAT | 75 | QQRSSWPPLT | 76 |
| 9C16 | RASQSVGGYLA | 43 | DASKRAT | 92 | HQRSSWPPLT | 93 |
| Consensus A | RASQSVGXYXA | 111 | XASXRAT | 112 | XQRXXWPPLT | 113 |
| Consensus B | RASQSVGXYLA | 114 | DASXRAT | 115 | HQRSXWPPLT | 116 |
| Consensus C | | | | | QQRSXWPPLT | 117 |

Example 2

Identification of Conserved Antibody Variable Regions

Figure 1B:
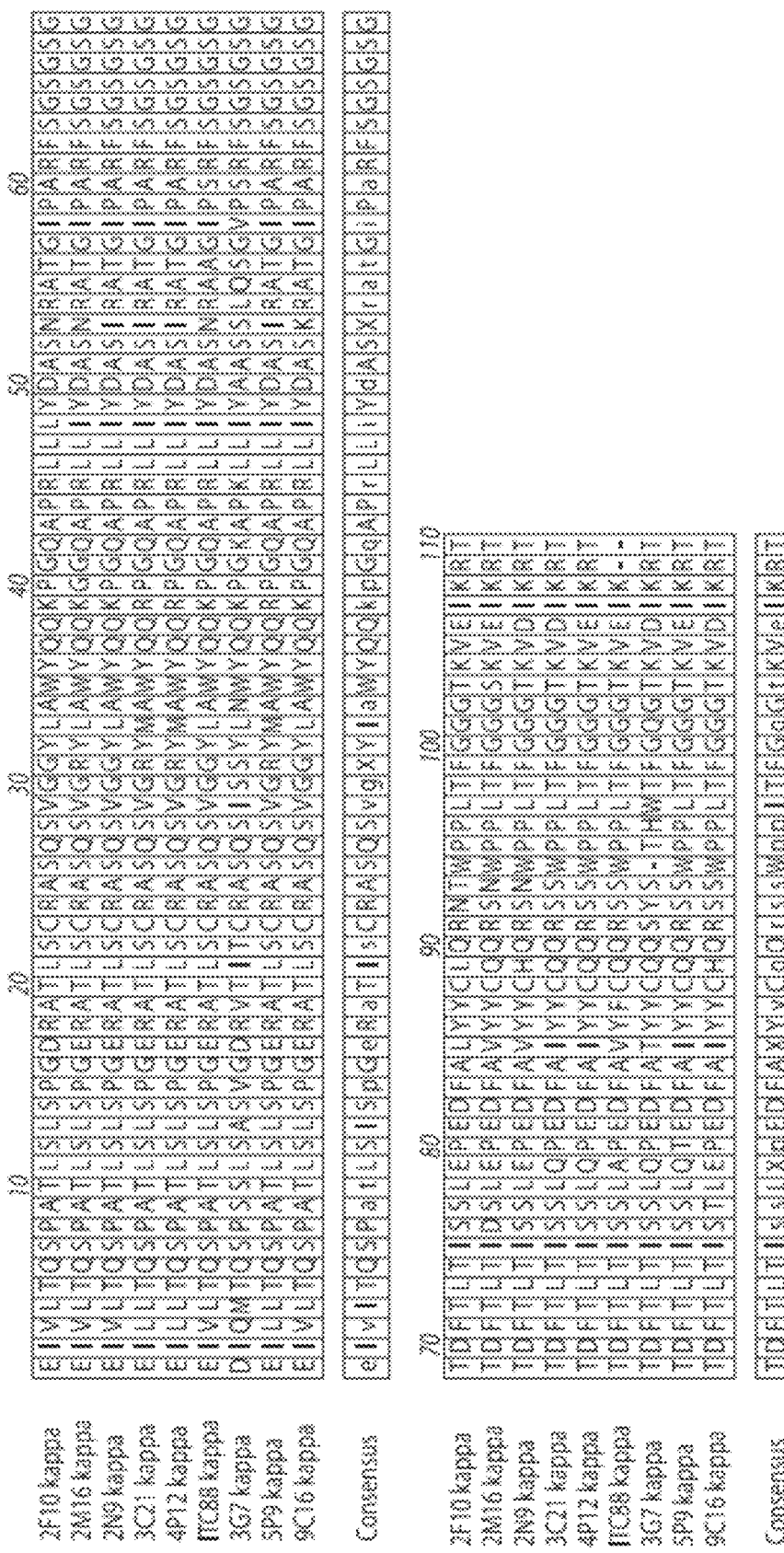
FIG. 1 shows an alignment of the amino acid sequences of the variable regions of the indicated human anti-CMV antibodies.
Figure 2:
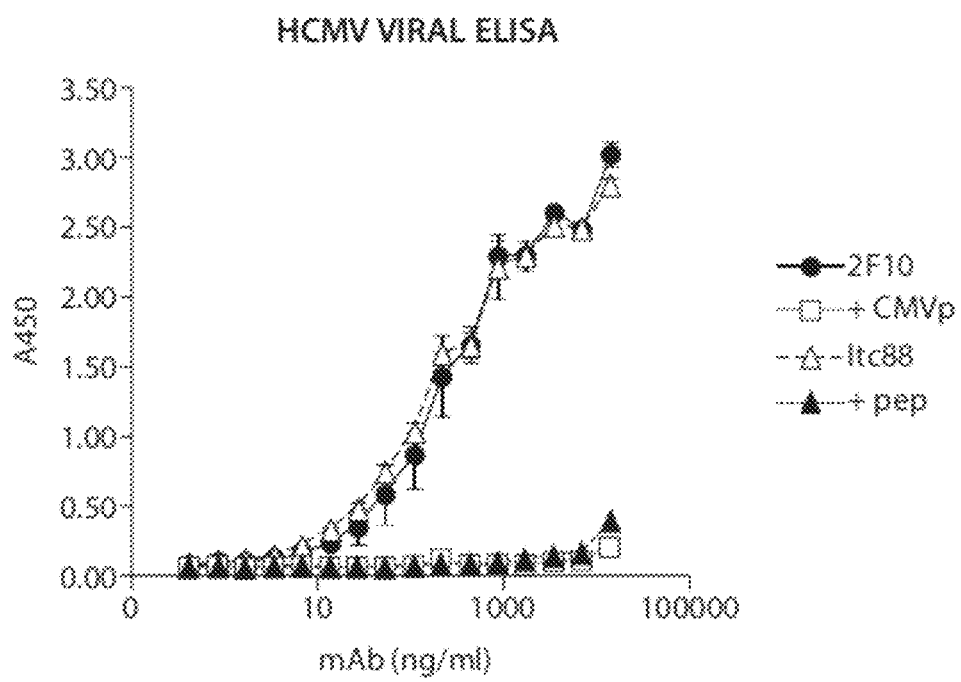
FIG. 2 is a graph depicting the binding of the 2F10 human anti-CMV antibody to the CMV gp116 epitope AD2 peptide, in the presence or absence of competing peptide, as indicated. The graph shows fluorescence associated with the indicated concentrations of antibody.
Figure 3:
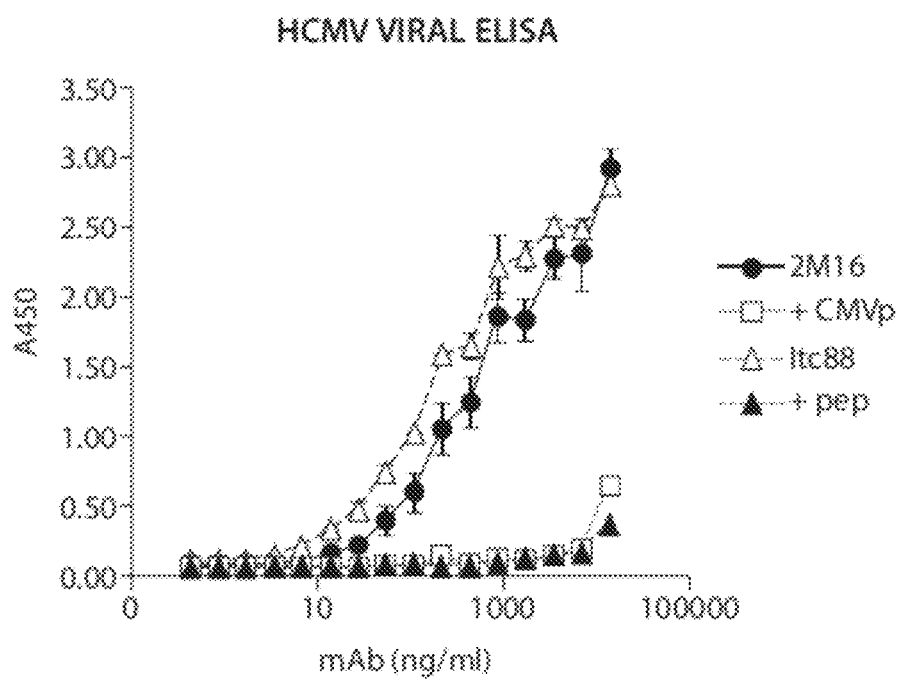
FIG. 3 is a graph depicting the binding of the 2M16 human anti-CMV antibody to the CMV gp116 epitope AD2 peptide, in the presence or absence of competing peptide, as indicated. The graph shows fluorescence associated with the indicated concentrations of antibody.
Figure 4:
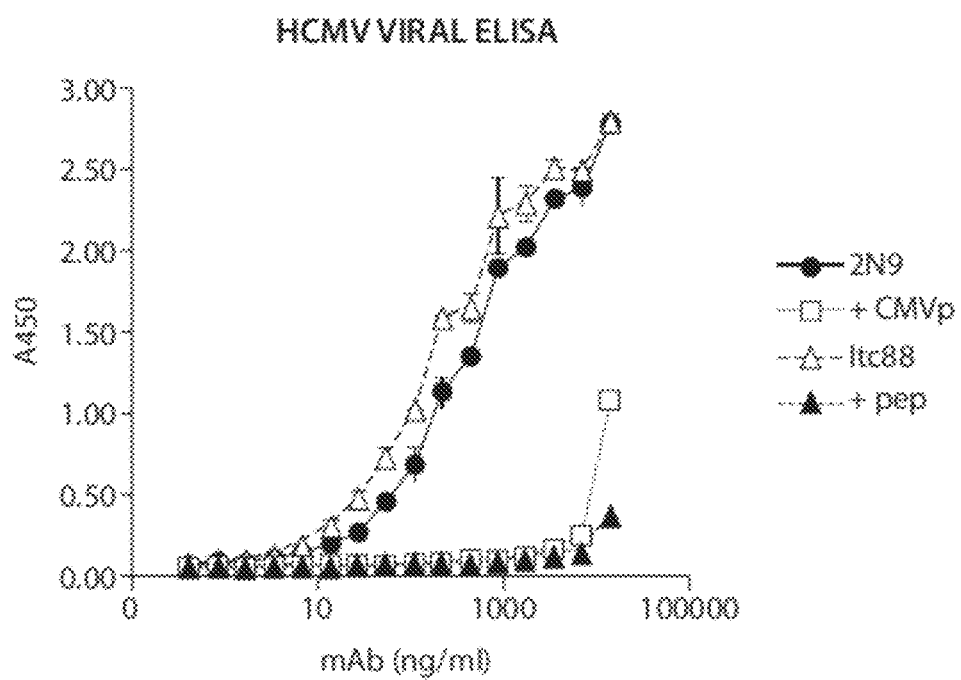
FIG. 4 is a graph depicting the binding of the 2N9 human anti-CMV antibody to the CMV gp116 epitope AD2 peptide, in the presence or absence of competing peptide, as indicated. The graph shows fluorescence associated with the indicated concentrations of antibody.
Figure 5:
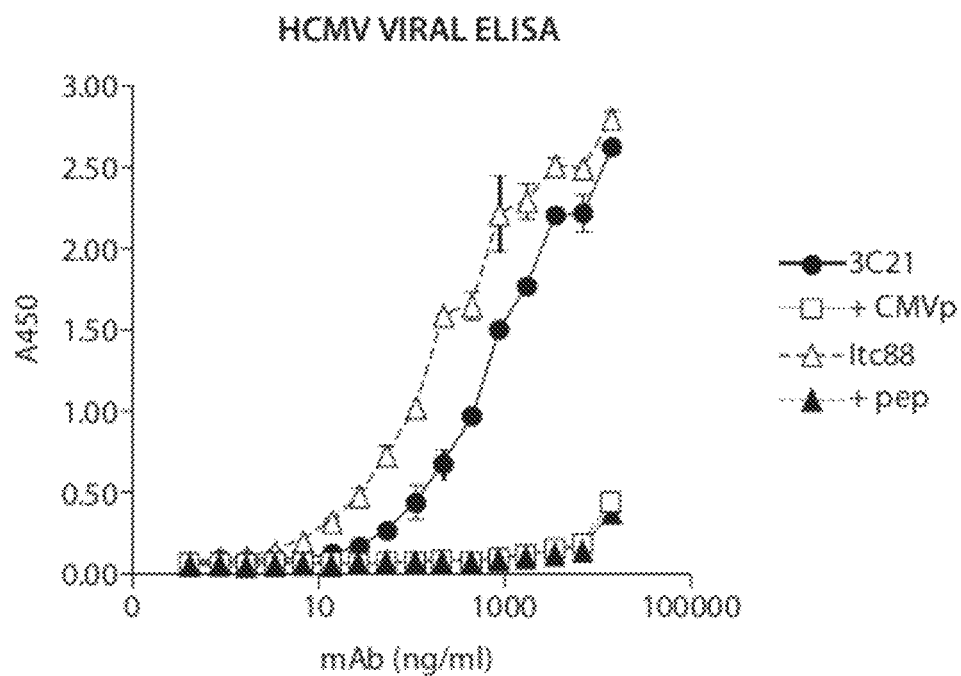
FIG. 5 is a graph depicting the binding of the 3C21 human anti-CMV antibody to the CMV gp116 epitope AD2 peptide, in the presence or absence of competing peptide, as indicated. The graph shows fluorescence associated with the indicated concentrations of antibody.
Figure 6:
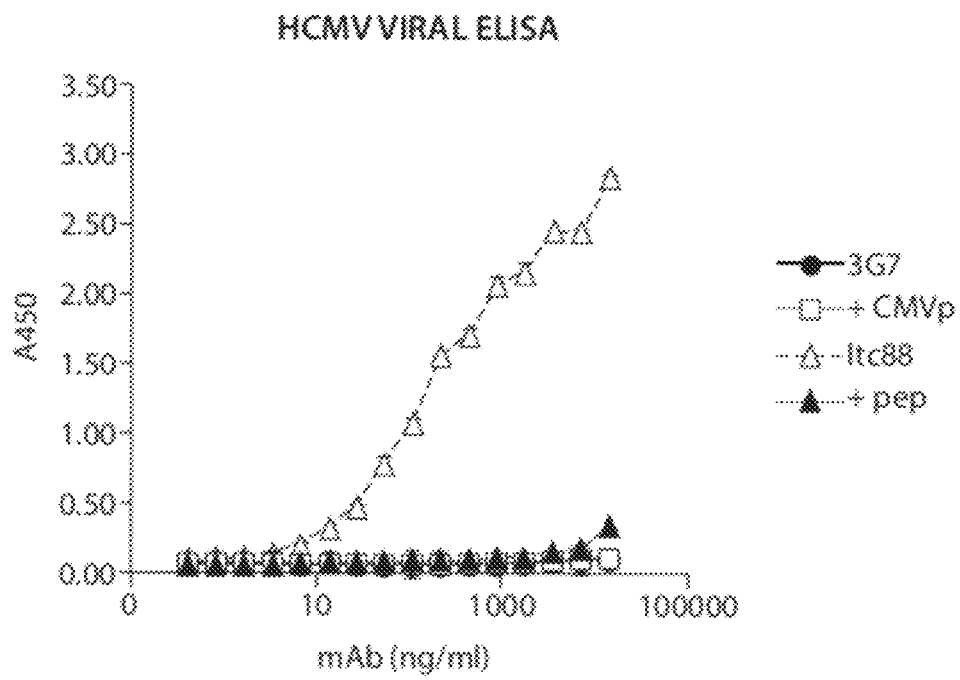
FIG. 6 is a graph depicting the binding of the 3G7 human anti-CMV antibody to the CMV gp116 epitope AD2 peptide, in the presence or absence of competing peptide, as indicated. The graph shows fluorescence associated with the indicated concentrations of antibody.
Figure 7:
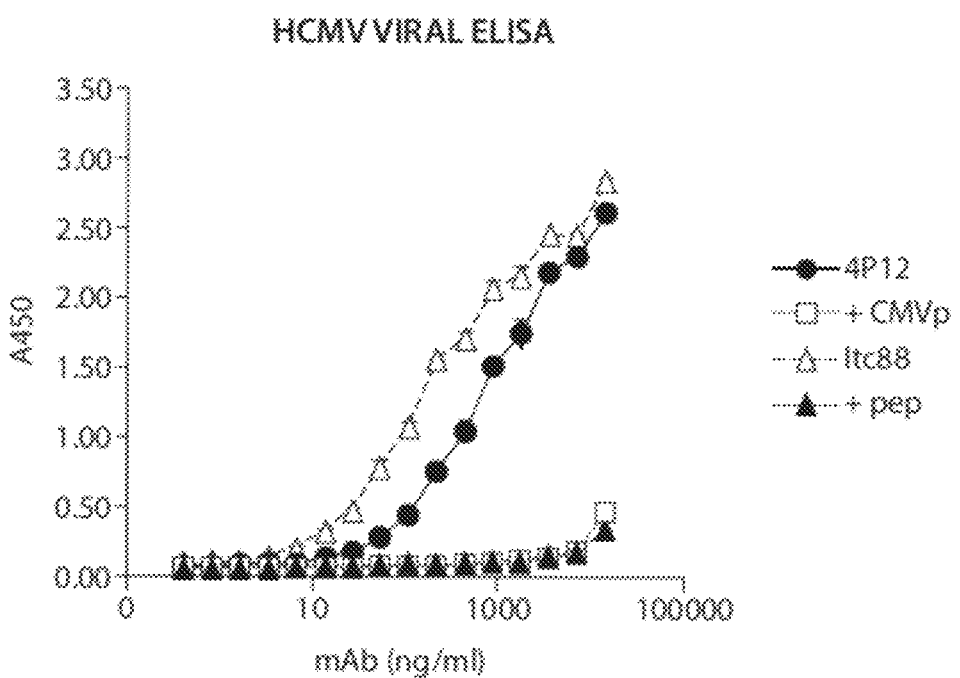
FIG. 7 is a graph depicting the binding of the 4P12 human anti-CMV antibody to the CMV gp116 epitope AD2 peptide, in the presence or absence of competing peptide, as indicated. The graph shows fluorescence associated with the indicated concentrations of antibody.
Figure 8:
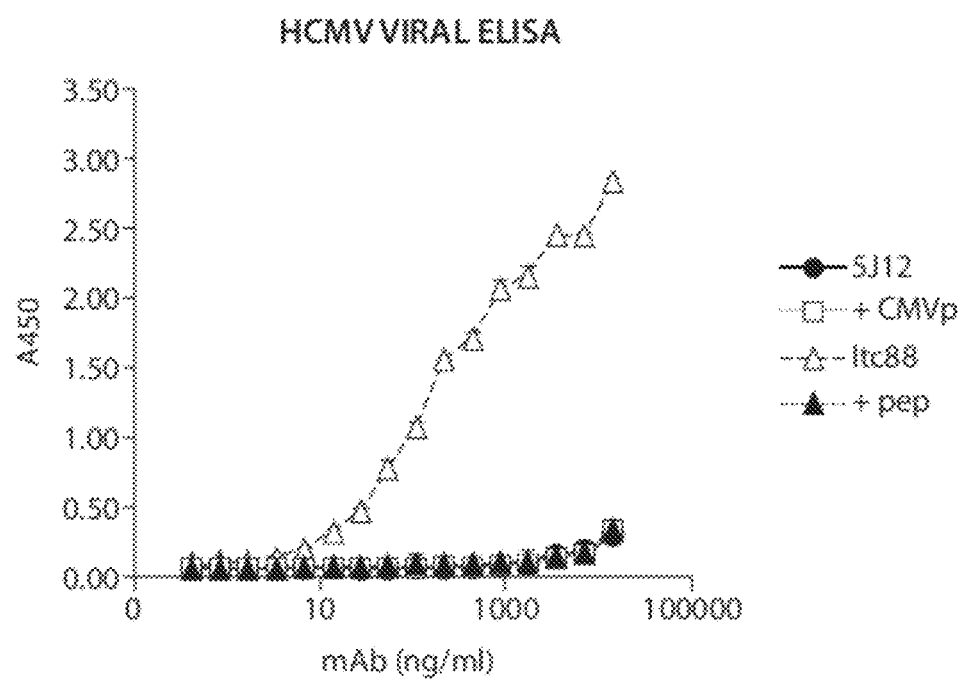
FIG. 8 is a graph depicting the binding of the 5J12 human anti-CMV antibody to the CMV gp116 epitope AD2 peptide, in the presence or absence of competing peptide, as indicated. The graph shows fluorescence associated with the indicated concentrations of antibody.
Figure 9:
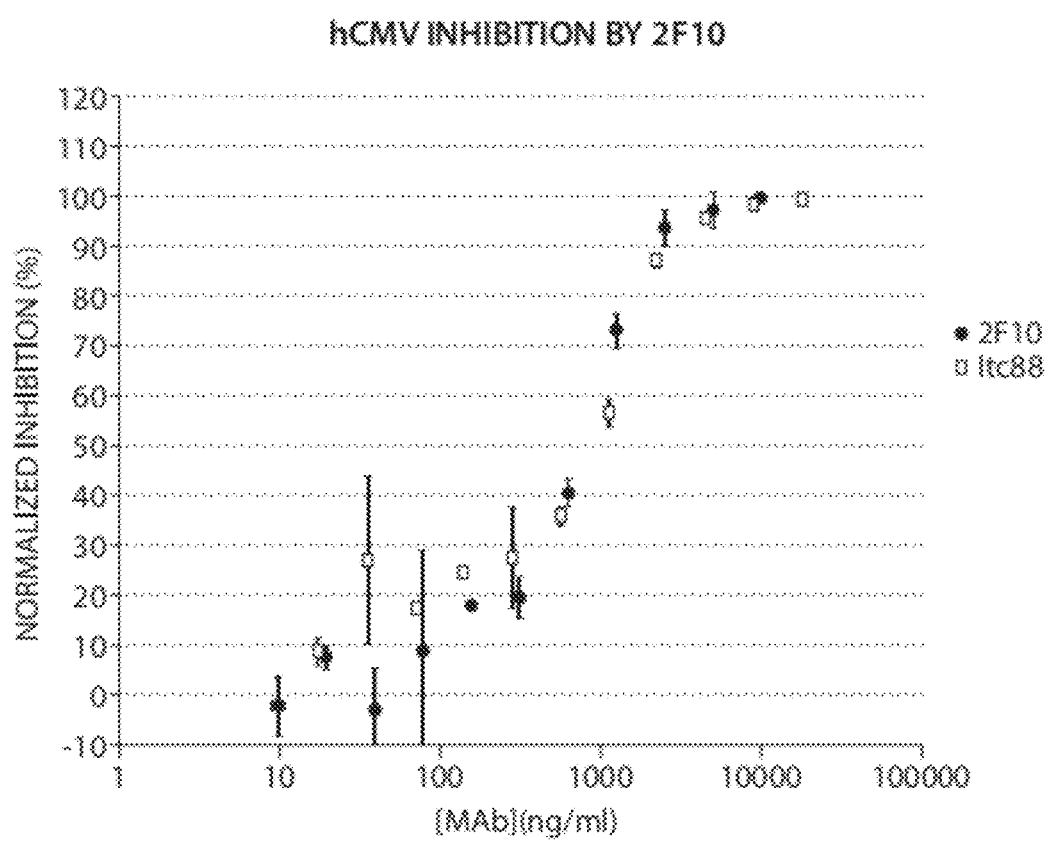
FIG. 9 is a graph depicting the neutralization of CMV virus by the 2F10 human anti-CMV antibody. The graphs show the amount of viral inhibition associated with the indicated concentrations of antibody.
Figure 10:
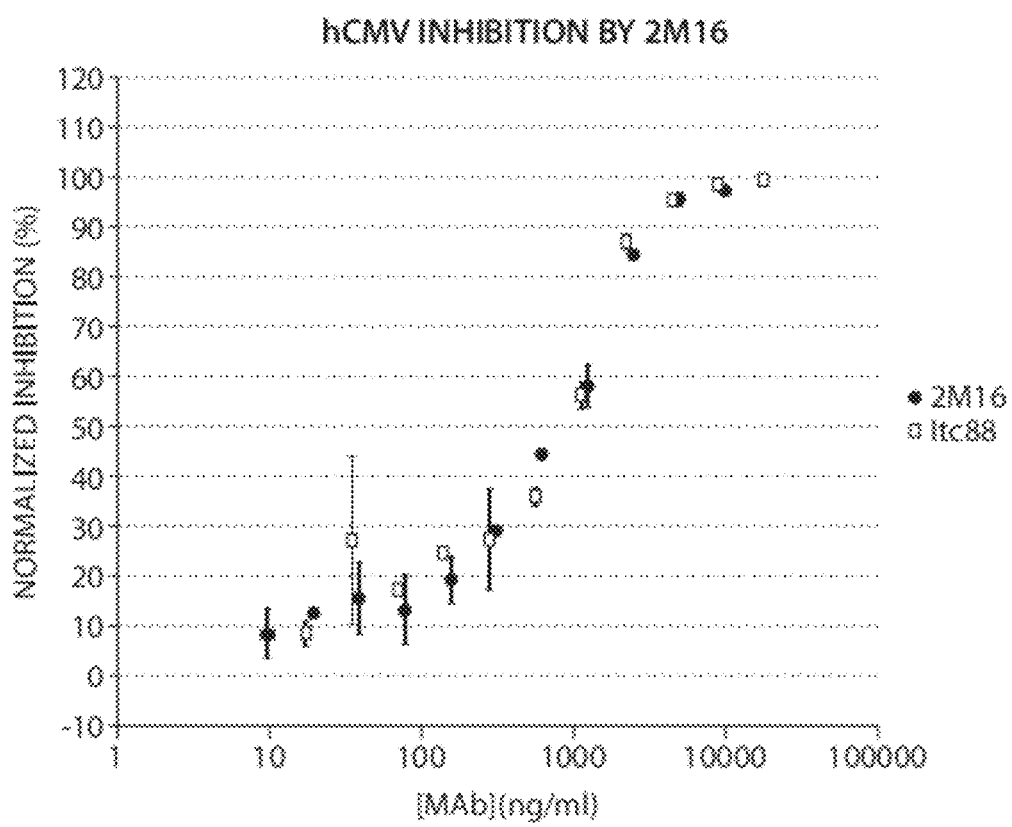
FIG. 10 is a graph depicting the neutralization of CMV virus by the 2M16 human anti-CMV antibody. The graphs show the amount of viral inhibition associated with the indicated concentrations of antibody.
Figure 11:
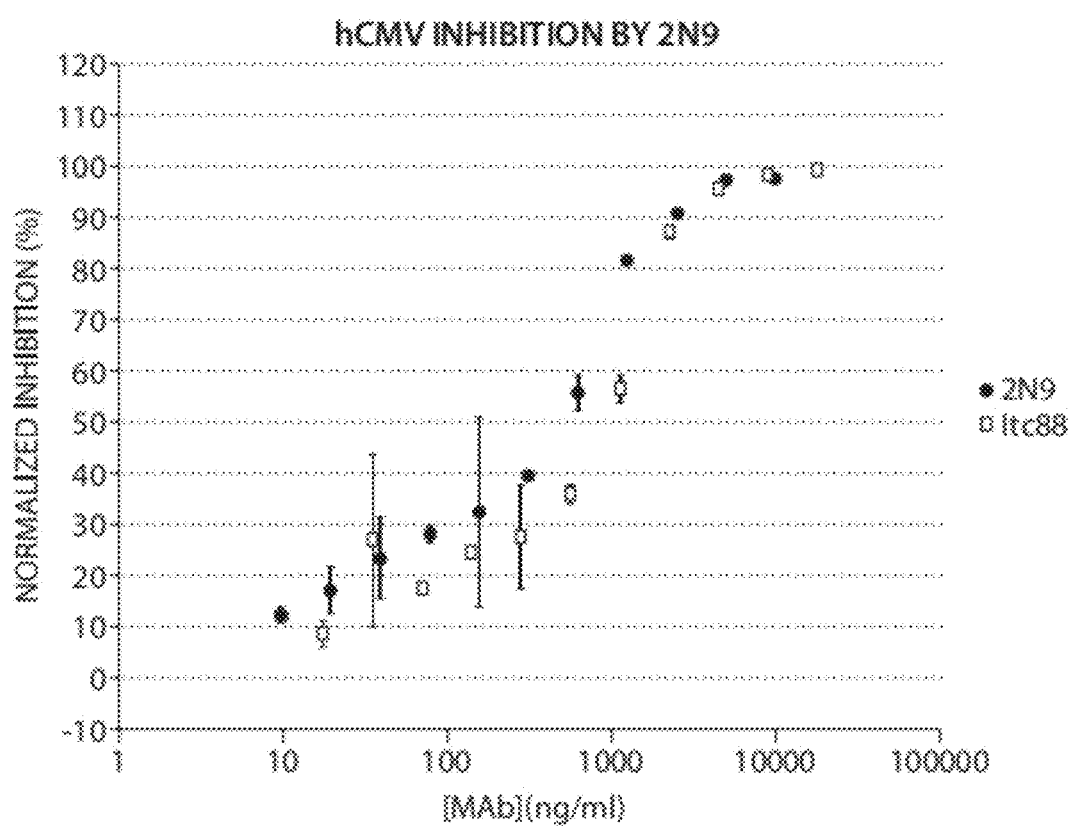
FIG. 11 is a graph depicting the neutralization of CMV virus by the 2N9 human anti-CMV antibody. The graphs show the amount of viral inhibition associated with the indicated concentrations of antibody.
Figure 12:
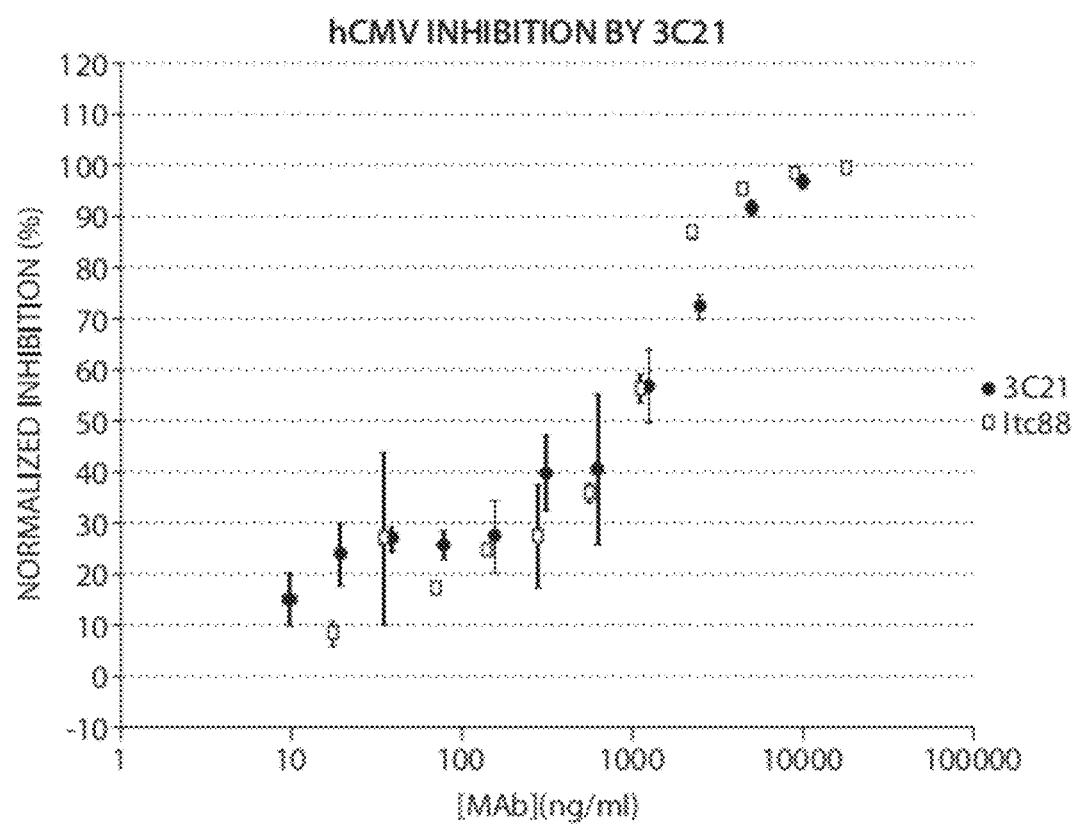
FIG. 12 is a graph depicting the neutralization of CMV virus by the 3C21 human anti-CMV antibody. The graphs show the amount of viral inhibition associated with the indicated concentrations of antibody.
Figure 13:
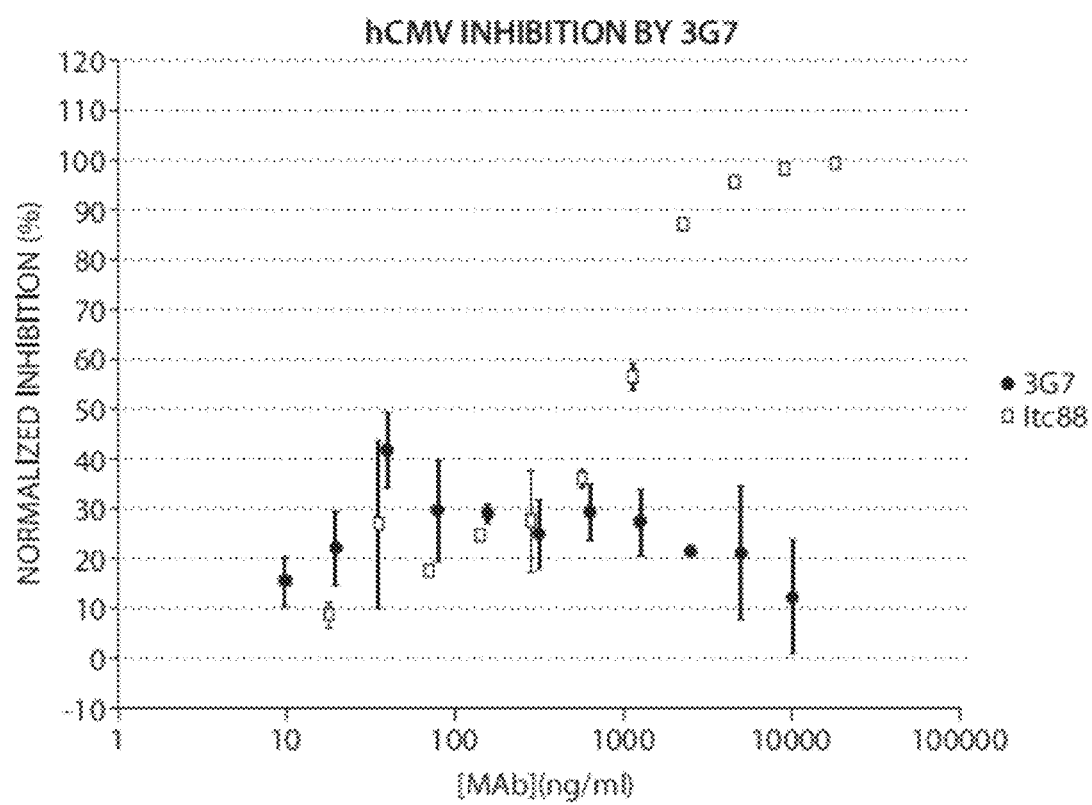
FIG. 13 is a graph depicting the neutralization of CMV virus by the 3G7 human anti-CMV antibody. The graphs show the amount of viral inhibition associated with the indicated concentrations of antibody.
Figure 14:
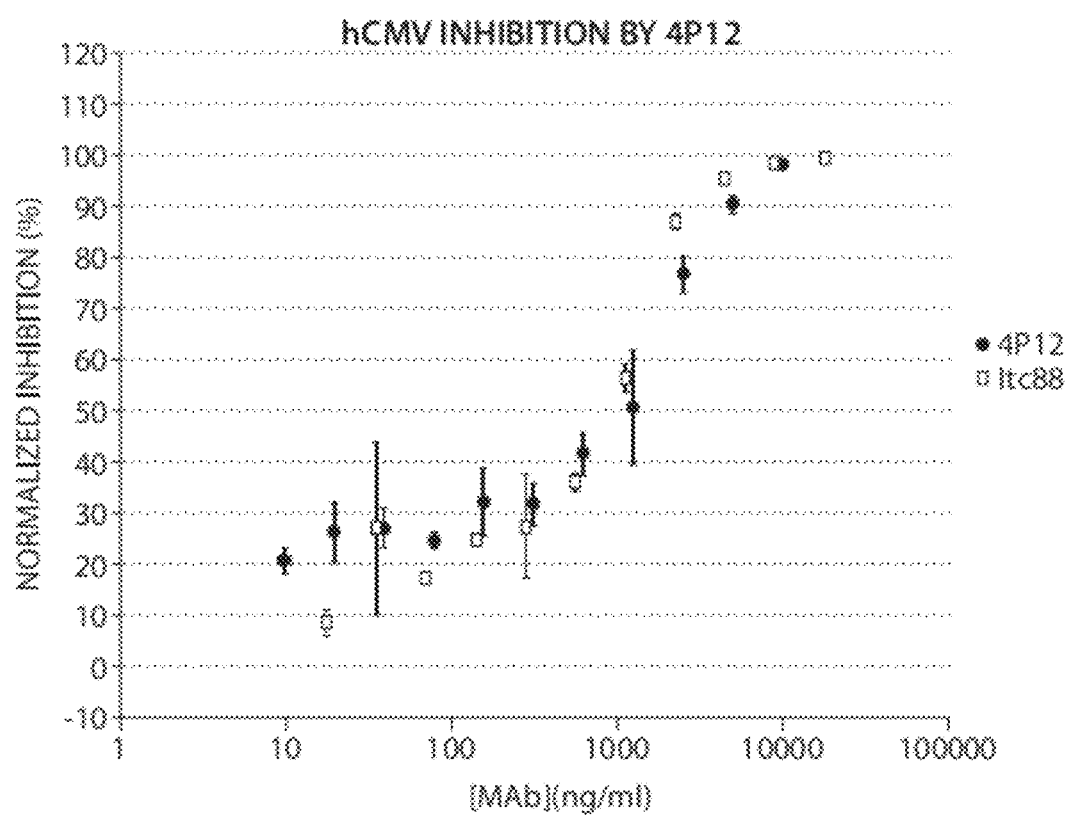
FIG. 14 is a graph depicting the neutralization of CMV virus by the 4P12 human anti-CMV antibody. The graphs show the amount of viral inhibition associated with the indicated concentrations of antibody.

The amino acid sequences of the Kappa light chain and Gamma heavy chain variable regions of the seven antibodies produced as described in Example 1 were aligned to identify conserved regions and residues, as shown in FIGS. 1A and 1B.

The variable regions of the generated anti-CMV antibodies were highly conserved. For example, the antibodies designated 3C21 and 4P12 were identical in the heavy chain variable region and had only one amino acid difference in the kappa light chain, which appears to be a PCR artifact, since the 4P12 sequence matches germline. The 5P9 gamma chain was identical to the 3G7 gamma chain and had one amino acid difference within CD3 from the 3C21 and 4P12 gamma chains. The 5P9 kappa chain was a close match (1 amino acid difference) to the kappa chain of 5A11, 3C21, and 4P12 (the latter two chains are identical to each other except for a D/E switch). The 9C16 gamma chain was most similar to the 2M16 gamma chain, and the 9C16 kappa chain was most similar to the 2N9 kappa chain (only two amino acid differences). The 3G7 kappa chain was quite different from the others, including 5P9, suggesting that the observed binding is due to the heavy chain.

These data demonstrate the highly conserved nature of antibodies that specifically bind CMV gp116 epitope AD2, and identify antibody regions important for such specificity.

Example 3

Binding of Recombinant Antibodies to CMV

The recombinant antibodies, 2F10, 2M16, 2N9, 3C21, 3G7, 4P12, and 5J12, were produced in mg quantities by larger scale transient transfections in 293 PEAK cells and tested for their ability to bind UV-inactivated CMV virus coated on a plate by ELISA. The binding ability of the antibodies was tested in the absence and presence of competing CMV gp116 epitope AD2 peptide, and also compared to the binding of a control antibody, ITC88, which also binds CMV gp116 epitope AD2. (Ohlin et al. 1993, J Virol 67: 703-710.

A secondary HRP-conjugated anti human antibody was used as the detection reagent.

As shown in FIGS. 2-8, the 2F10, 2M16, 2N9, 3C21, and 4P12 antibodies each bound CMV and were competed by CMV gp116 epitope AD2 peptide. These data demonstrate that human recombinant antibodies generated against CMV gp116 epitope are capable of also specifically binding to the CMV virus.

Example 4

Neutralization of CMV by Recombinant Antibodies

The recombinant antibodies 2F10, 2M16, 2N9, 3C21, 3G7, 4P12, were tested for their ability to inhibit hCMV by mixing hCMV virus with each of the antibodies, and then using the mixture to infect cells. The ratio of infected cells to total cells was then plotted as a function of antibody concentration. Total cell nuclei were counted by staining with YOYO-1, and hCMV infected nuclei were determined by permeabilizing the cells and determining the binding of the CMV immediate early antigen with the monoclonal antibody designated 1-K-10 (mouse IgG2a; Meridian Life Science, Cincinnati, Ohio), which in turn was detected with alexafluor (AF) 647 anti-mouse IgG (H&L) (Invitrogen; Carlsbad, Calif.). The control antibody ITC88 was also used in each experiment.

As shown in FIGS. 9-14, the 2F10, 2M16, 2N9, 3C21, and 4P12 antibodies each inhibited hCMV to a level comparable to the control ITC88 antibody. These data demonstrate that human recombinant antibodies generated against CMV gp116 AD2 epitope are capable of neutralizing the CMV virus.

Example 5

Neutralization Potency and Spectrum of HCMV Antibodies

Experimental Design and General Methods

CMV can enter a wide range of human cell types. Recently it has been reported that CMV glycoprotein-host receptor interactions vary with different cell types. However, a central issue regarding the ability of CMV to enter all cell types is the interaction of the glycoprotein gB complex (composed of proteins gp58 and gp116) with host cell receptors.

A series of anti-HCMV antibodies were generated via a procedure involving the collection of blood from several healthy human volunteers, followed by B cell harvesting and stimulation, as described in Example 1. Secreted IgG's were tested for reactivity to the AD2 epitope within the amino terminus of gB. The heavy and light chains were cloned out of B cells expressing AD2 binding IgG. Binding affinities for each antibody have been determined.

All tested antibodies potently neutralized CMV entry regardless of virus strain or the cell type of infection. This is in contrast to guinea pig CMV infection, where, as expected, none of the neutralizing antibodies had an effect. The specificity of the anti-HCMV antibodies for HCMV gB versus GPCMV gB is due to divergent sequences within these proteins that affect the efficacy of antibody binding (Table 3). The data described below supports further testing of the current set of CMV neutralizing antibodies and targeting of other CMV glycoprotein complexes.

Materials and Methods

Antibodies

Antibodies 2N9, 5P9, 2F10, 4P12, 2M16, and ITC88 were obtained using the method described above. Antibody gH(1) is a reference neutralizing anti-glycoprotein H antibody. Cytotect™ is a commercially available CMV therapeutic manufactured by Chong Lap (H.K.) CO. LTD.

Viruses

HCMV strain VR1814 was obtained from the cervical secretions of a pregnant woman. The three clinical HCMV isolates 8818, 8819, and 8824 were isolated from the sputum, bronchial alveolar lavage, and lung tissue, respectively, of infected patients and propagated in the endothelial cell line ARPE-19. The Guinea Pig CMV strain V545/82 was obtained from Mark Schleiss and contains a GFP reporter gene (McGregor A. and Schleiss M. R. (2001) Molecular Genetics and Metabolism 72(1):15-26).

Cell Lines

The cell lines used in these assays are human derived epithelial cell line ARPE-19 (retinal pigmented epithelium cells, ATCC catalog# CRL-2302), human derived fibroblast cell line NN-NHDF (neo-natal normal human dermal fibroblasts, Lonza catalog# CC-2509), human derived endothelial cell line HUVEC (human umbilical vein endothelial cells, Lonza catalog# CC-2517), and guinea pig derived fibroblast cell line JH4 (guinea pig lung fibroblast ATCC catalog# CCL-158).

Entry Assay

ARPE-19, NN-NHDF, HUVEC, and JH4 cells were seeded into 96 well plates at a concentration of $8 \times 10^3$ cells per well in a volume of 100 µl of growth media. ARPE-19 cells were grown in complete DMEM/F-12 media, NN-NHDF cells were grown in complete DMEM, HUVEC cells were grown in EGM-2 media, and JH4 cells were grown in F-12K media. Cells were incubated overnight at 37° C. and 5% $CO_2$. The next day, cells were infected first by removing the growth media and washing each well three times with 100 µl serum free media per well. ARPE-19 cells were washed with SF-DMEM/F-12, NN-NHDF cells were washed with SF-DMEM, HUVEC cells were washed with EBM-2, and JH4 cells were washed with SF-F-12K media. Antibodies were serially diluted in the serum free media for each respective cell line (see above) and mixed with enough virus to infect 50% of cells in a 96 well and were incubated at 37° C. and 5% $CO_2$ for 1 hour. Wells were infected by adding the virus/antibody mixture in 50 µl volumes per well in triplicate. ARPE and HUVEC plates were incubated at 37° C. and 5% $CO_2$ for 3 hours and NN-NHDF and JH4 plates were incubated at 37° C. and 5% $CO_2$ for 1 hour. The virus/antibody-containing media was removed and the wells were washed three times with 100 µl of the appropriate complete media (see above) per well. The final wash was not removed. The plates were incubated at 37° C. and 5% $CO_2$ overnight.

IE Staining of VR1814 and Clinical HCMV Isolates

The media was removed and the cells were fixed with 100 µl/well of 4% paraformaldehyde for 20 min at room temperature (RT). Paraformaldehyde was then removed and cells were washed three times with 100 µl/well of PBS. Each well received 50 µl of mouse anti-CMV IE antibody diluted at 1:2000 in PBS-GC containing 0.1% Triton X-100 and were incubated at RT for 1 hr.

The IE antibody was removed and the wells were washed three times with 100 µl/well of PBS. Each well received 50 µl of secondary antibody and 4',6-diamidino-2-phenylindole (DAPI) in same step by mixing Alexa Fluor 594 goat anti-mouse antibody at 1:2000 in PBS-GC and DAPI 1:5000 in PBS-GC. The plates were incubated in the dark at RT for 1 hr. The secondary antibody was removed and the wells were washed three times with 100 µl/well of PBS. The third wash was not removed. The plates were read on an Cellomics ArrayScan®VTI high content imaging platform.

Staining of GPCMV

The media was removed and the cells were fixed with 100 µl/well of 4% paraformaldehyde for 20 min at RT. Paraformaldehyde was then removed and the cells were washed three times with 100 µl/well of PBS. Each well received 50 µl DAPI 1:5000 in PBS-GC. The plates were incubated in the dark at RT for 10 minutes. The DAPI was removed and the wells were washed three times with 100 µl/well of PBS. The third wash was not removed. The plates were read on an Cellomics ArrayScan®VTI high content imaging platform.

Analysis

The data from the neutralization assays was collected using the Cellomics ArrayScan®VTI high content imaging platform. Plates were sealed with clear adhesive plate seals and loaded by robotic arm. Those plates infected with VR1814 and HCMV clinical isolates were analyzed using the Target Activation protocol NB-TA-2CH (1000 objects counted per well). Those plates infected with GPCMV were analyzed using the Molecular Translocation protocol NB-MT-Guinea Pig CMV (1000 objects counted per well). The % infectivity was calculated by dividing the number of CMV positive cells (detected by either IE or GFP depending on the virus) per well by the number of cells per well and multiplying by 100. The relative % infectivity for each dilution was calculated by taking the % infectivity of wells that had no antibody (virus only) and dividing it by the % infectivity of each dilution of each antibody and multiplying that by 100. Relative % infectivity is graphed against the concentration of the antibodies in µg/ml and the half-maximal inhibitory concentration (IC50) is determined as the concentration of antibody at which 50% of the infectious viruses observed in the virus only control is neutralized (50% relative infectivity).

Summary

The data presented here shows that the six antibodies which target the AD-2 region of DLD on HCMV glycoprotein B are capable of neutralizing HCMV entry into human derived fibroblast, epithelial, and endothelial cell lines. The IC50s of each antibody are consistent between all three cells lines infected with VR1814 which demonstrates their ability to neutralize entry regardless of the cell type. These antibodies are also capable of neutralizing entry of three low passage HCMV clinical isolates into NN-NHDFs with almost no difference in neutralizing potency observed between each antibody. This effect is also seen on HUVEC and ARPE-19 cells infected with the 8819 clinical isolate of HCMV. None of the antibodies tested were capable of neutralizing GPCMV entry into the guinea pig fibroblast cell line JH4. However, this is not unexpected since there is a great deal of sequence variability between GPCMV gB and HCMV gB in the AD-2 region of this protein. All of the anti-HCMV gB antibodies consistently neutralized all strains of HCMV virus tested on all three human derived cell lines with no significant difference in potency.

Example 6

HCMV Antibodies Potently Neutralize VR1814 Infection from Human Epithelial Cells (ARPE-19), Endothelial Cells (HUVEC), and Fibroblasts (NHDF)

Figure 15:
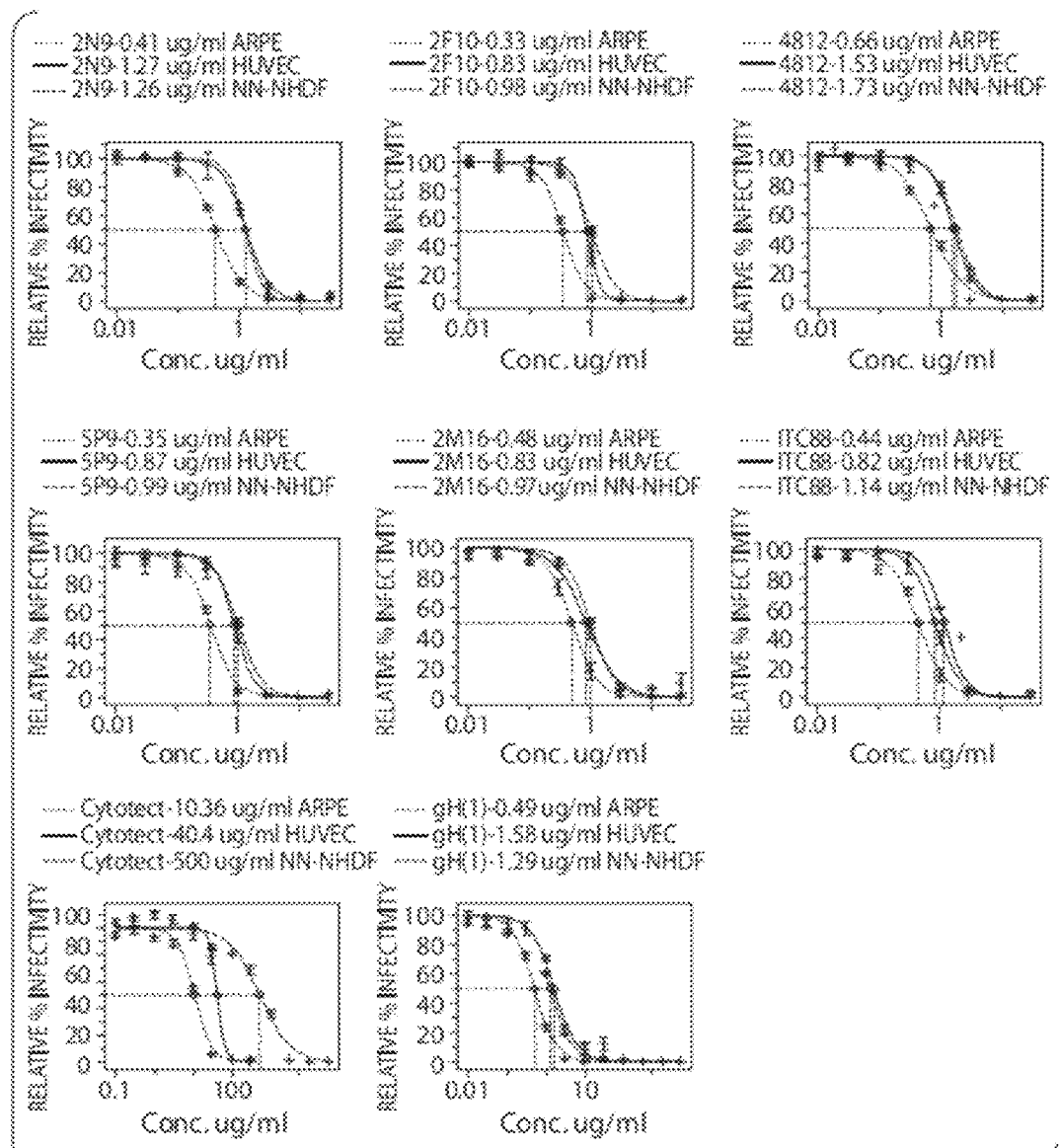
FIG. 15 is a series of graphs of the relative % infectivity versus concentration of the Human Cytomegalovirus (HCMV) Viral strain (VR1814) using 6 anti-HCMV antibodies (top 2 rows) and 2 controls (bottom row) at dilutions ranging from 30 to 0.003 μg/ml in three human cell lines.

The anti-HCMV antibodies were tested at a dilutions ranging from 30 to 0.003 µg/ml and were able to neutralize HCMV VR1814 infection of all three cell types (FIG. 15). The recorded IC50s were between 0.35 to 1.73 µg/ml and were comparable to the positive control, gH(1). There was little difference in neutralization potency between each of the antibodies. All six antibodies showed consistent neutralization of VR1814 in all cell lines with no significant variability in the IC50s.

Example 7

HCMV Antibodies Potently Neutralize Fibroblast Infection of HCMV Clinical Isolates 8818, 8819, and 8824

Figure 16:
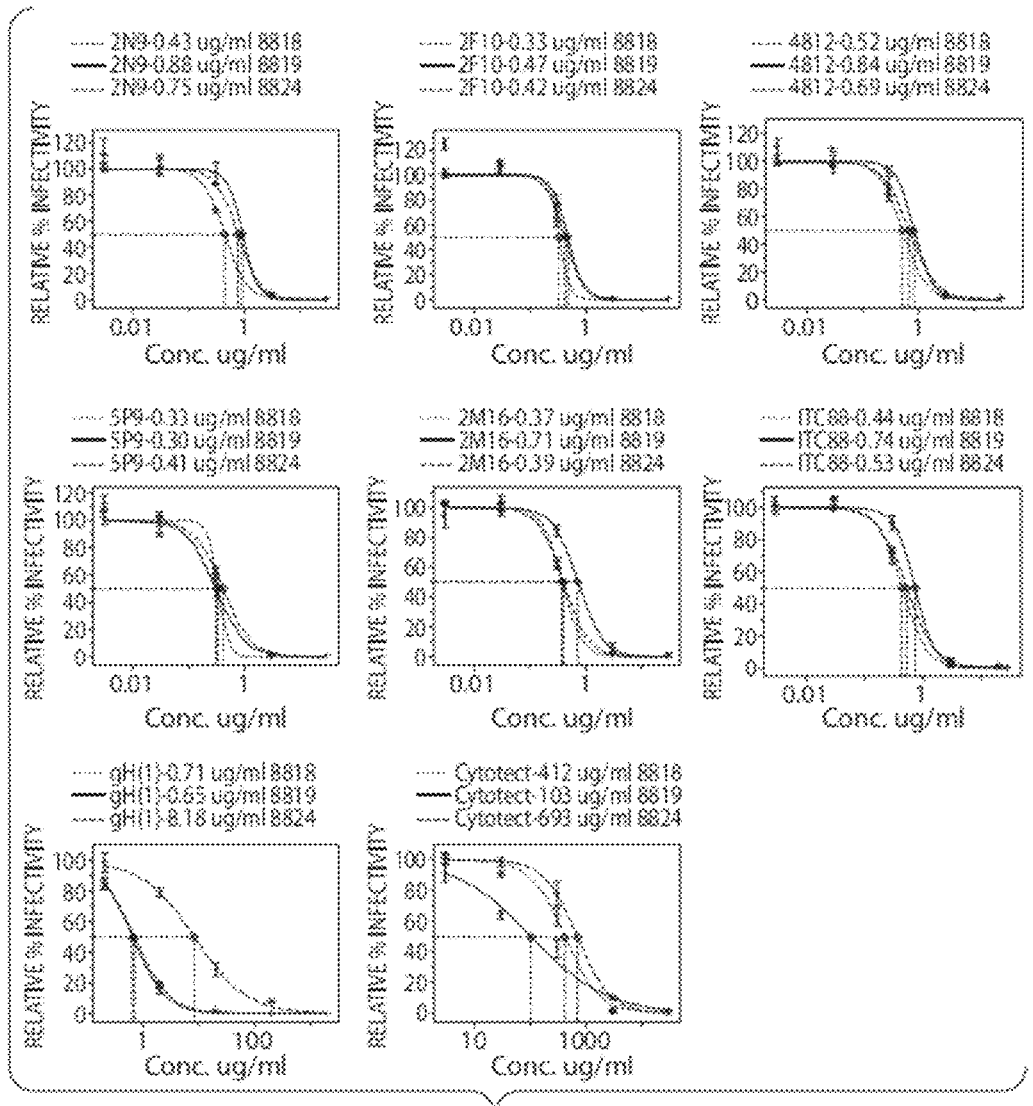
FIG. 16 is a series of graphs of the relative % infectivity versus concentration of the HCMV Viral strains (8818, 8819, and 8824) using 6 anti-HCMV antibodies (top 2 rows) and 2 controls (bottom row) at dilutions ranging from 30 to 0.003 μg/ml in human fibroblast cell lines.

The anti-HCMV antibodies were tested at dilutions ranging from 30 to 0.003 µg/ml and were able to neutralize fibroblast infections of HCMV clinical isolates 8818, 8819, and 8824 (FIG. 16). The recorded IC50s were between 0.19 to 0.83 µg/ml and were comparable to the positive control, gH(1) with the exception of clinical isolate 8824 which showed an shifted (higher) IC50 on gH(1). There was little difference between each of the antibodies. All six antibodies show consistent neutralization of all three clinical isolate infections of fibroblasts with no significant variability in the IC50s.

Example 8

HCMV Antibodies Potently Neutralize Endothelial (HUVEC) and Epithelial (ARPE-19) Infections of HCMV Clinical Isolate 8819

Figure 17:
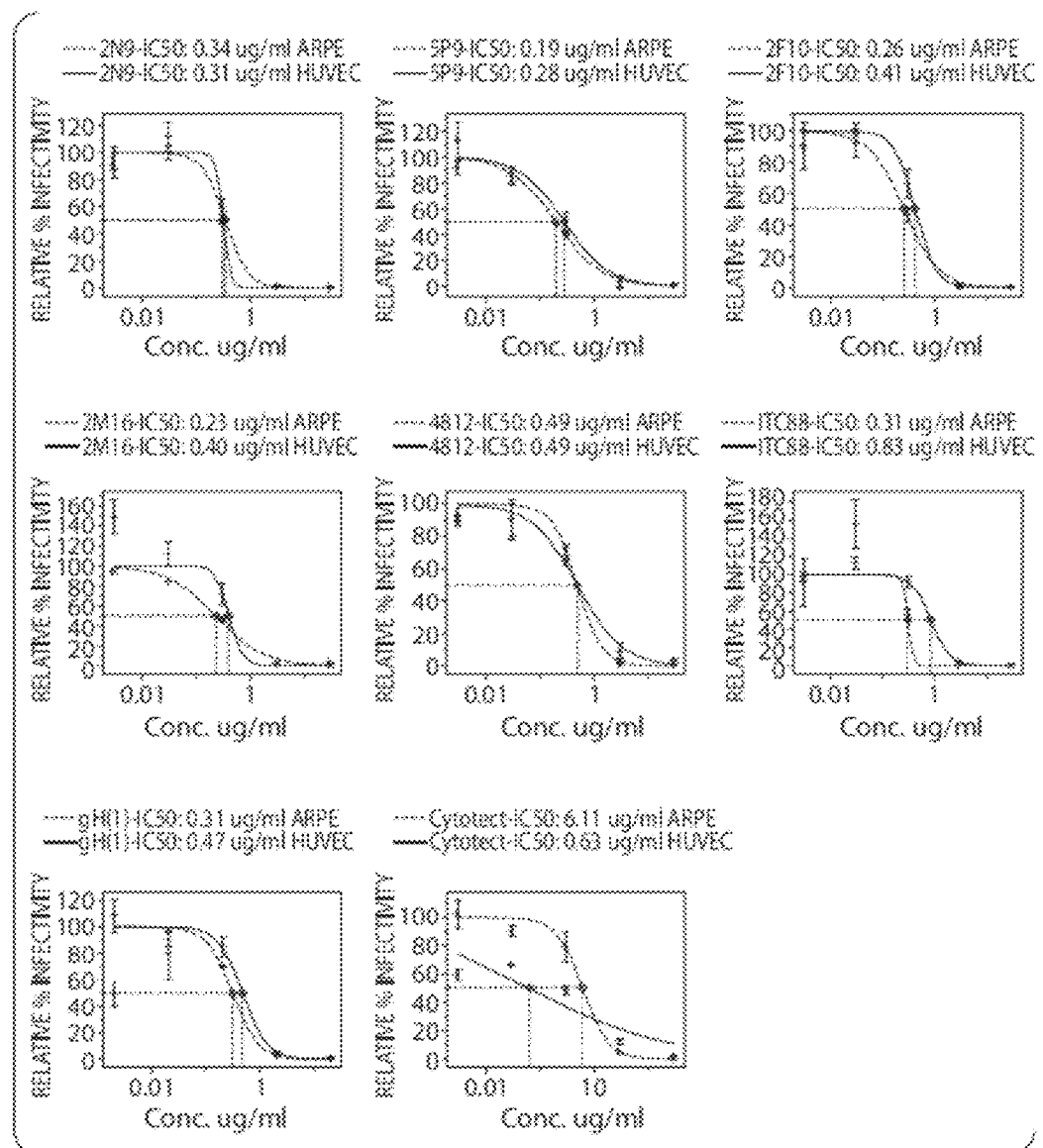
FIG. 17 is a series of graphs of the relative % infectivity versus concentration of the HCMV clinical isolate (8819) using 6 anti-HCMV antibodies (top 2 rows) and 2 controls (bottom row) at varying concentrations in human endothelial and epithelial cell lines.

Clinical isolates 8818 and 8824 are not fully adapted for endothelial cell and epithelial cell infections, and, therefore, are not currently at high enough titer to measure statistically significant differences in infection of HUVEC and ARPE-19 cells. Thus, only 8819 was on these cell types. The anti-HCMV antibodies were tested at a dilutions ranging from 30 to 0.003 µg/ml and were able to potently neutralize epithelial (ARPE-19) and endothelial cell (HUVEC) infections of the HCMV clinical isolate 8819 (FIG. 17). The recorded IC50s were between 0.19 to 0.83 µg/ml and were comparable to the positive control, gH(1). There was little difference between each of the antibodies. All six antibodies consistently neutralized the 8819 clinical isolate on both cell lines with no significant variability in the IC50s. The high standard deviations seen on some of the samples in HUVEC cells are attributed to a low amount of infectious virus. Although 8819 is capable of infecting HUVECs, the % infectivity is lower, which makes the relative % infectivity more variable.

Example 9

HCMV Antibodies do not Neutralize GPCMV Entry into Jh4 Cells

Figure 18:
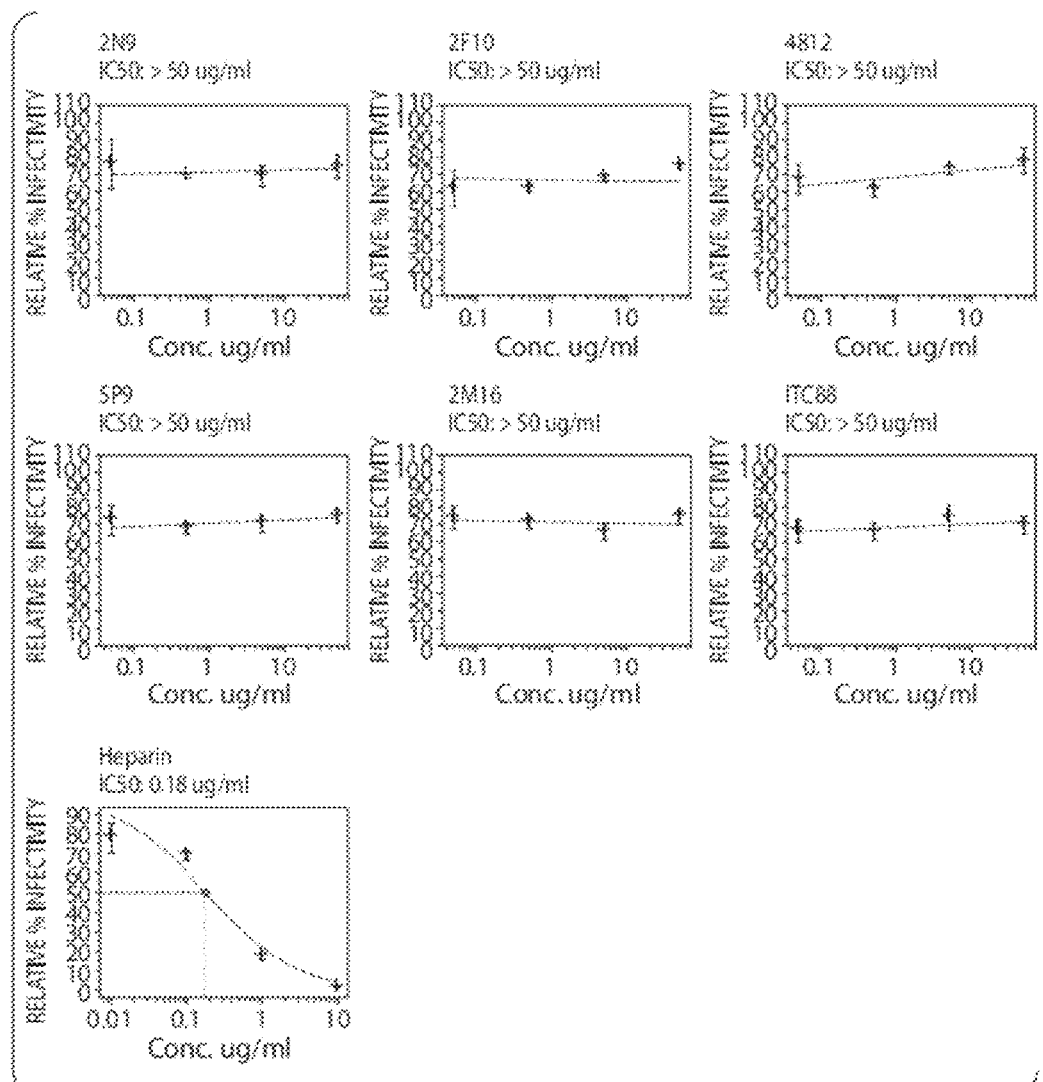
FIG. 18 is a series of graphs of the relative % infectivity versus concentration of the Guinea Pig CMV (GPCMV) Viral strain (V545/32) using 6 anti-HCMV antibodies (top 2 rows) and 2 controls (bottom row) at varying concentrations in JH4 cells.

None of the anti-HCMV antibodies were able to neutralize the V545/82 strain of GPCMV on JH4 cells (FIG. 18). The anti-HCMV antibodies had no observable effect on GPCMV entry up to 300 µg/ml, which was the highest concentration tested. Heparin was the only compound capable of inhibiting GPCMV entry into JH4 cells. The failure of these antibodies to block GPCMV entry is attributed to the large degree of sequence variability between GPCMV gB and the gB sequences on the other HCMV isolates tested (Table 3).

TABLE 3

Ad-2 Alignment.

| | | 65 | 70 | 80 | 90 | 100 | 110 | SEQ ID NO: |
|---|---|---|---|---|---|---|---|---|
| VR1814 gB | 63 | VSHRANETIYNTTLKYGDVVGVNTTKYPYRVCSMAQGTDLIRFERNIVCTPMKP | | | | | | 25 |
| 8818 gB | 63 | VSHRANETIYNTTLKYGDVVGVNTTKYPYRVCSMAQGTDLIRFERNIVCTPMKP | | | | | | 26 |
| 8819 gB | 63 | VSHGVNETIYNTTLKYGDVVGVNTTKYPYRVCSMAQGTDLIRFERNIVCTSMKP | | | | | | 27 |
| 8824 gB | 61 | VSHRANETIYNTTLKYGDVVGVNTTKYPYRVCSMAQGTDLIRFDRNIVCTPMKP | | | | | | 28 |
| GPCMV gB | 58 | S--RNNTVIRNLTASVDFSQ---RKLYPYRICSMSMGTDLVRFARTIQCVPFKP | | | | | | 29 |
| Consensus | 65 | VSHRANETIYNTTLKYGDVVGVNTTKYPYRVCSMAQGTDLIRFERNIVCTPMKP | | | | | | 30 |

AD-2 region is boxed

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for the treatment of a CMV infection in a subject, comprising administering to the subject a composition comprising an isolated anti-CMV antibody, or antigen-binding fragment thereof, wherein said antibody comprises:
   (a) a $V_H$ region comprising
      (i) a $V_H$ CDR1 region comprising the amino acid sequence of SSNGIH (SEQ ID NO: 57);
      (ii) a $V_H$ CDR2 region comprising the amino acid sequence of VISSDANDKQYADSVKG (SEQ ID NO: 58); and
      (iii) a $V_H$ CDR3 region comprising the amino acid sequence of DGTCSGGNCYSGLIDY (SEQ ID NO: 59); and
   (b) a $V_L$ region comprising
      (i) a $V_L$ CDR1 region comprising the amino acid sequence of RASQSVGGYLA (SEQ ID NO: 43);
      (ii) a $V_L$ CDR2 region comprising the amino acid sequence of ASIRAT (SEQ ID NO: 64); and
      (iii) a $V_L$ CDR3 region comprising the amino acid sequence of HQRSNWPPLT (SEQ ID NO: 65).

2. The method of claim 1, wherein the method further comprises administering an anti-viral treatment.

3. The method of claim 2, wherein said anti-viral treatment is ganciclovir, foscarnet, cidofovir, valganciclovir, or intravenous immunoglobulin (IVIG).

4. The method of claim 1, wherein said antibody is administered at a dose sufficient to neutralize CMV infection.

* * * * *